US010527495B2

(12) United States Patent
Vakhshoori et al.

(10) Patent No.: US 10,527,495 B2
(45) Date of Patent: Jan. 7, 2020

(54) METHODS AND DEVICES FOR STANDOFF DIFFERENTIAL RAMAN SPECTROSCOPY WITH INCREASED EYE SAFETY AND DECREASED RISK OF EXPLOSION

(71) Applicants: Daryoosh Vakhshoori, Cambridge, MA (US); Romain Blanchard, Lexington, MA (US); Peili Chen, Andover, MA (US); Masud Azimi, Belmont, MA (US); Tobias Mansuripur, Cambridge, MA (US); Kalyani Krishnamurthy, Lincoln, MA (US); Arran M. Bibby, Savannah, GA (US); Fred R. Huettig, III, Sudbury, MA (US); Gokhan Ulu, Newton, MA (US); Greg Vander Rhodes, Lexington, MA (US)

(72) Inventors: Daryoosh Vakhshoori, Cambridge, MA (US); Romain Blanchard, Lexington, MA (US); Peili Chen, Andover, MA (US); Masud Azimi, Belmont, MA (US); Tobias Mansuripur, Cambridge, MA (US); Kalyani Krishnamurthy, Lincoln, MA (US); Arran M. Bibby, Savannah, GA (US); Fred R. Huettig, III, Sudbury, MA (US); Gokhan Ulu, Newton, MA (US); Greg Vander Rhodes, Lexington, MA (US)

(73) Assignee: Pendar Technologies, LLC, Cambridge, MA (US)

( * ) Notice: Subject to any disclaimer, the term of this patent is extended or adjusted under 35 U.S.C. 154(b) by 0 days.

(21) Appl. No.: 16/351,129

(22) Filed: Mar. 12, 2019

(65) Prior Publication Data

US 2019/0368937 A1 Dec. 5, 2019

Related U.S. Application Data

(63) Continuation of application No. PCT/US2019/021312, filed on Mar. 8, 2019.

(Continued)

(51) Int. Cl.
*G01J 3/44* (2006.01)
*G01K 11/32* (2006.01)
(Continued)

(52) U.S. Cl.
CPC .......... *G01J 3/4412* (2013.01); *G01J 3/0208* (2013.01); *G01J 3/0216* (2013.01); *G01J 3/0224* (2013.01);
(Continued)

(58) Field of Classification Search
CPC ............... G01J 3/44; G01J 3/0272; G01J 3/65
See application file for complete search history.

(56) References Cited

U.S. PATENT DOCUMENTS 5,455,673 A   10/1995 Alsmeyer et al.
5,534,997 A   7/1996 Schrader
(Continued)

OTHER PUBLICATIONS

International Search Report and Written Opinion in International Patent Application No. PCT/US19/21312 dated Jun. 27, 2019, 24 pages.

(Continued)

*Primary Examiner* — Maurice C Smith
(74) *Attorney, Agent, or Firm* — Smith Baluch LLP

(57) ABSTRACT

A compact, portable Raman spectrometer makes fast, sensitive standoff measurements at little to no risk of eye injury or igniting the materials being probed. This spectrometer uses differential Raman spectroscopy and ambient light measurements to measure point-and-shoot Raman signatures of dark or highly fluorescent materials at distances of (Continued)

1 cm to 10 m or more. It scans the Raman pump beam(s) across the sample to reduce the risk of unduly heating or igniting the sample. Beam scanning also transforms the spectrometer into an instrument with a lower effective safety classification, reducing the risk of eye injury. The spectrometer's long standoff range automatic focusing make it easier to identify chemicals through clear and translucent obstacles, such as flow tubes, windows, and containers. And the spectrometer's components are light and small enough to be packaged in a handheld housing or housing suitable for a small robot to carry.

27 Claims, 43 Drawing Sheets

Related U.S. Application Data

(60) Provisional application No. 62/793,601, filed on Jan. 17, 2019, provisional application No. 62/692,657, filed on Jun. 29, 2018, provisional application No. 62/678,065, filed on May 30, 2018.

(51) Int. Cl.
*G01J 3/02* (2006.01)
*G01J 3/06* (2006.01)

(52) U.S. Cl.
CPC ........... *G01J 3/0237* (2013.01); *G01J 3/0248* (2013.01); *G01J 3/0256* (2013.01); *G01J 3/0264* (2013.01); *G01J 3/0272* (2013.01); *G01J 3/06* (2013.01); *G01J 3/4406* (2013.01); *G01K 11/3213* (2013.01); *G01J 2003/4424* (2013.01); *G01K 2011/324* (2013.01)

(56) References Cited

U.S. PATENT DOCUMENTS

| | | | |
|---|---|---|---|
| 5,946,090 A | 8/1999 | Tashiro et al. | |
| 6,485,413 B1 | 11/2002 | Boppart et al. | |
| 7,002,679 B2 | 2/2006 | Brady et al. | |
| 7,420,664 B2 | 9/2008 | Treado et al. | |
| 7,796,251 B2 | 9/2010 | Ponsardin et al. | |
| 7,864,311 B2 | 1/2011 | Klehr et al. | |
| 7,982,869 B2 * | 7/2011 | Ban | G01J 3/4412 250/281 |
| 8,159,662 B2 | 4/2012 | Rezac et al. | |
| 8,570,507 B1 | 10/2013 | Cooper et al. | |
| 8,867,033 B2 | 10/2014 | Carron et al. | |
| 8,988,678 B2 | 3/2015 | Watson et al. | |
| 9,157,801 B2 | 10/2015 | Dottery et al. | |
| 9,255,841 B2 | 2/2016 | Witinski et al. | |
| 9,459,146 B2 | 10/2016 | Carron et al. | |
| 9,523,610 B2 | 12/2016 | Watson et al. | |
| 9,570,878 B2 | 2/2017 | Clowes et al. | |
| 9,581,493 B2 | 2/2017 | Cooper et al. | |
| 9,778,195 B2 | 10/2017 | Day et al. | |
| 9,791,313 B2 | 10/2017 | Watson et al. | |
| 10,072,984 B2 | 9/2018 | Carron et al. | |
| 10,222,336 B2 * | 3/2019 | Kuo | G01N 21/65 |
| 2008/0165344 A1 | 7/2008 | Treado et al. | |
| 2008/0204715 A1 * | 8/2008 | Klehr | G01J 3/10 356/73 |
| 2012/0044478 A1 | 2/2012 | Re et al. | |
| 2012/0154801 A1 | 6/2012 | Carron et al. | |
| 2012/0162642 A1 | 6/2012 | Watson et al. | |
| 2013/0293882 A1 | 11/2013 | Dottery et al. | |
| 2013/0316467 A1 | 11/2013 | Carron et al. | |
| 2014/0104611 A1 | 4/2014 | Watson et al. | |
| 2015/0099292 A1 | 4/2015 | Carron et al. | |
| 2015/0260576 A1 | 9/2015 | Watson et al. | |
| 2016/0202124 A1 * | 7/2016 | Lambert | G01J 3/44 356/301 |
| 2016/0223400 A1 | 8/2016 | Carron et al. | |
| 2017/0234728 A1 | 8/2017 | Buller et al. | |
| 2017/0254754 A1 | 9/2017 | Gibson et al. | |
| 2018/0195965 A1 | 7/2018 | Carron et al. | |
| 2018/0283941 A1 | 10/2018 | Watson et al. | |

OTHER PUBLICATIONS

Conti et al., "Portable Sequentially Shifted Excitation Raman spectroscopy as an innovative tool for in situ chemical interrogation of painted surfaces." Analyst 141.15 (2016): 4599-4607.

Delori et al.,"Maximum permissible exposures for ocular safety (ANSI 2000), with emphasis on ophthalmic devices." JOSA A 24.5 (2007): 1250-1265.

Gebrekidan et al.,"A shifted-excitation Raman difference spectroscopy (SERDS) evaluation strategy for the efficient isolation of Raman spectra from extreme fluorescence interference." Journal of Raman Spectroscopy 47.2 (2016): 198-209.

Grüber et al.,"Advanced instantaneous shifted-excitation Raman difference spectroscopy (iSERDS) using a laser pointer." Journal of Raman Spectroscopy 47.9 (2016): 1049-1055.

Maiwald et al., "A portable shifted excitation Raman difference spectroscopy system: Device and field demonstration." Journal of Raman Spectroscopy 47.10 (2016): 1180-1184.

McCain et al.,"Multi-excitation Raman spectroscopy technique for fluorescence rejection." Optics Express 16.15 (2008): 10975-10991.

Moore et al., "Portable Raman explosives detection." Analytical and bioanalytical chemistry 393.6-7 (2009): 1571-1578.

Mosier-Boss et al., "Fluorescence rejection in Raman spectroscopy by shifted-spectra, edge detection, and FFT filtering techniques." Applied Spectroscopy 49.5 (1995): 630-638.

Shreve et al., "Effective rejection of fluorescence interference in Raman spectroscopy using a shifted excitation difference technique." Applied spectroscopy 46.4 (1992): 707-711.

Tuschel, David, 'Raman Thermometry' in Molecular Spectroscopy Workbench: the 2016 Collection, Spectroscopy (www.spectroscopyonline.com). Dec. 1, 2016. Accessed at http://www.spectroscopyonline.com/david-tuschel on Jan. 23, 2019. 4 pages.

Zhao et al.,"Automated fluorescence rejection using shifted excitation Raman difference spectroscopy." Applied Spectroscopy 56.7 (2002): 834-845.

\* cited by examiner

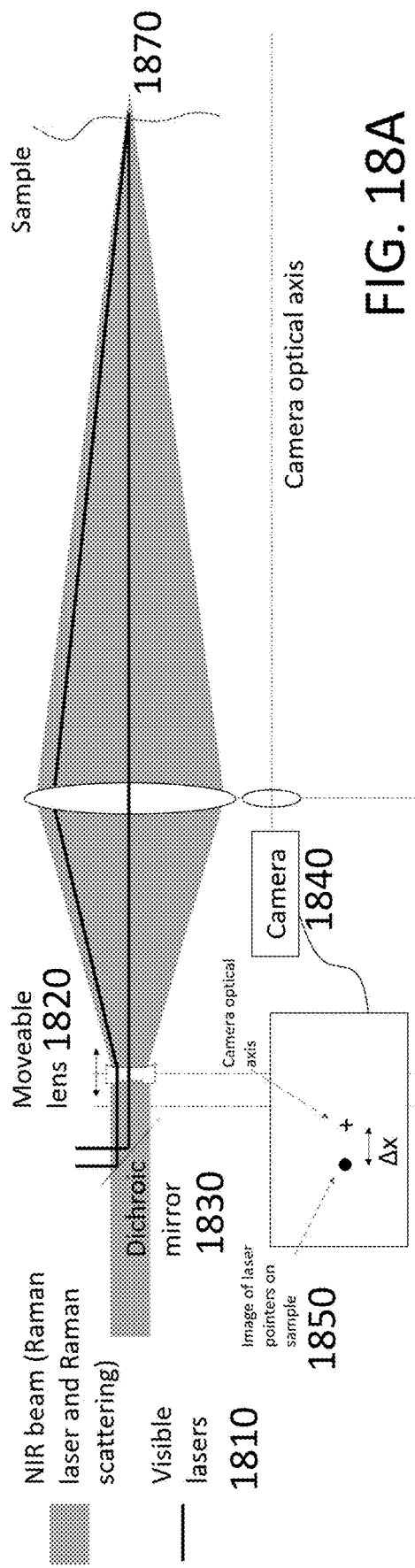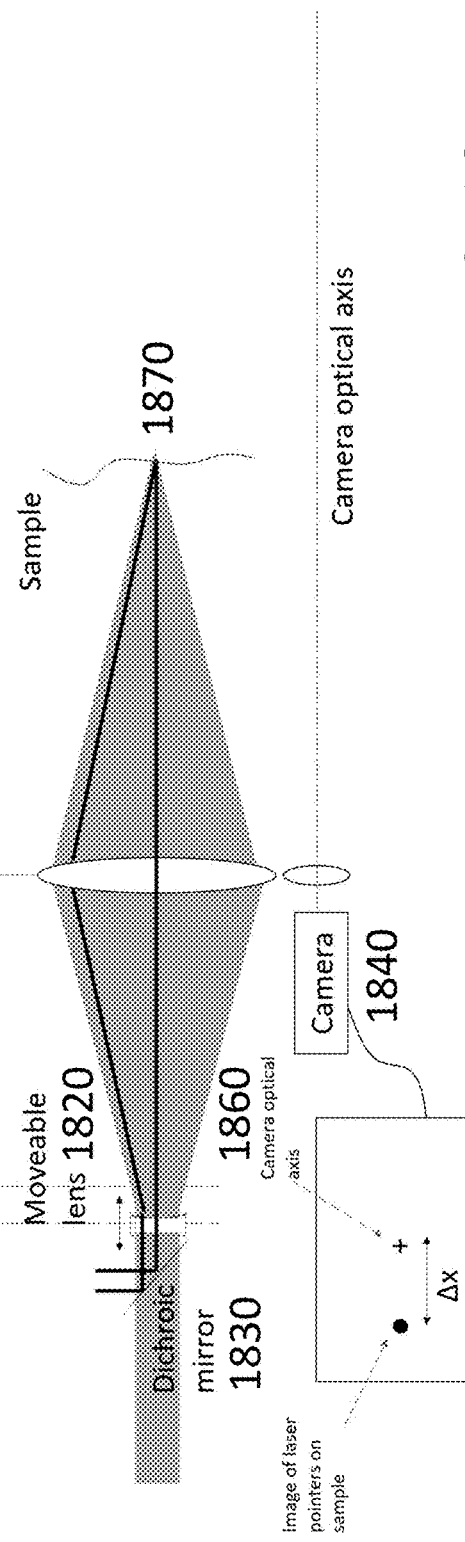
FIG. 18A
FIG. 18B

Example of result screen

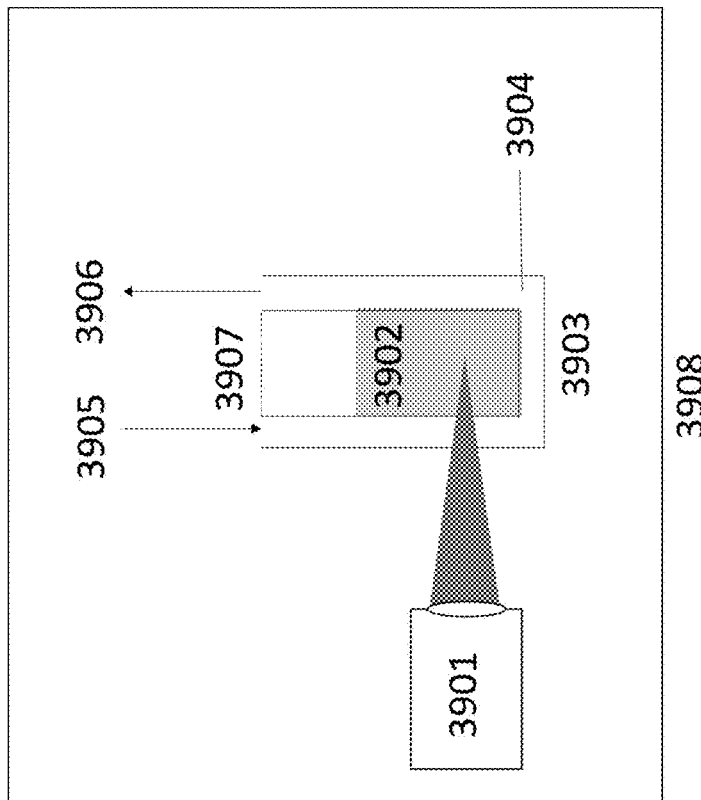
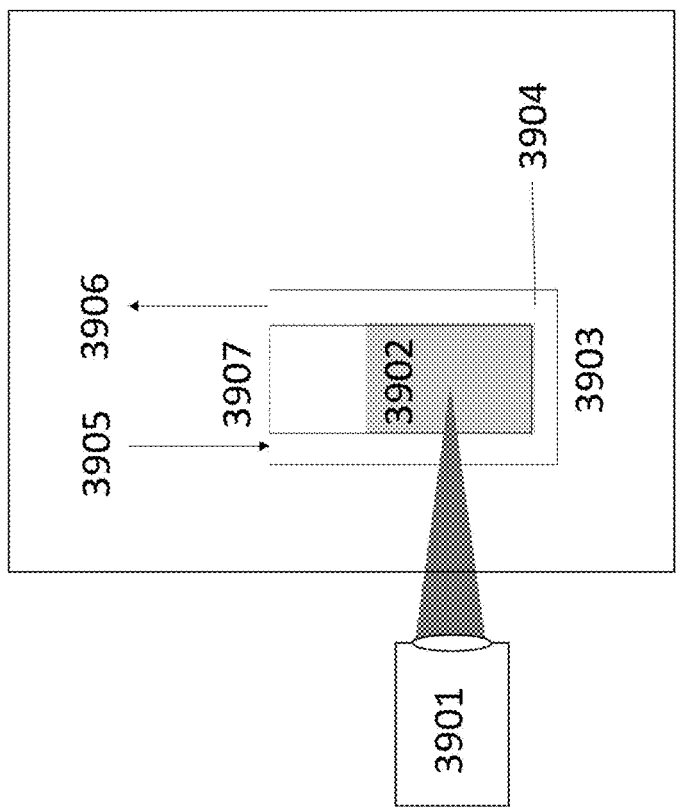
FIG. 39A
FIG. 39B

METHODS AND DEVICES FOR STANDOFF DIFFERENTIAL RAMAN SPECTROSCOPY WITH INCREASED EYE SAFETY AND DECREASED RISK OF EXPLOSION

CROSS-REFERENCE TO RELATED APPLICATIONS

This application is a bypass continuation of International Application No. PCT/US2019/021312, filed Mar. 8, 2019, and entitled "Methods and Devices for Standoff Differential Raman Spectroscopy with Increased Eye Safety and Decreased Risk of Explosion," which in turn claims the priority benefit, under 35 U.S.C. 119(e), of: U.S. Provisional Application No. 62/793,601 entitled "EYE-SAFE AND EXPLOSION MITIGATED STANDOFF DIFFERENTIAL RAMAN SPECTROSCOPY," filed Jan. 17, 2019; U.S. Provisional Application No. 62/692,657 entitled "EYE-SAFE AND EXPLOSION MITIGATED STANDOFF DIFFERENTIAL RAMAN SPECTROSCOPY," filed Jun. 29, 2018; and U.S. Provisional Application No. 62/678,065 entitled "DEVICE AND METHODS FOR EYE-SAFE AND EXPLOSION MITIGATED STANDOFF RAMAN SPECTROSCOPY," filed May 30, 2018. Each of these applications is incorporated herein by reference in its entirety. This application also directly claims the priority benefit, under 35 U.S.C. 119(e), of: U.S. Provisional Application No. 62/793,601 entitled "EYE-SAFE AND EXPLOSION MITIGATED STANDOFF DIFFERENTIAL RAMAN SPECTROSCOPY," filed Jan. 17, 2019; U.S. Provisional Application No. 62/692,657 entitled "EYE-SAFE AND EXPLOSION MITIGATED STANDOFF DIFFERENTIAL RAMAN SPECTROSCOPY," filed Jun. 29, 2018; and U.S. Provisional Application No. 62/678,065 entitled "DEVICE AND METHODS FOR EYE-SAFE AND EXPLOSION MITIGATED STANDOFF RAMAN SPECTROSCOPY," filed May 30, 2018. As noted above, each of these applications is incorporated herein by reference in its entirety.

BACKGROUND

Raman spectroscopy has proven to be a highly valuable portable analytical tool for accurate chemical identifications. In the most common implementation, a Raman spectrometer requires the operator to hold the device close (e.g., less than couple of centimeters away) to the substance under investigation, illuminating the substance with a pump laser and collecting the Raman scattering. With typical portable Raman instruments, the laser hazard zone is half a meter or larger and laser training is required for the operators of such a tool since it is typically classified as a Class 3B instrument. Standoff Raman systems with a meter or more of standoff distance from sample also exist but the laser hazard zone is much larger (e.g., a few meters) preventing easy adoption of such systems in the field in addition to burdening the operators and manufacturers with a more onerous laser safety training class.

For visible or near-infrared (NIR) Raman systems laser hazard is due to ocular damage, in particular thermal damage to the retina, from the laser used as the Raman pump. The damage is a function of radiance ($W/m^2/sr$), distance of Raman laser source to the eye, wavelength, and exposure time. For a standoff Raman system, the laser power exits the system output aperture and converges to a spot outside the system, on a target sample.

SUMMARY

Examples of the devices and methods described here aim at increasing or maximizing the allowable output laser power of an instrument of a certain laser class, while also mitigating risks (e.g., explosion) or other issues (e.g., perturbation of the kinetics of a reaction) linked to local heating of the analyte. A spectroscopic laser-based instrument with an assigned class of 3B may be downgraded to a class of 3R (or, similarly, an instrument with an assigned class of 3R may be downgraded to class 1) with the use of the devices and methods presented here. A spectroscopic laser-based instrument that can ignite some analytes may be made to reduce or eliminate the risk of igniting these analytes using the devices and methods presented here. A spectroscopic laser-based instrument that causes significant local heating of an analyte may be made to cause nominal local heating of the analyte using the devices and methods presented here.

Here we present a method for implementing an eye-safe (Class 3R or lower) Raman system using beam scanning. The system operates at a standoff distance of a few centimeters to a few meters with a laser output power that would correspond to a higher-class system (from an eye safety point of view) if beam scanning was not used (e.g., the system would be class 3B without scanning and can be made as safe as a class 3R instrument with proper beam scanning).

The signal to noise ratio (SNR) of a given Raman system increases as the Raman pump power increases. There is thus a competition between the desire for a high SNR system, providing rapid spectral acquisition for fast chemical analysis, and the desire for an eye-safe system. A second trade-off is with regard to the etendue of the spectrometer: a spectrometer with a large etendue can stare at a wider area on the sample. This is often used to improve eye safety by widening the Raman pump spot size on the sample, thereby reducing the radiance. However, increasing the etendue of the spectrometer generally reduces its resolution. We present here a system that allows to maintain a small etendue (e.g. smaller than $0.2\ mm^2$) and corresponding potential for high resolution, together with a high Raman pump power (e.g. larger than 5 mW) for good SNR and fast spectral acquisition, while reducing the risks of ocular damage.

A high radiance on the sample is also sometimes associated with explosion or ignition risks of the material analyzed. Alternatively, the sample may heat up so much under the high radiance of the Raman pump that it emits an incandescent glow that interfere with or altogether prevent the measurement. From this point of view, there is also a need to reduce the radiance on the sample, which is addressed by the system presented here.

If the laser spot is scanned on a sample over a scan area with a high enough speed, the effective ocular laser spot size approaches that of the scan area, significantly increasing the threshold for eye-safe laser operation. (The scan is an areal scan that probes a finite volume or layer of material since the beam has a finite depth of focus and there is scattering inside the sample.) Whether this effective average exposed area or the instantaneous scanned spot should be considered depends on the exact scan parameters and may be evaluated as outlined in the laser safety standards. The instantaneous spot size, scan area, and scan speed, as well as the divergence of the laser beam can be optimized or selected to produce such enhanced eye-safe standoff Raman system. In particular the scan pattern can be optimized for homogeneous illumination to prevent "hot regions" in the scan area. If the laser spot dwells for too long in a region, the ocular damage threshold can be reached, which means the irradiance on the retina can exceed the threshold for damage, for example thermal damage. Empty or hollow scan patterns can have small effective scan areas. For example, a fast circumferential scan produces an effective scan area which is approximately the product of diameter of laser spot and the circumference of the scanned circle. If the inner area of the circle is scanned as well, the total scan area (and hence the effective spot size) may approach the area of the circle, which is larger than the effective area of the circular scan.

By properly choosing the scan parameters, as explained below, to produce large effective area for ocular damage, the temperature rise on the sample surface is also reduced. Both ocular damage and sample temperature rise are due to concentrated laser power dwelling for sufficient time on the same spot. The thermal diffusion of retinal tissue would likely be different than the thermal diffusion of the sample but in both cases a reduced temperature rise can be obtained with the use of appropriate scanning.

Eye-safe lasers are typically understood to be lasers that emit less than 5 mW of output power (e.g., class 1, 2 and 3R lasers, but not class 3B lasers), Eye-safe lasers can be operated without special safety training. Class 3R instruments are considered eye-safe when handled carefully and have a small hazard potential for accidental exposure. Some commercial laser pointers are class 3R instruments.

More generally, the devices and methods presented here lower the eye safety classification of a given system using laser beam scanning. For example, a class 3B system can be transformed into a class 3R system using laser scanning. Or a Class 3R system may be transformed into a Class 1 system. Or a Class 4 system may be transformed into a Class 3B system.

While the inventive devices and methods are presented here in the context of Raman spectroscopy, implying the use of a pump laser illuminating a sample, and whereby the scattered light is collected by an optical system and focused into a spectrometer entrance slit, the inventive devices and methods are applicable to other laser spectroscopy techniques since they address in general increasing eye safety for instruments requiring the illumination of a sample with a bright focused beam of light. Other forms of Raman spectroscopy (coherent Raman spectroscopy, resonant Raman spectroscopy, difference Raman spectroscopy, spatially offset Raman spectroscopy, surface-enhanced Raman spectroscopy, etc.) can benefit similarly from the devices and methods described here as well as other laser-based techniques, such as laser induced fluorescence spectroscopy.

The devices and methods presented here are applicable to laser-based instruments in general. They can be implemented without an enclosure or shield to prevent the beam from exiting a certain perimeter. They are of particular utility for standoff instruments with a certain length of open air (e.g., >2 cm) between the instrument and the sample. The technology presented here involves laser beam scanning, together with the implementation of fail-safe monitoring and automatic shut-off mechanisms. It allows the use of higher power laser than would be otherwise allowed without laser beam scanning, within a certain laser class.

An inventive Raman system may have a standoff distance larger than 2 centimeters. The system includes several features designed to mitigate the unique challenges due to the increased standoff distance, and the interference of ambient light and the signal variations resulting from the operator's hand movements, as well as challenges common to most Raman systems, such as sample fluorescence, risk of sample explosion or ignition, and eye safety risks.

An example Raman system can be implemented as a handheld standoff instrument, a Raman microscope, or a general chemical analysis tool, for example, used to monitor chemical reactions, identify materials, confirm a material composition, or quantify relative concentrations in a mixture of several materials. It may have one or more of the following features:

The system may measure a sample located at a distance greater than 2 centimeters from the instrument;

The system may allow for handheld operation and thus assume a dynamic signal, within particular variations in ambient light background, sample fluorescent background, as well as Raman signal during the measurement;

The system may use at least two Raman lasers in a difference Raman mode of operation to mitigate the effects of sample (or substrate) fluorescence. A tunable laser may be used instead of several lasers since the spectra are acquired successively with different Raman pump wavelength;

The system may also use difference Raman technology to remove the background spectrum due to blackbody emission from a hot sample;

The laser or lasers used as Raman pump laser may be uncooled, allowing to reduce the system weight and power consumption. A small amount of the Raman laser light may be leaked in the Raman probe towards the spectrometer, causing the zero-Stokes shift line (Rayleigh scattering) to be visible in the Raman spectrum. The zero-Stokes shift line provides a reference to compute the Stokes shifts even if the Raman laser wavelength varies over time;

The system may use short integration frame times with interleaved Raman frames and background frames to provide robustness against signal variations;

The system may be compatible with laser beam scanning, which increases eye safety of the instrument and reduces the risk of sample ignition or explosion for a given laser power output and spot size;

The timing of the different processes (Raman laser modulation or switching, spectral acquisition, laser beam scanning) may be synchronized and chosen in a manner aimed at reducing or minimizing measurement fluctuations due to laser beam scanning or potential ambient light modulation;

The system may include a camera imaging the sample;

The system may use the visual information from the camera for image stabilization;

The system may allow the user to indicate a feature of interest, for example, by pressing a touchscreen displaying an image of the area surrounding a sample, to indicate a desired measurement spot. The system can lock onto this spot, e.g., by automatically steering the telescope optics to focus the Raman probe to that spot and maintaining that aim. The system maintains this aim by correcting automatically for the hand movements of the operator using information from the camera.

The system may have an adjustable focus distance;

The system may have an autofocus system to automatically adjust the focus distance and increase or maximize Raman signal;

The auto-focus system may allow for an offset setting so that the system may be focused a short distance away from a first scattering surface;

The auto-focus may be able to detect multiple interfaces along the optical axis and sequentially tune the instrument focus to realize measurements at or near these interfaces, or at any point between consecutive interfaces.

Unless noted otherwise, the laser safety considerations presented here are derived from the 2014 revision of the IEC 60825-1 standard since US Federal Laser Notice 50 allows classification according to IEC 60825-1, instead of compliance with 21 CFR 1040.10 and 1040.11. However, since these eye-safety standards refer to the same bio-physical constraints, they tend to present similar derivations and the strategy presented here is applicable in general to increase eye-safety of a laser-based instrument. Details of some bio-physical considerations underlying the eye-safety standards can be found in Francois C. Delori, Robert H. Webb, and David H. Sliney, "Maximum permissible exposures for ocular safety (ANSI 2000), with emphasis on ophthalmic devices," J. Opt. Soc. Am. A 24, 1250-1265 (2007), which is incorporated herein by reference in its entirety.

It should be appreciated that all combinations of the foregoing concepts and additional concepts discussed in greater detail below (provided such concepts are not mutually inconsistent) are contemplated as being part of the inventive subject matter disclosed herein. All combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTIONS OF THE DRAWINGS

Figure 7:
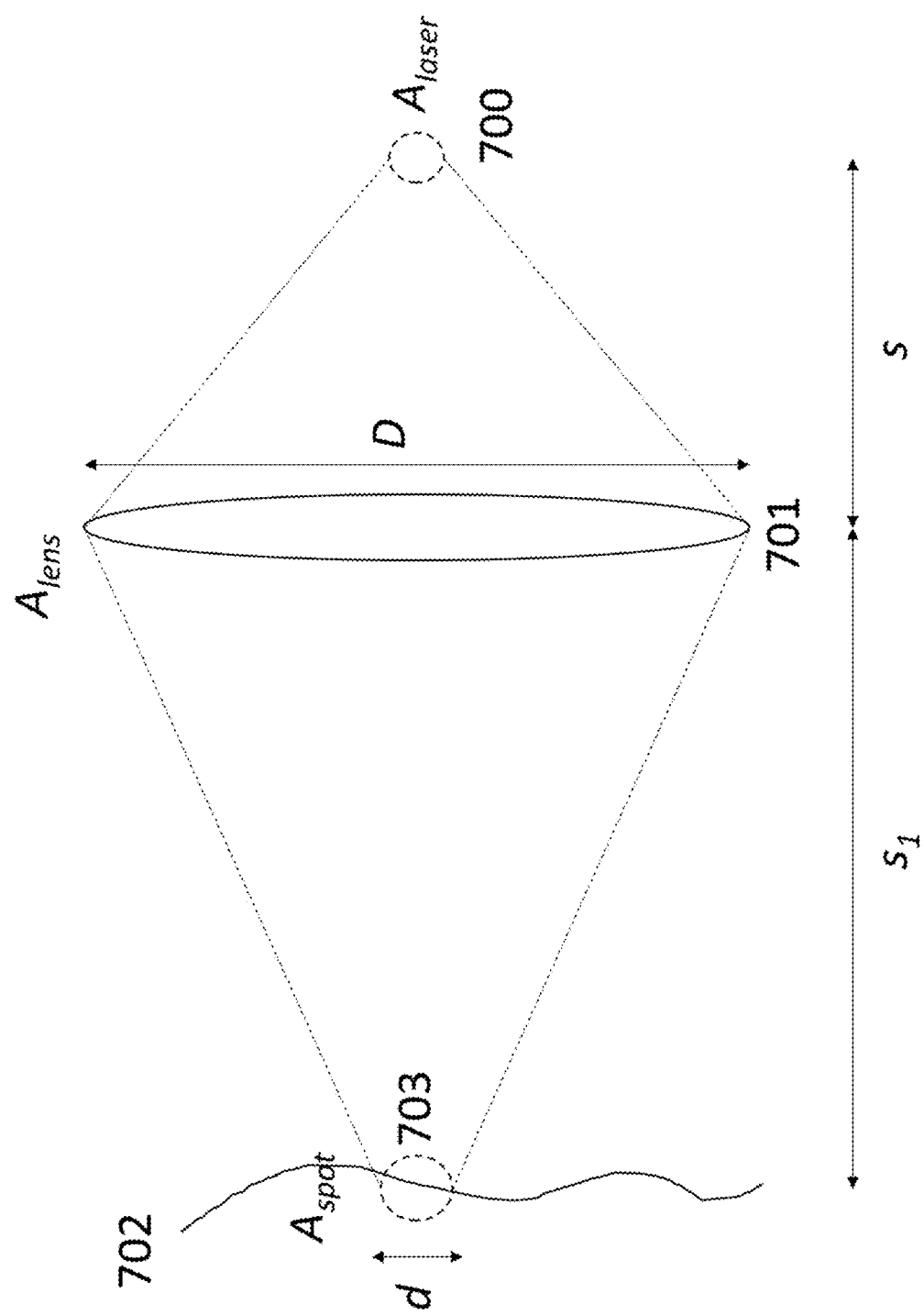

FIG. 7 introduces the notations used to characterize the system etendue.

Figure 8B:
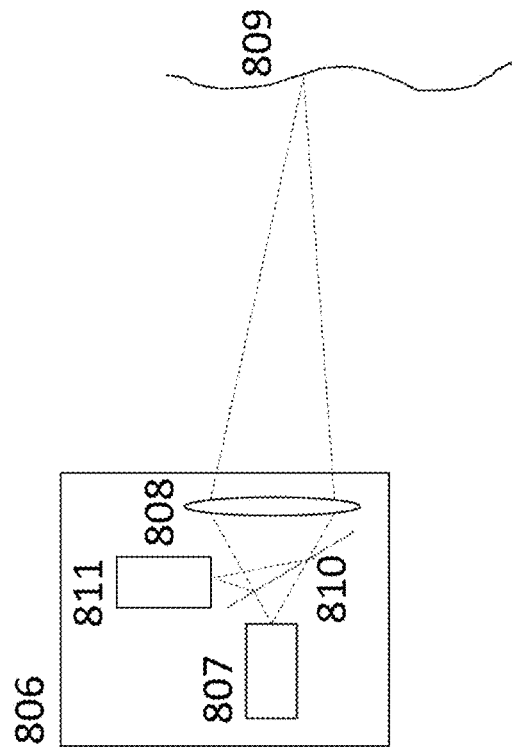
Figure 8A:
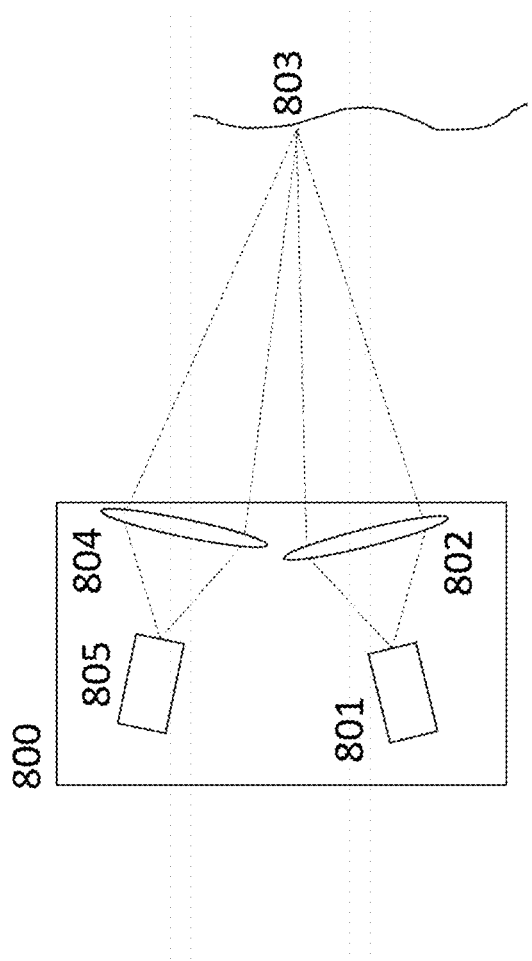

FIG. 8A is a schematic of a standoff sample temperature monitoring system.

FIG. 8B is a schematic of another embodiment of a standoff temperature monitoring system.

Figure 9:
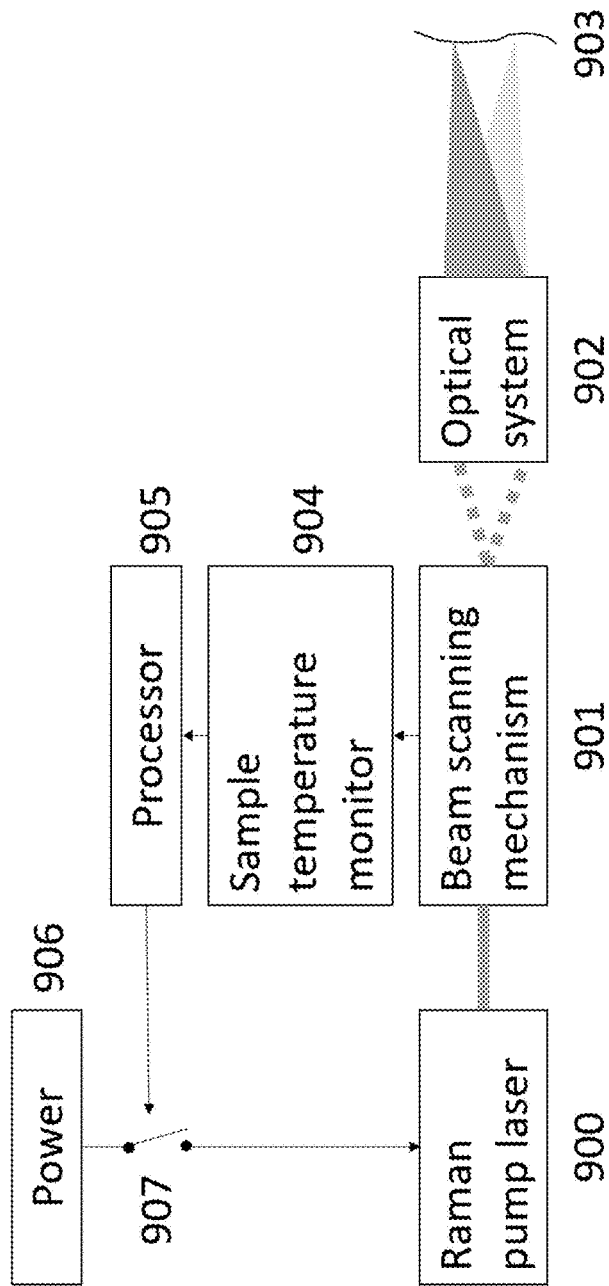

FIG. 9 is a schematic of a standoff Raman system's fail-safe mechanism (e.g., for explosion or ignition risk mitigation) based on measurement of the sample temperature.

Figure 10:
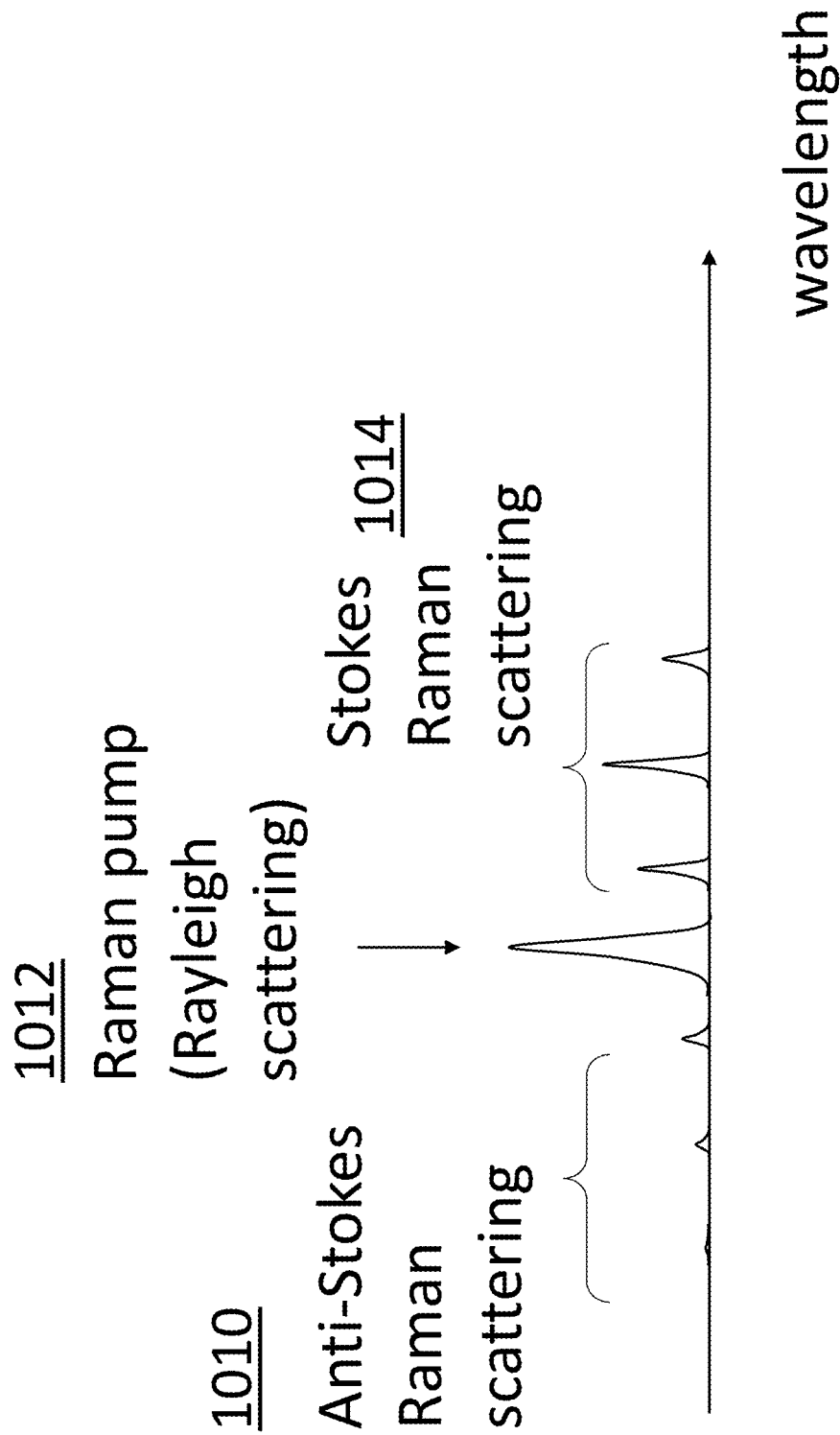

FIG. 10 illustrates the different Raman signals that can be observed and may be useful for temperature measurement.

Figure 11:
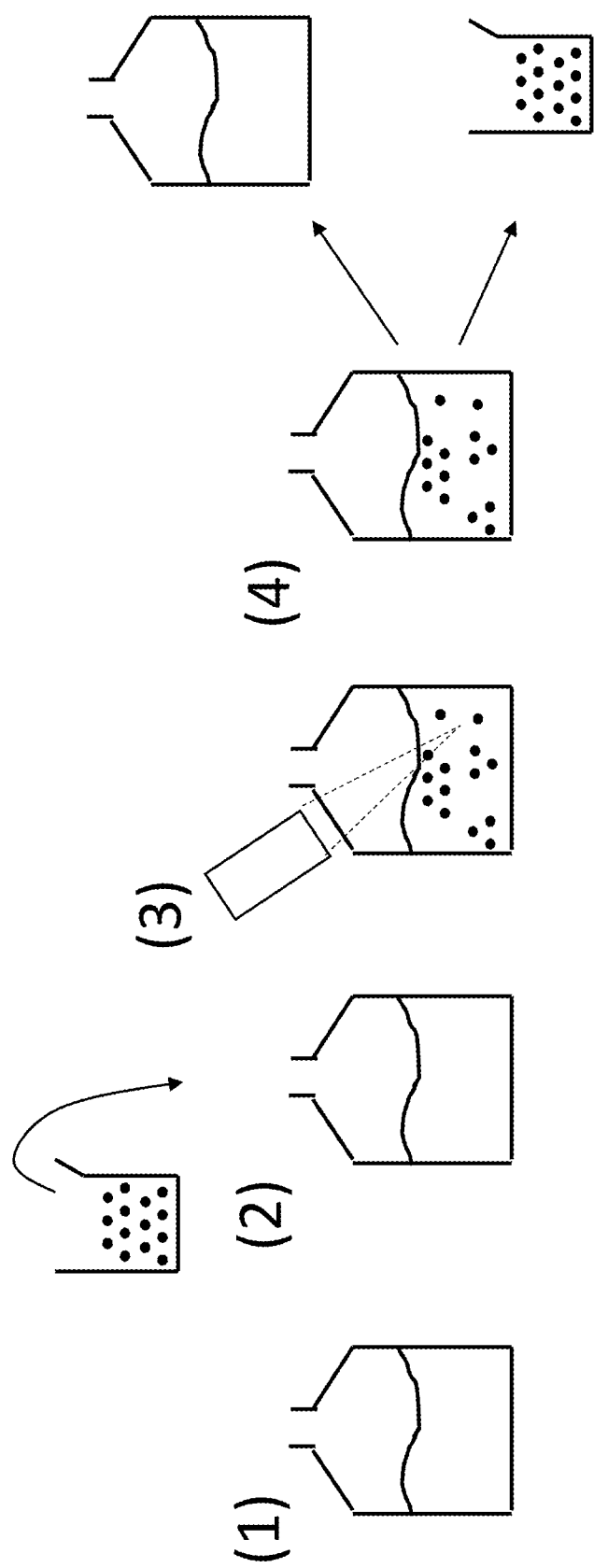

FIG. 11 illustrates the use of a Raman marker for temperature measurement of the analyte.

Figure 12C:
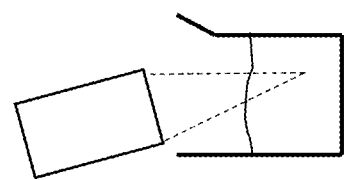
Figure 12B:
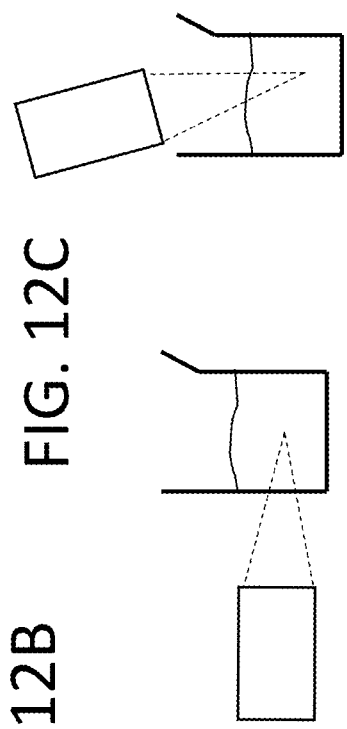
Figure 12E:
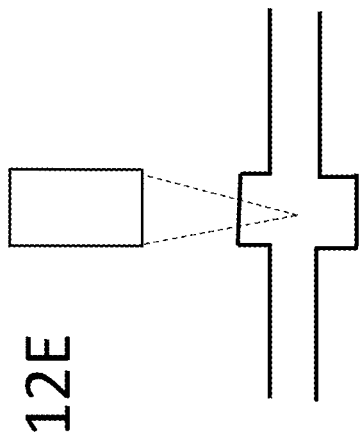
Figure 12A:
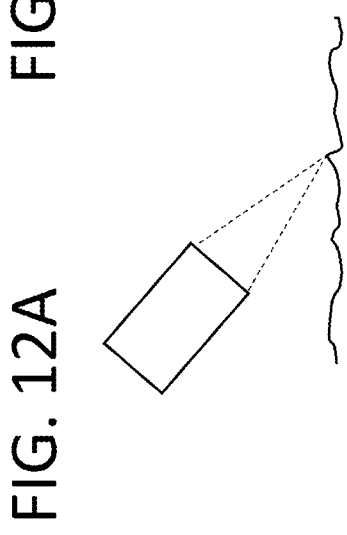
Figure 12D:
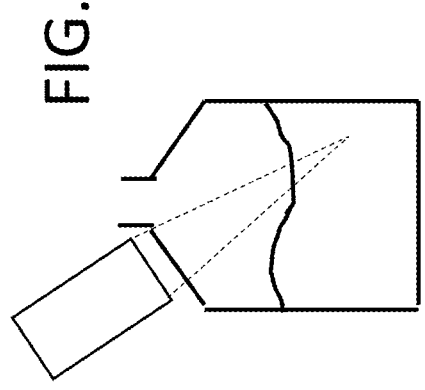

FIGS. 12A-12E is a collection of schematics representing different measurement conditions for a standoff Raman analyzer, or other laser-based, standoff spectrometers, including standoff measurements in: FIG. 12A—a solid sample; FIG. 12B—a liquid in a container through the container wall; FIG. 12C—a liquid in a container through a container opening; FIG. 12D—an analyte in a reactor; and FIG. 12E—an analyte in a flow cell.

Figure 13A:
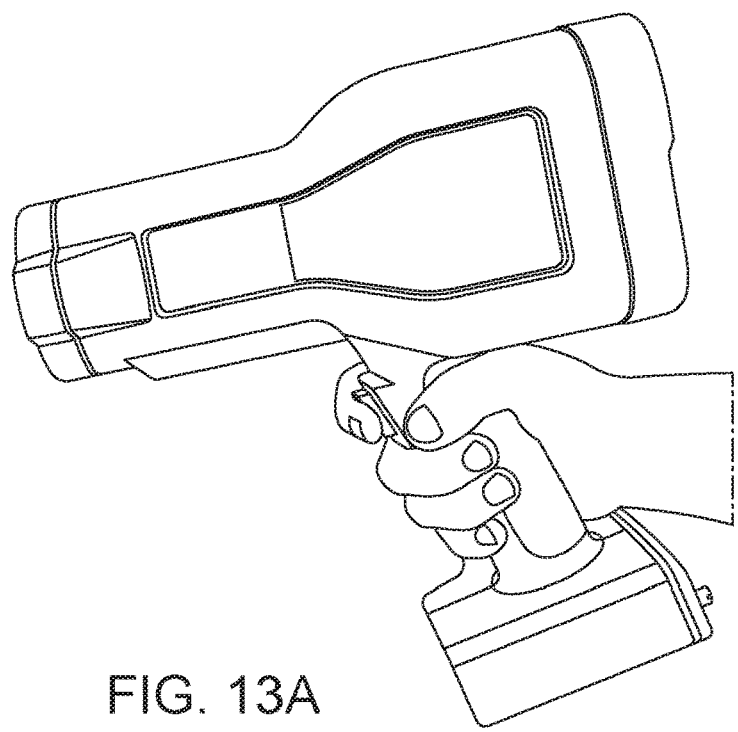

FIG. 13A is a photograph of a handheld Raman standoff differential spectroscopy system.

Figure 13B:
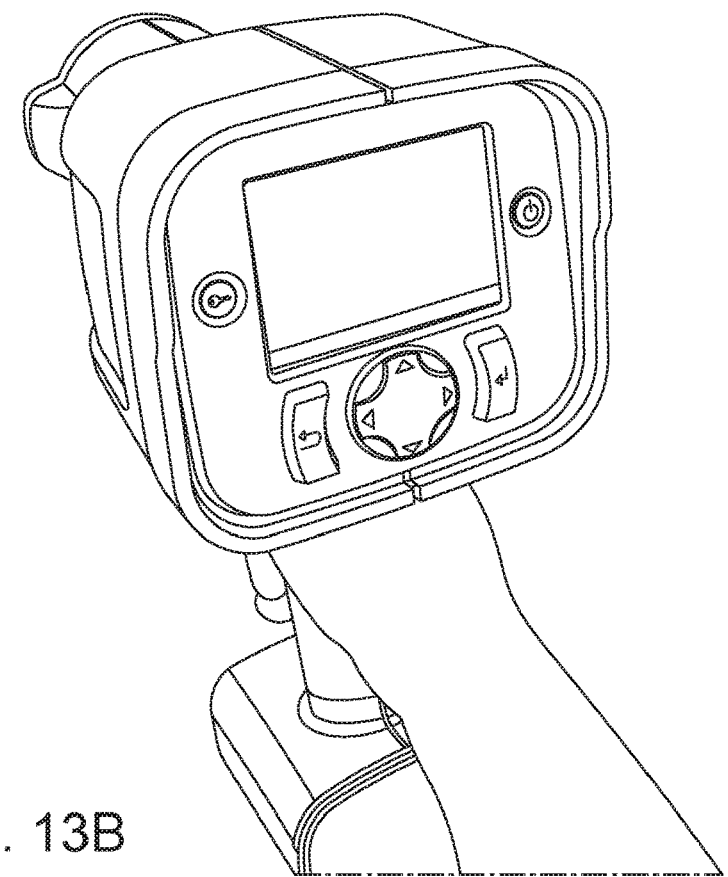

FIG. 13B illustrates a handheld Raman standoff differential spectroscopy system in a measurement setting.

Figure 14:
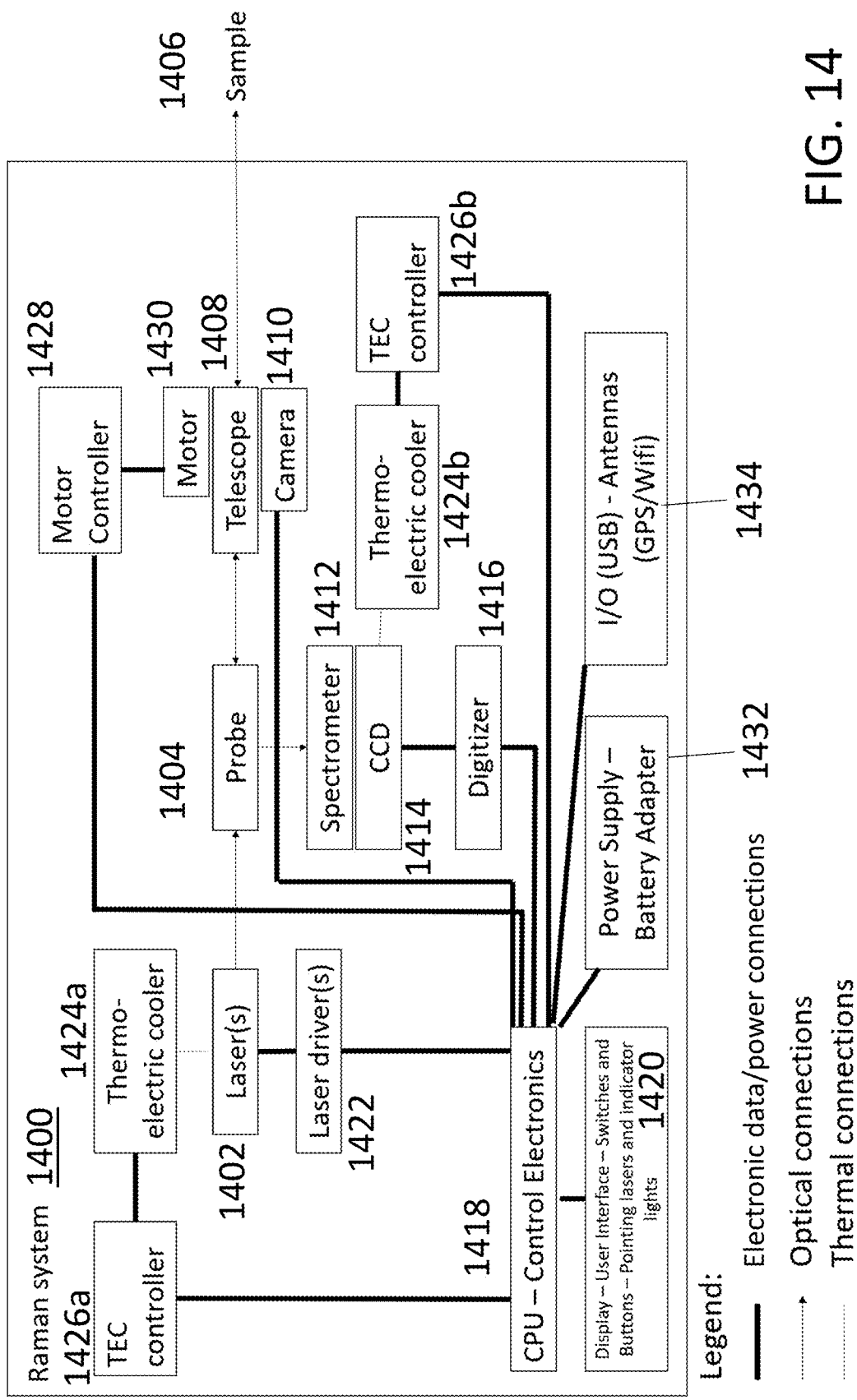

FIG. 14 is a block diagram of an example handheld differential Raman spectroscopy system.

Figure 15:
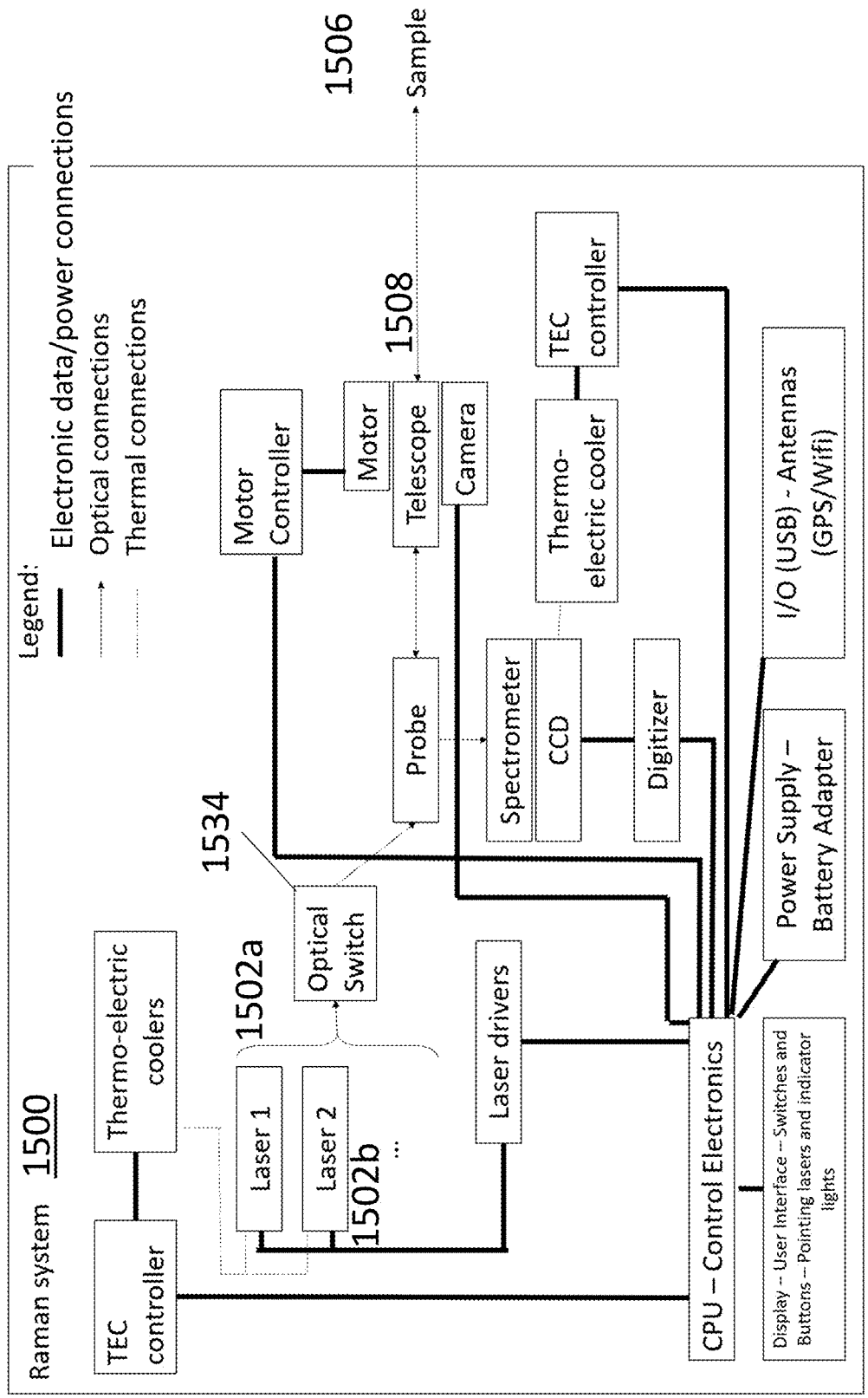

FIG. 15 is a block diagram of a handheld differential Raman spectroscopy system with an optical switch that switches between Raman pump lasers that emit at slightly different wavelengths.

Figure 16:
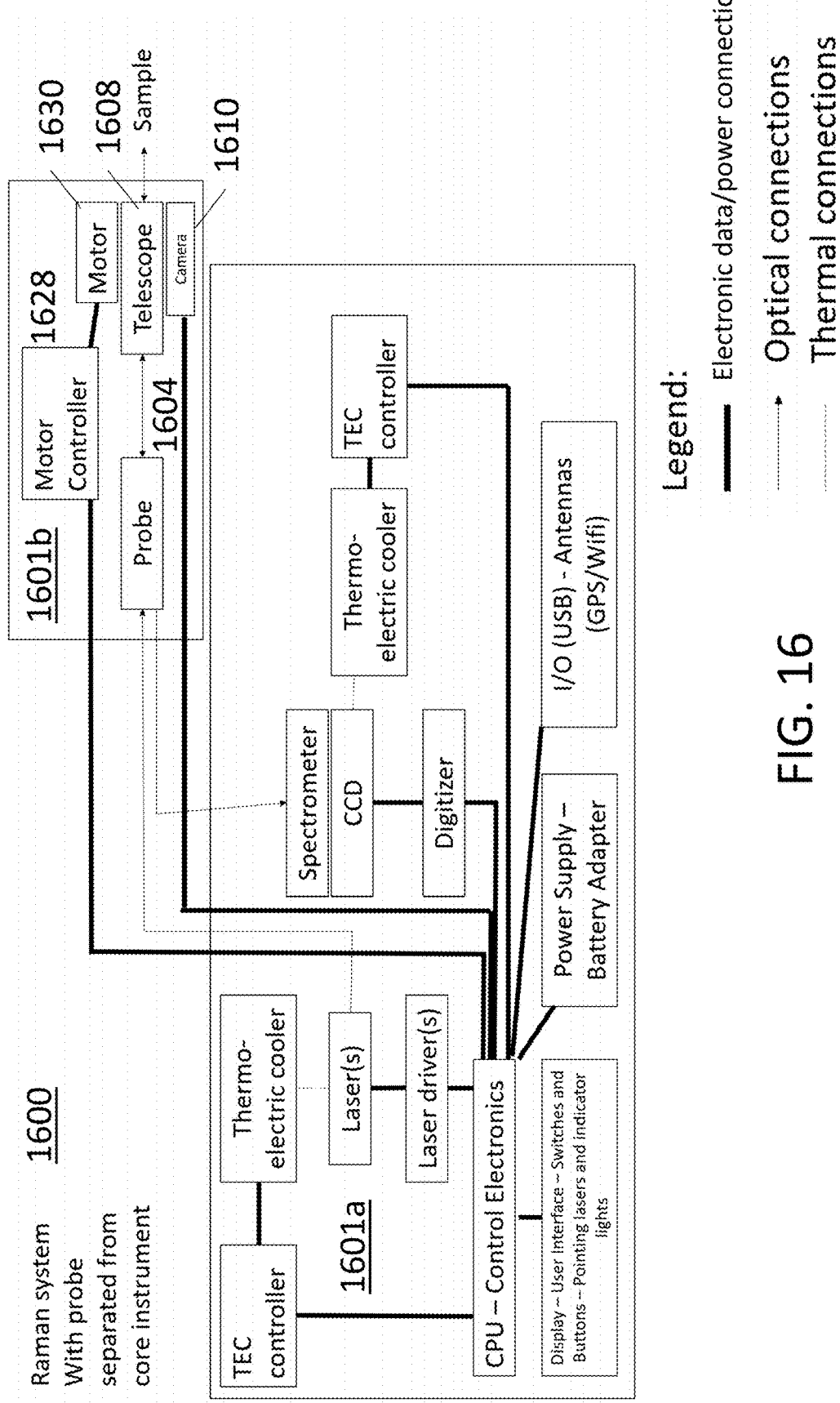

FIG. 16 shows a two-part differential Raman spectroscopy system with a probe module connected to a core module via electrical cable(s) and optical fiber(s).

Figure 17:
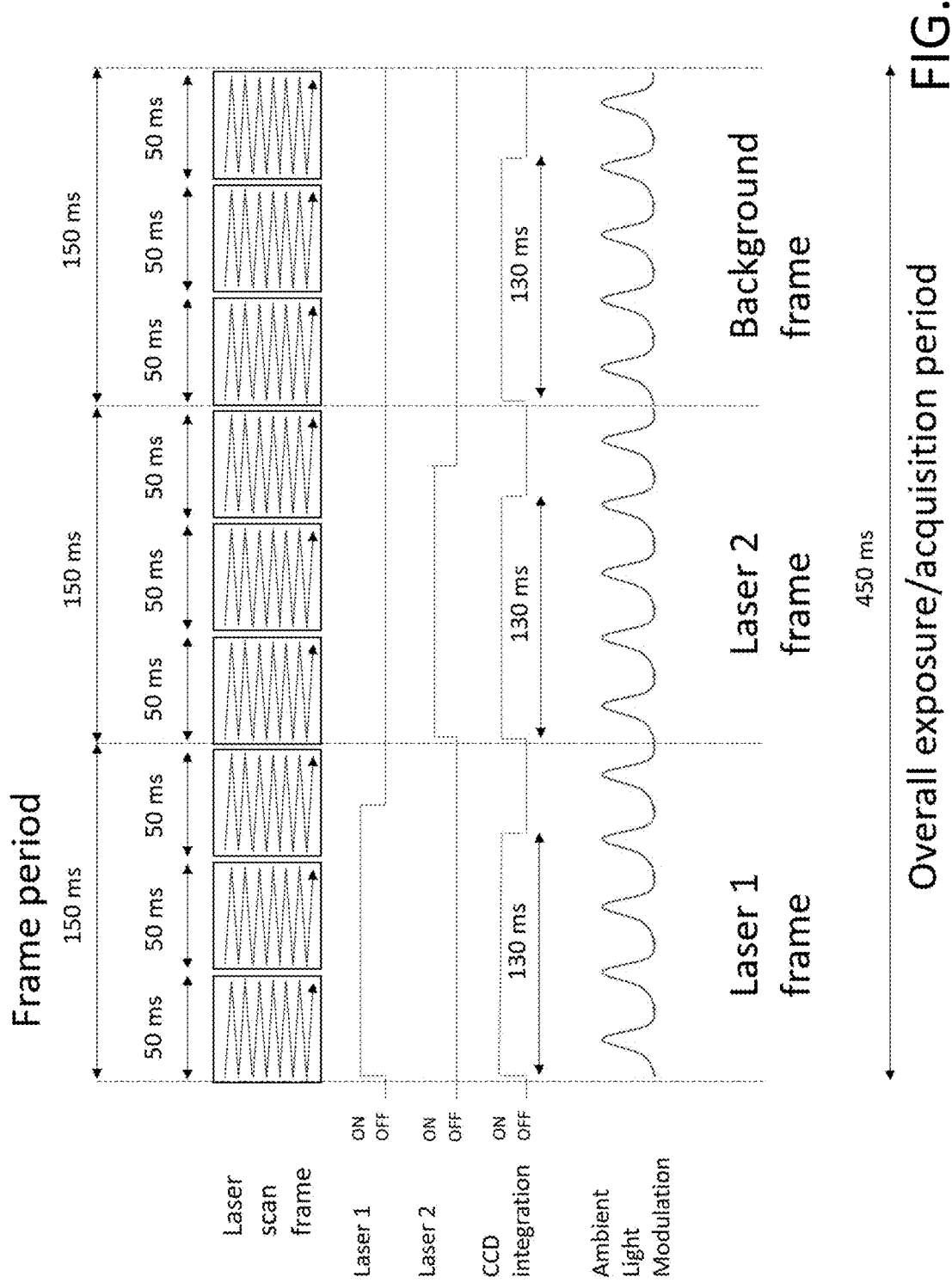

FIG. 17 illustrates the acquisition cycle for differential Raman spectroscopy with frame periods selected based on beam scanning for eye safety/explosion mitigation and ambient light modulation.

FIGS. 18A and 18B illustrate the use of visible laser beams to mark the Raman pump beam's focus in a Raman spectroscopy system, with FIG. 18A illustrating a first position of the movable lens, and FIG. 18B illustrates a second position of the movable lens that is different than the first position.

Figure 19:
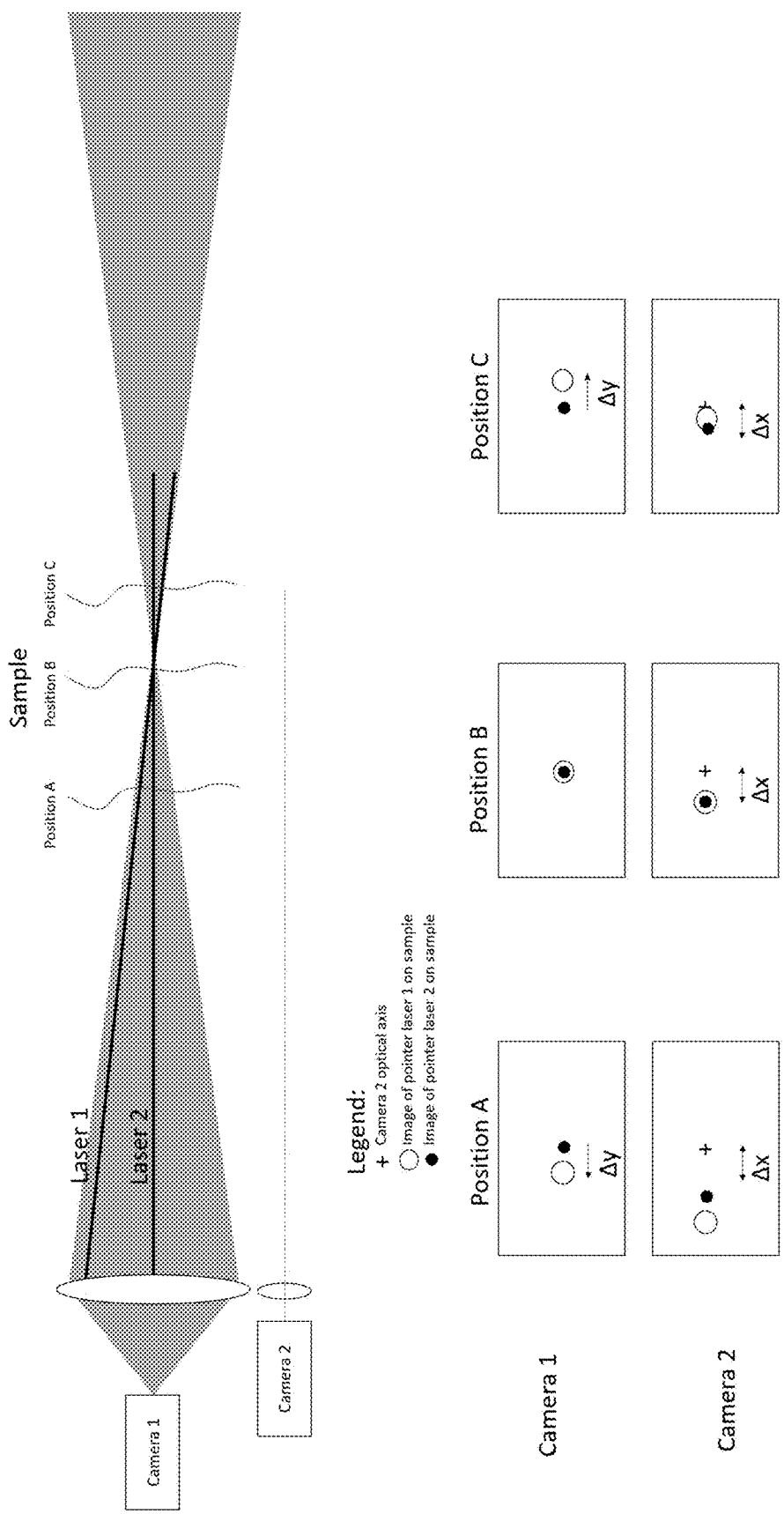

FIG. 19 illustrates the use of a camera system for imaging and tracking a standoff Raman system's aim point.

Figure 20:
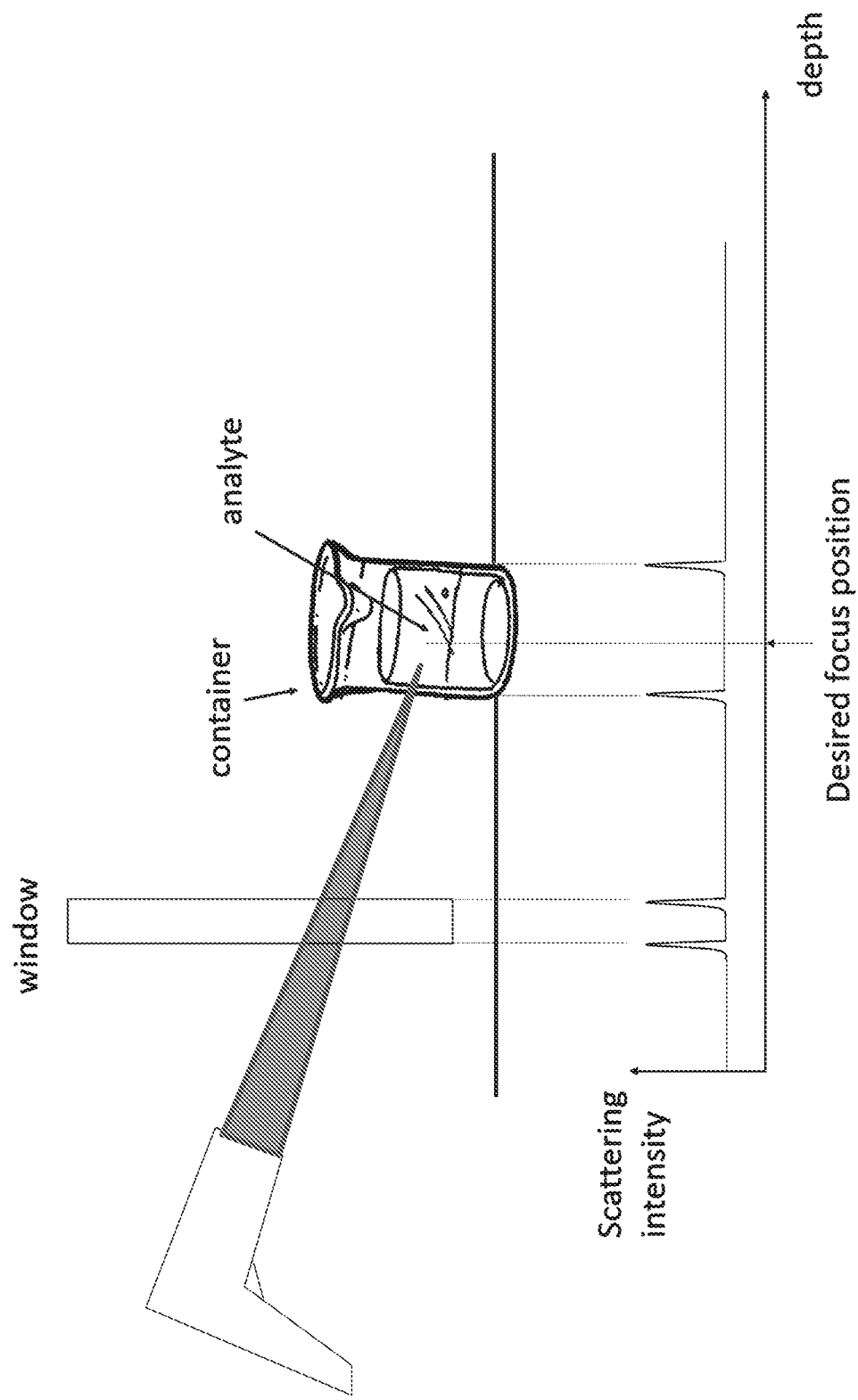

FIG. 20 illustrates focusing a Raman pump beam through obstructions (e.g., a window and a beaker wall) with a handheld standoff differential Raman spectroscopy system.

Figure 21:
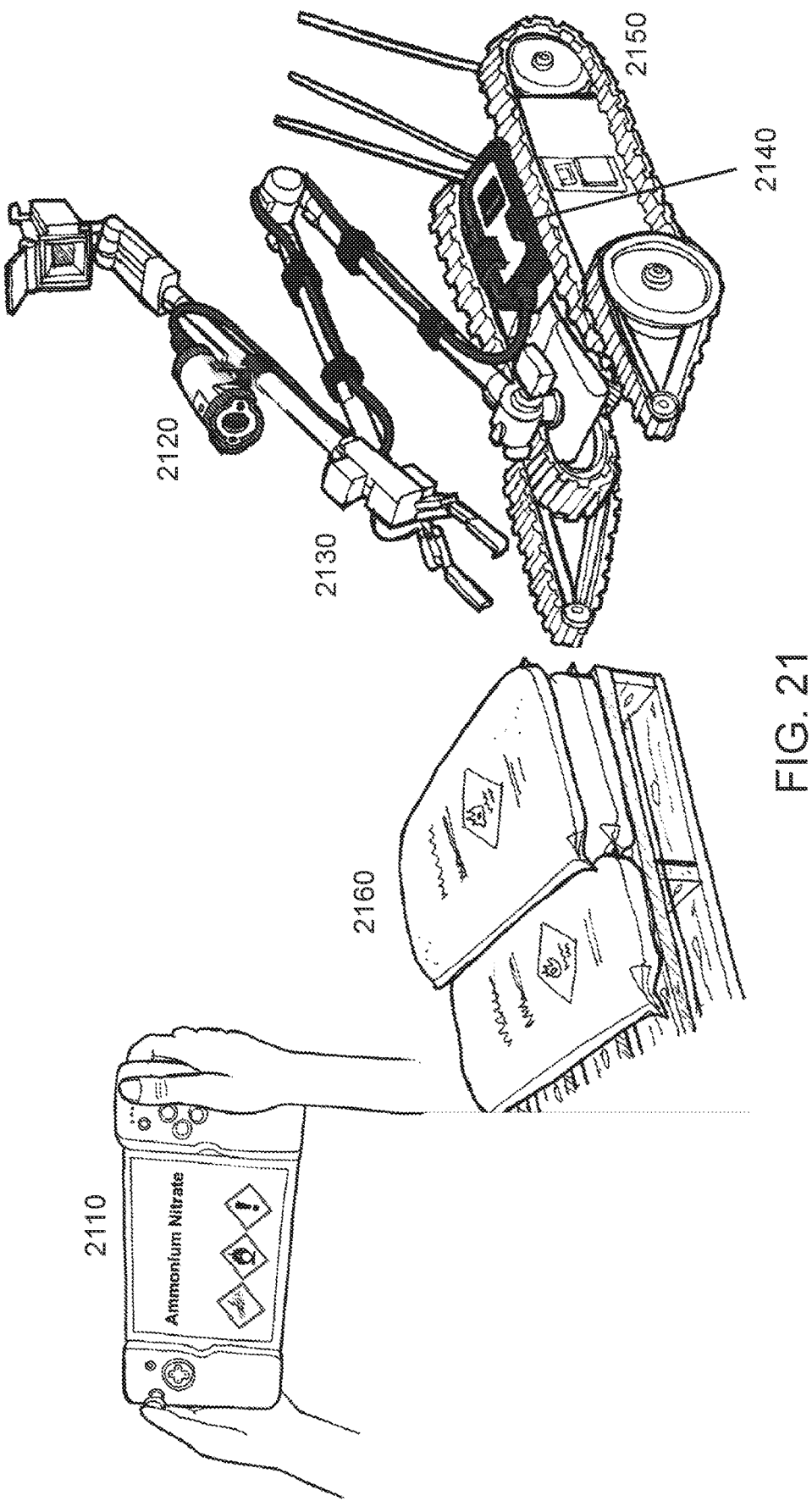

FIG. 21 illustrates a two-part standoff differential Raman spectroscopy system used with a robot.

Figure 22:
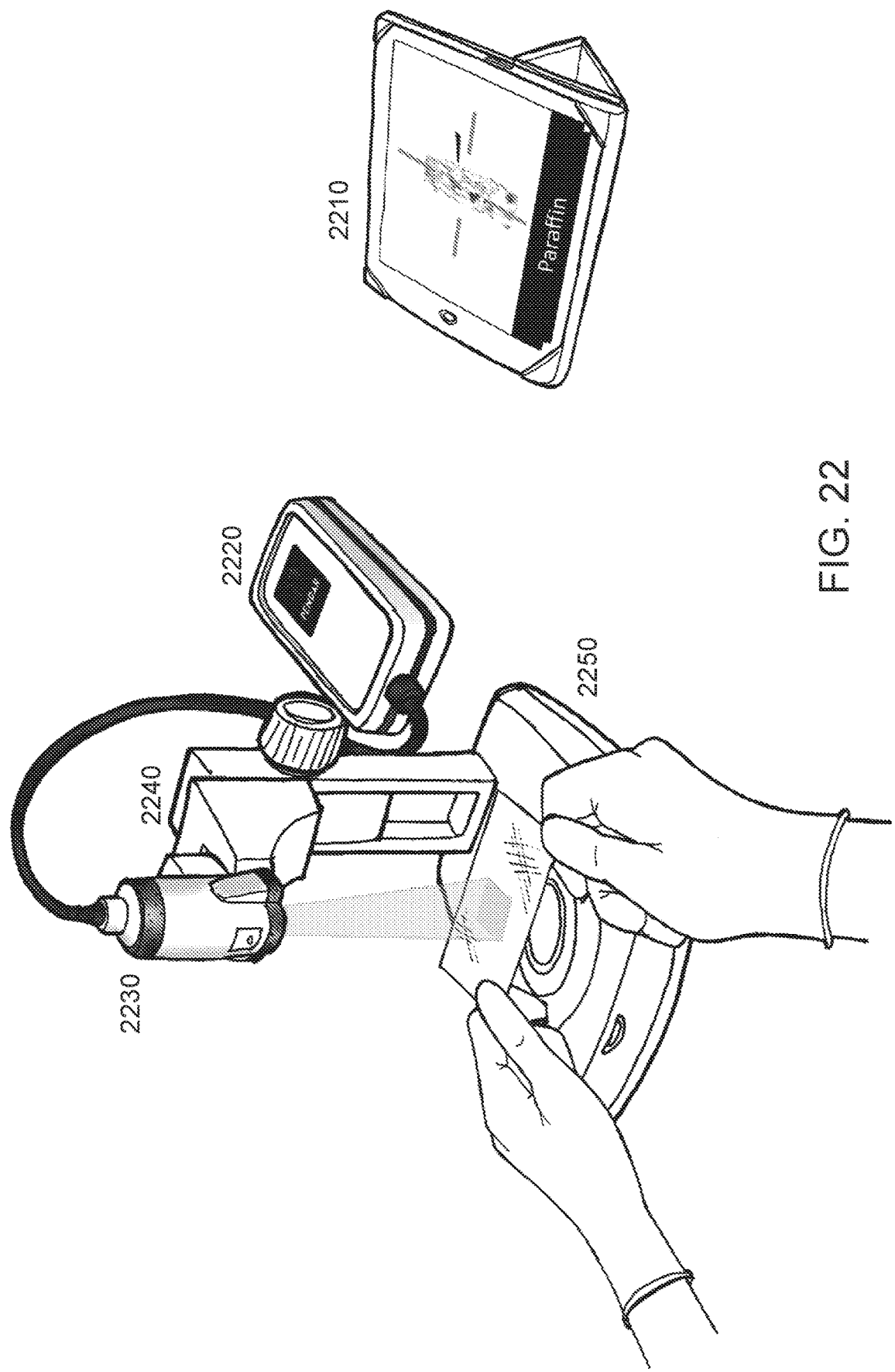

FIG. 22 illustrates a two-part standoff differential Raman spectroscopy system used in a laboratory to measure a sample in or on a slide.

Figure 23:
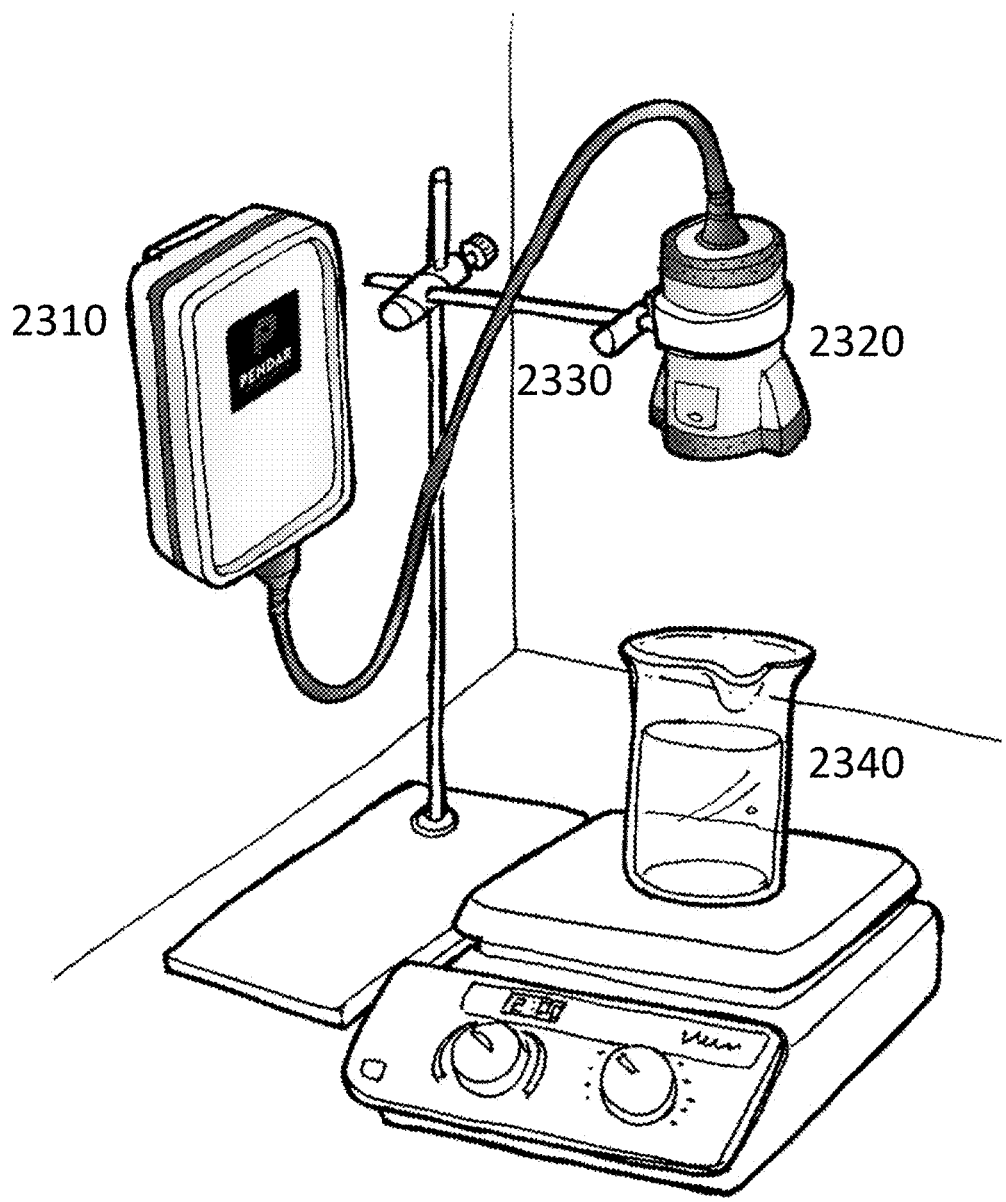

FIG. 23 illustrates a two-part standoff differential Raman spectroscopy system used in a laboratory to measure a liquid sample in a glass container.

Figure 24:
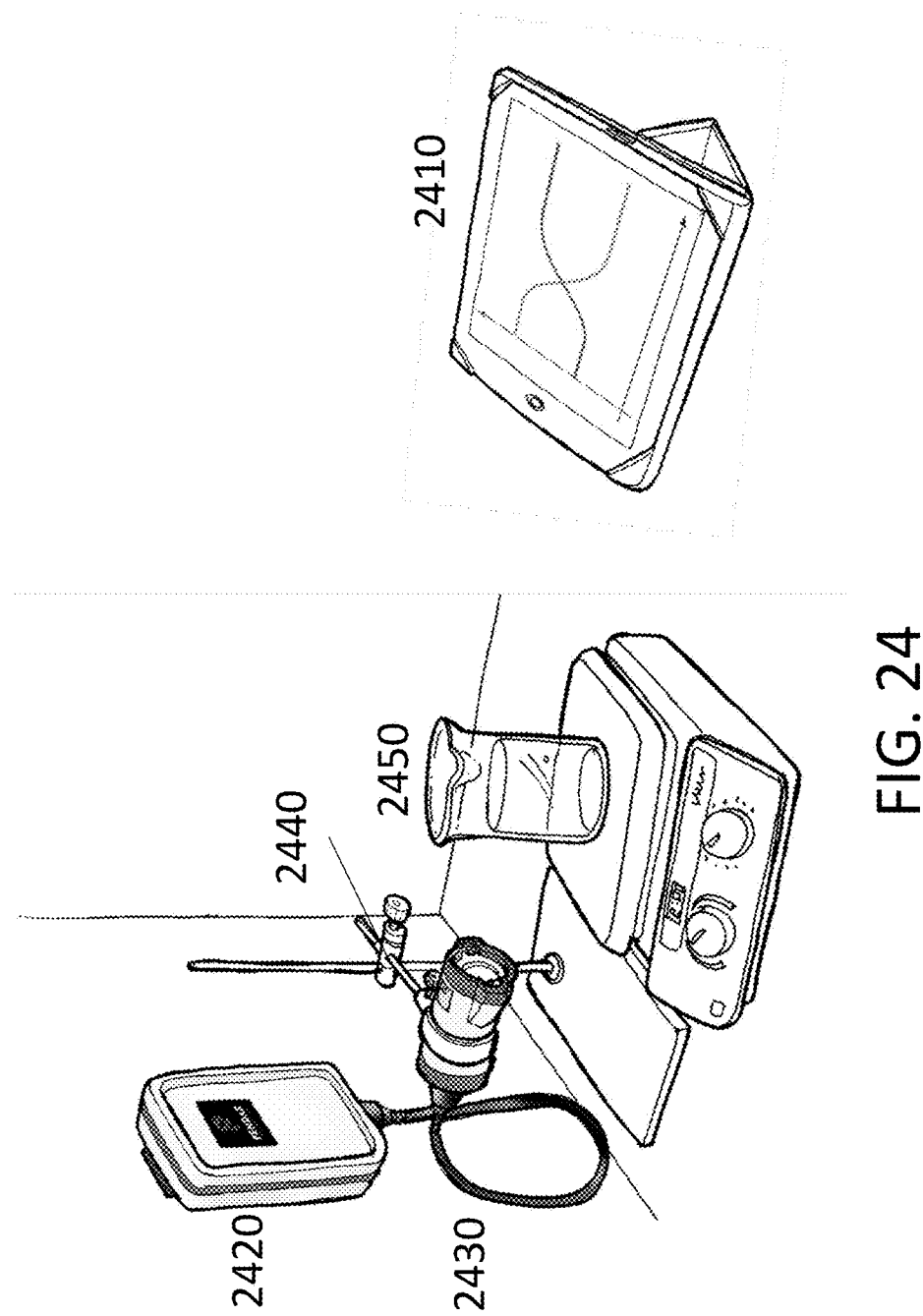

FIG. 24 illustrates a two-part standoff differential Raman spectroscopy system controlled with a wireless controller, with a core module and a probe module mounted on a fixed ring holder to the side of a sample in a beaker.

Figure 25B:
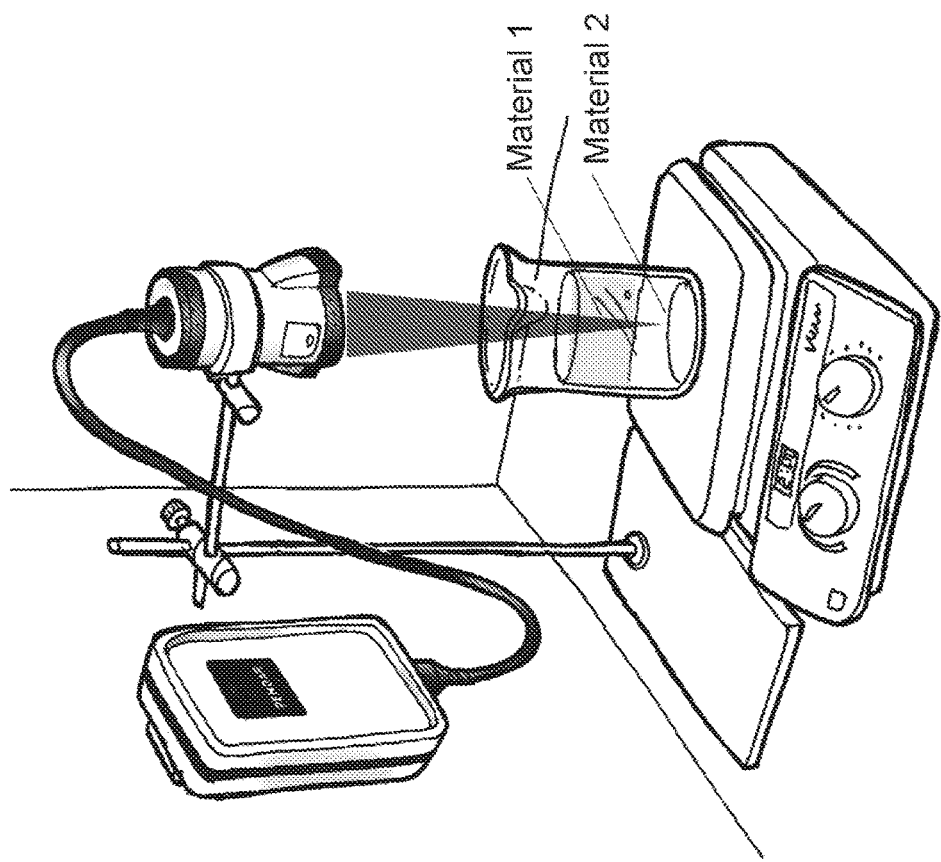
Figure 25A:
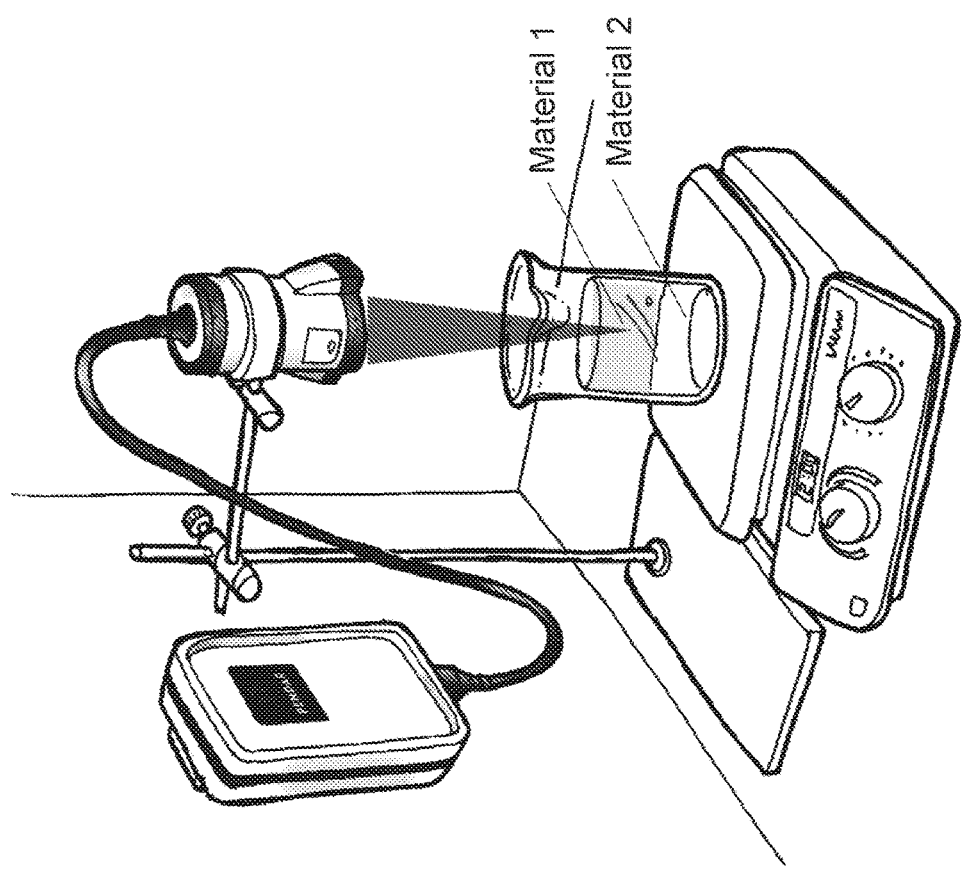

FIGS. 25A and 25B illustrate a two-part standoff differential Raman spectroscopy system measuring, from above, a first working distance/depth in a liquid sample and a second working distance/depth in the liquid sample, respectively.

Figure 26A:
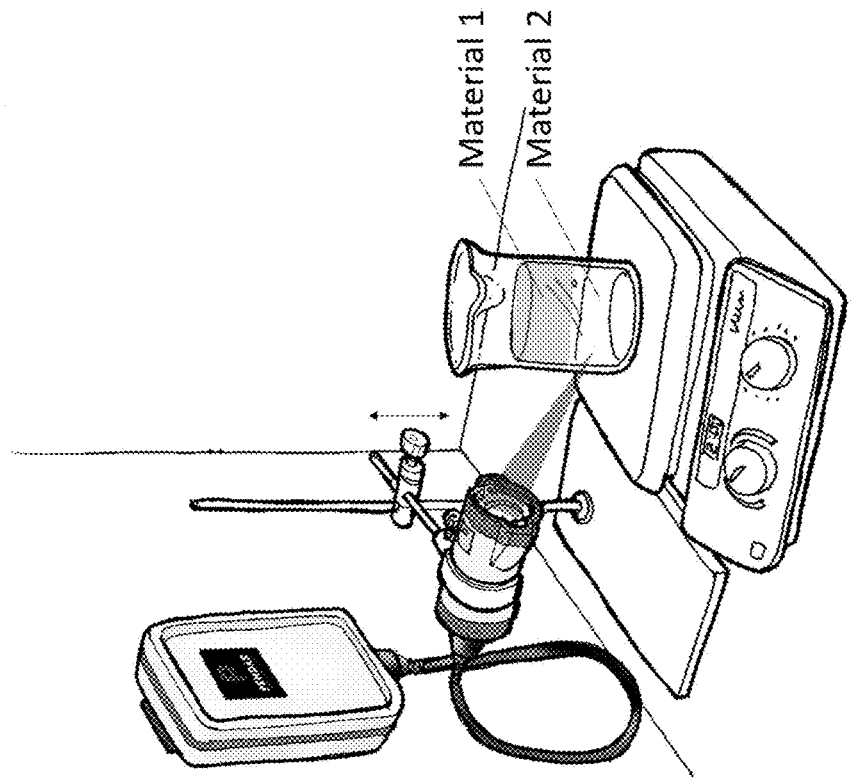
Figure 26B:
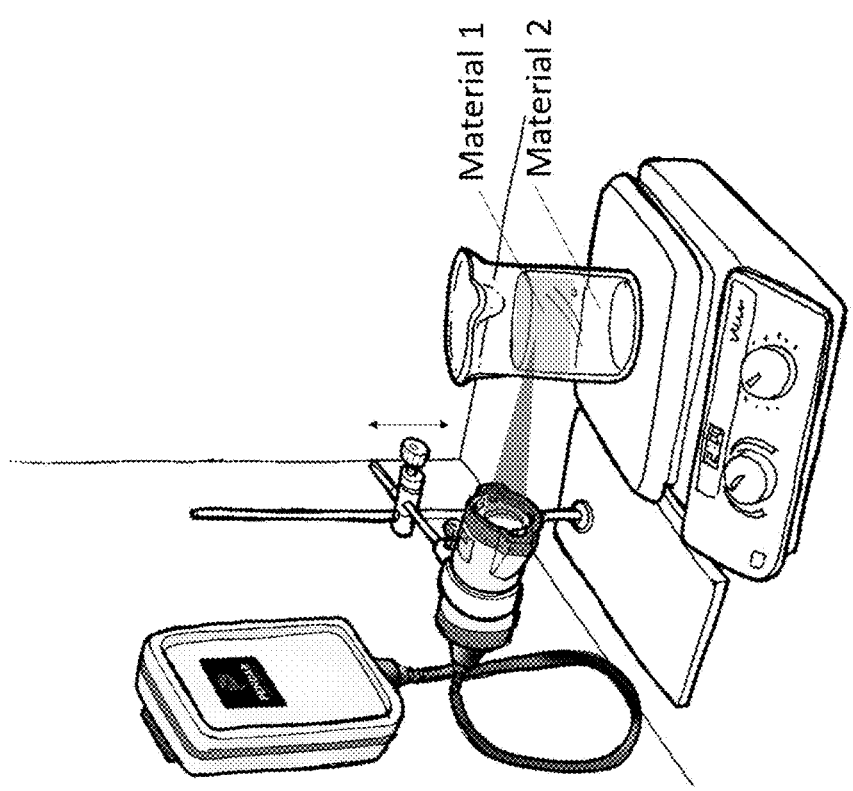

FIGS. 26A and 26B illustrate a two-part standoff differential Raman spectroscopy system measuring, through the sidewall of a container, a first position in a liquid sample and a second position in the liquid sample, respectively.

Figure 27:
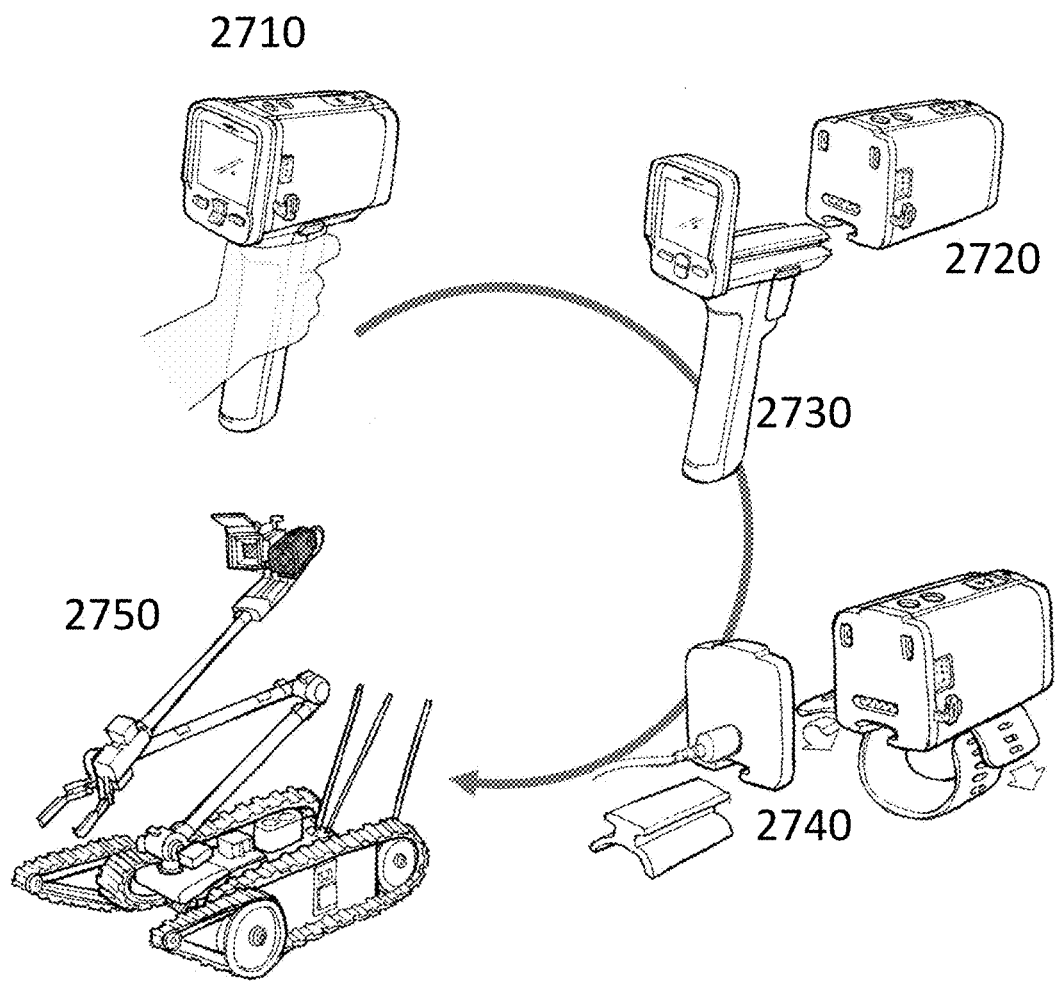

FIG. 27 illustrates a modular standoff differential Raman spectroscopy system.

Figure 28A:
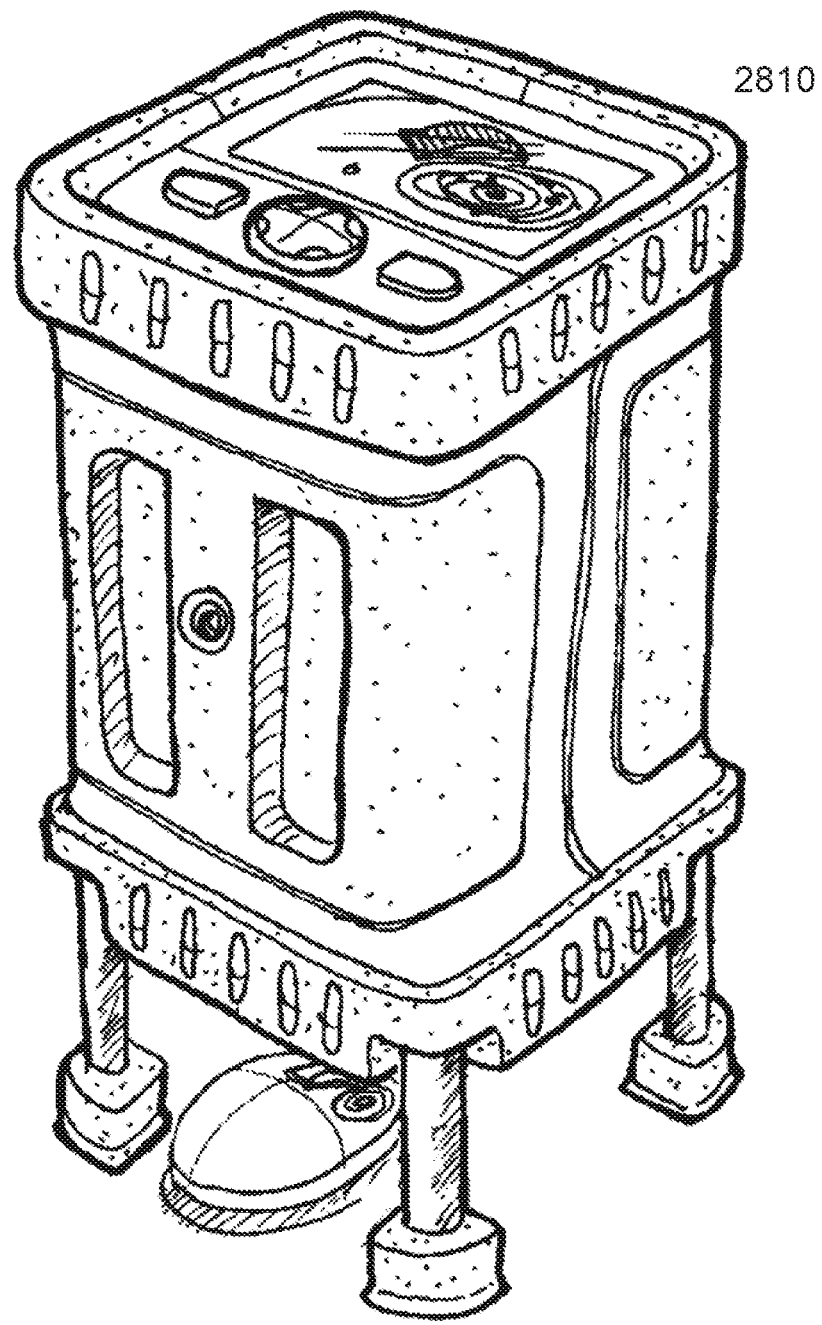

FIG. 28A illustrates a stand-alone Raman macroscope system.

Figure 28B:

FIG. 28B illustrates a tripod-mounted Raman macroscope system.

Figure 28C:
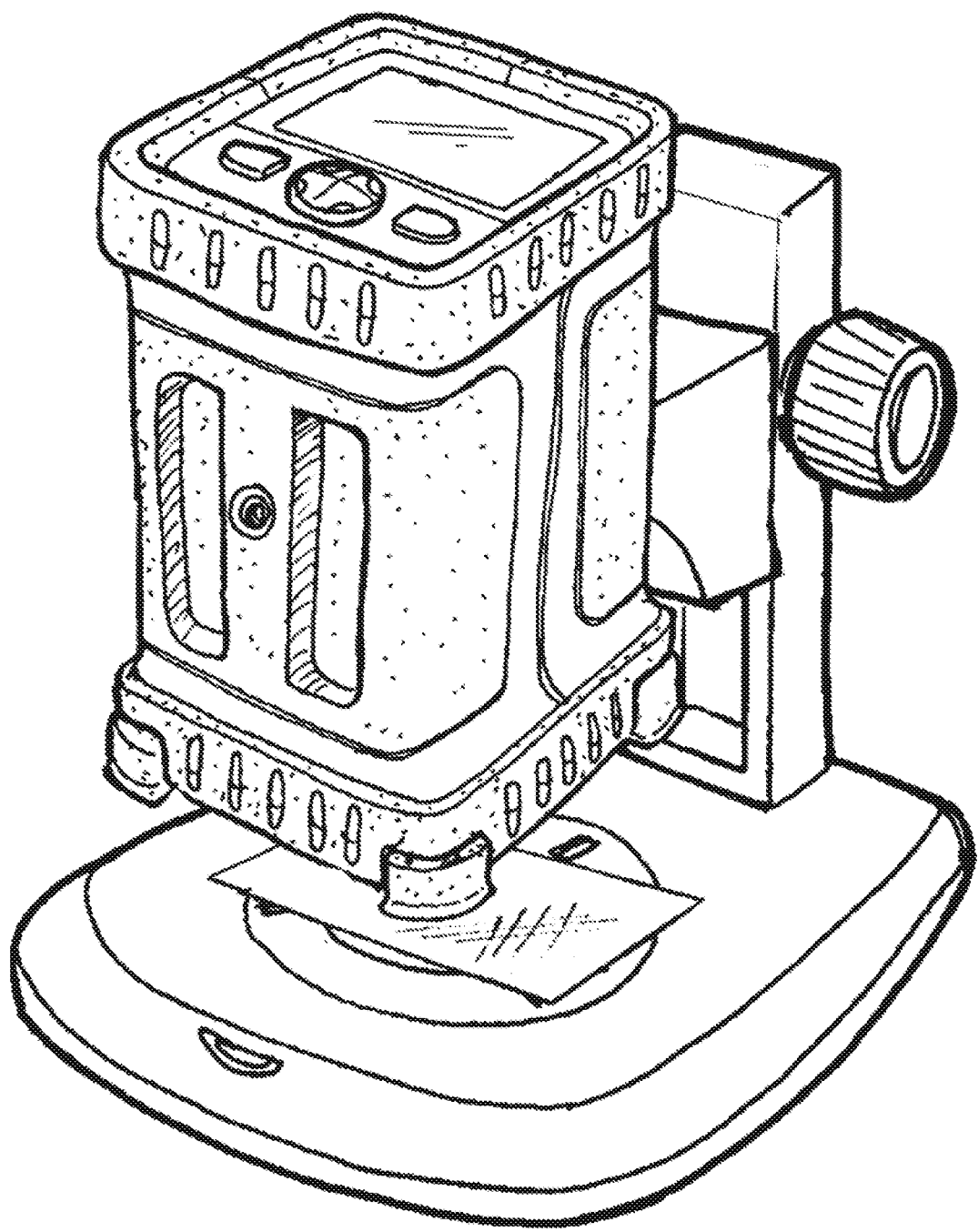

FIG. 28C illustrates a Raman macroscope or stereomicroscope mount with included height adjustment.

Figure 29:
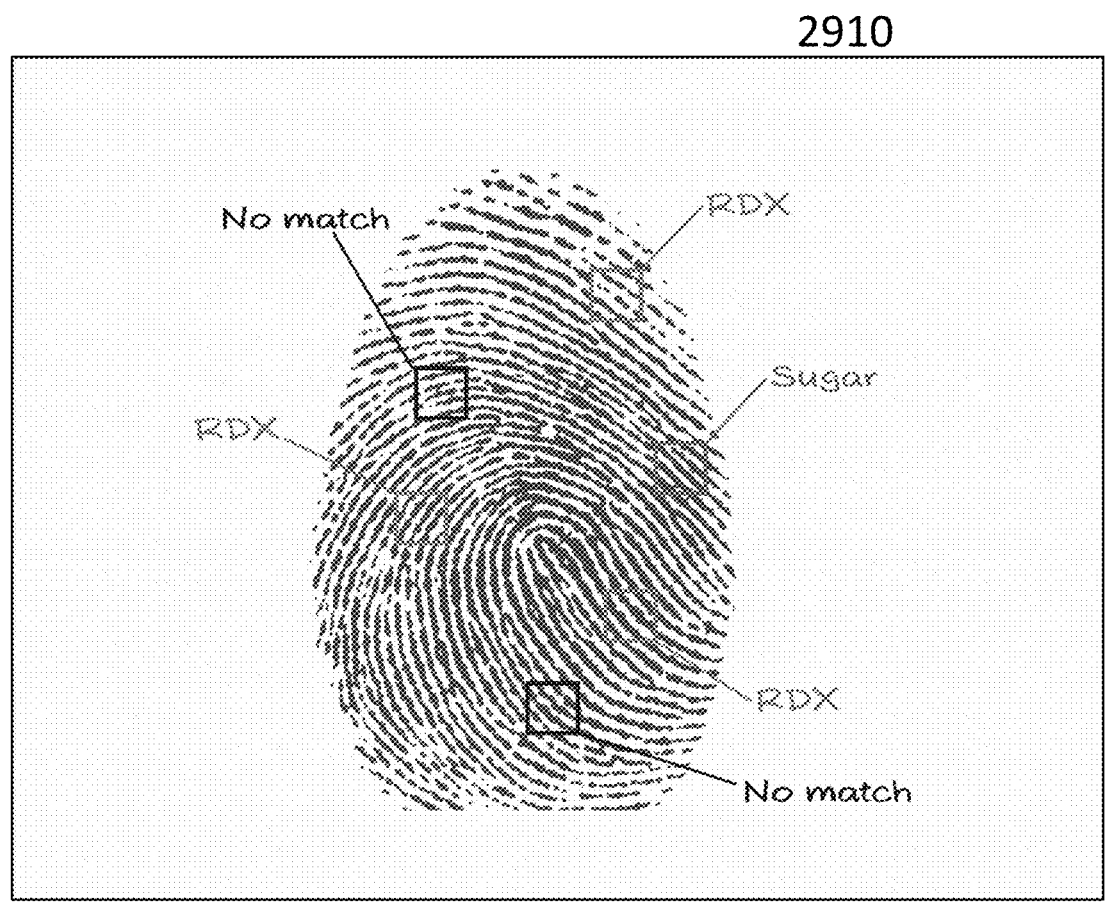

FIG. 29 illustrates a possible result screen.

Figure 30:
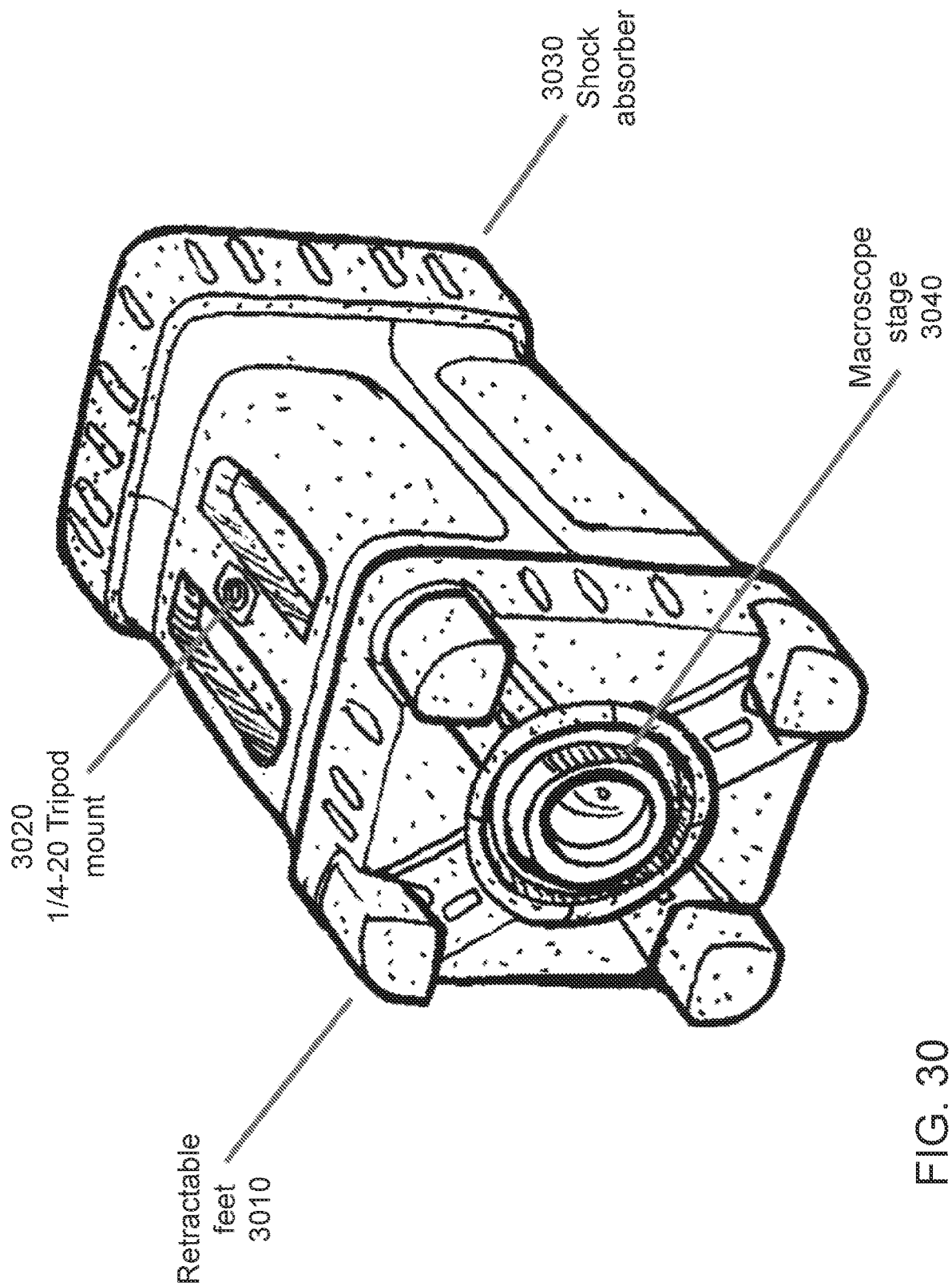

FIG. 30 illustrates several features of the Raman macroscope system.

Figure 31:
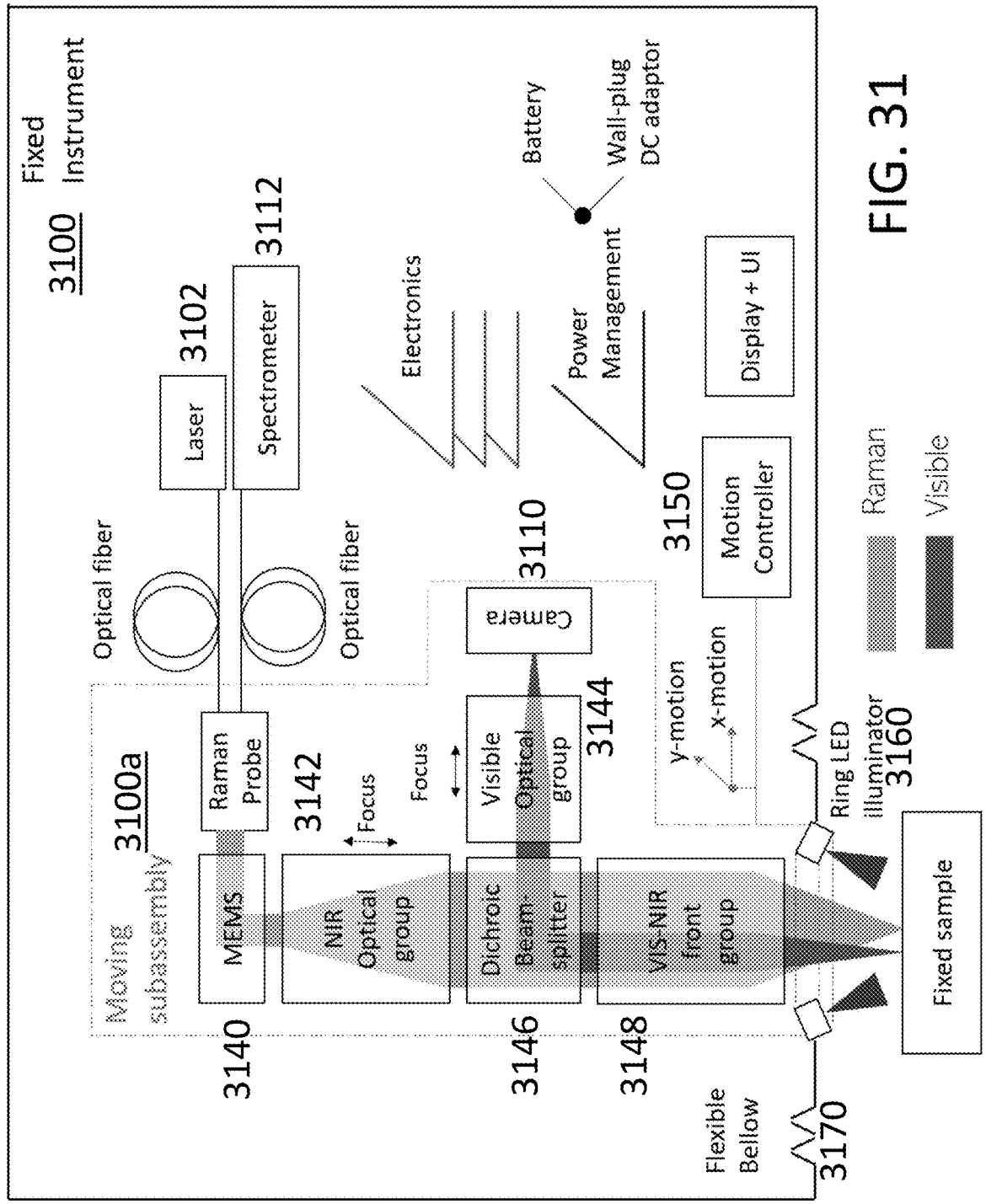

FIG. 31 illustrates a diagram of the Raman macroscope system.

Figure 32:
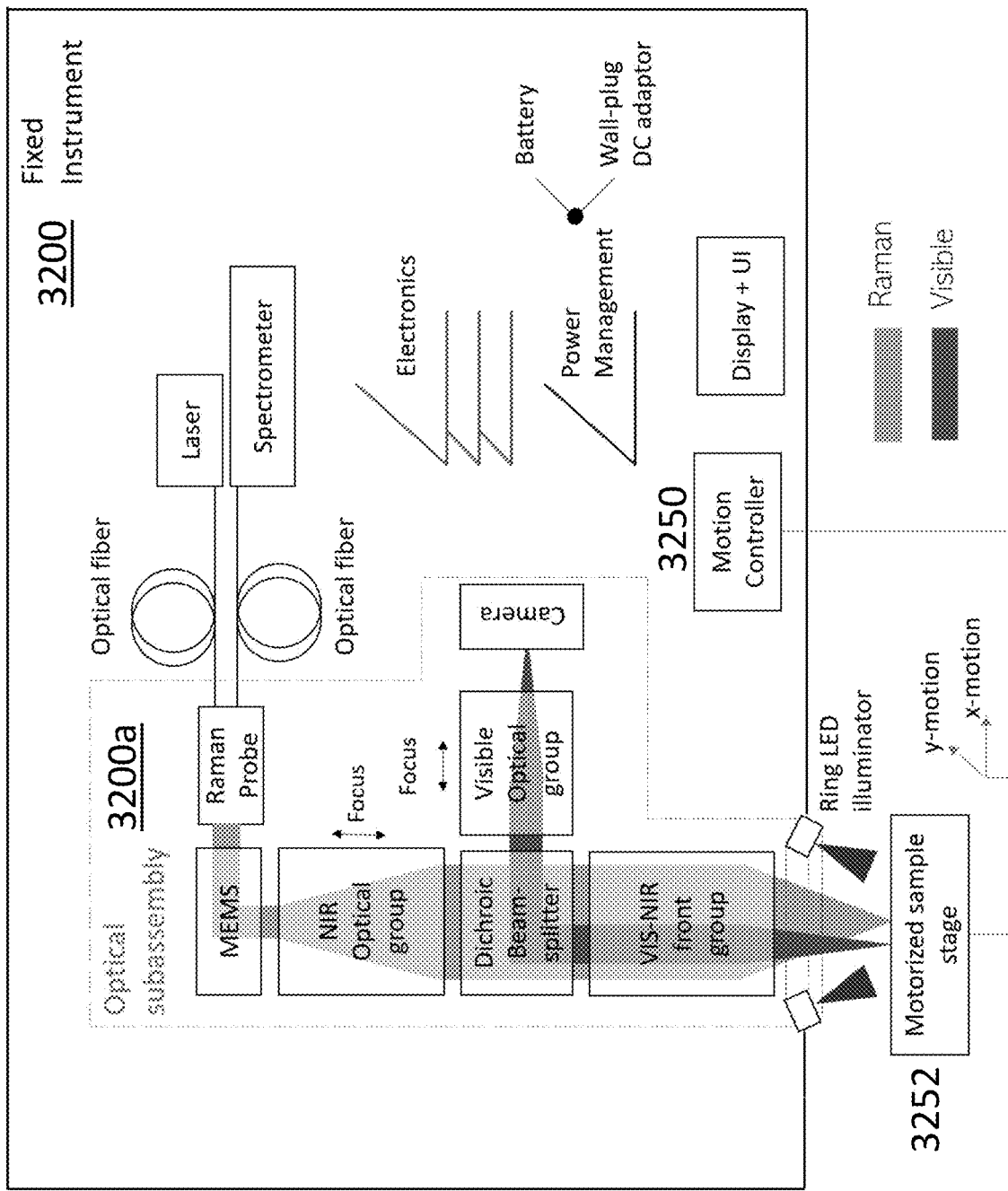

FIG. 32 illustrates a Raman macroscope system similar to the one shown in FIG. 31 with a motorized sample stage.

Figure 33:
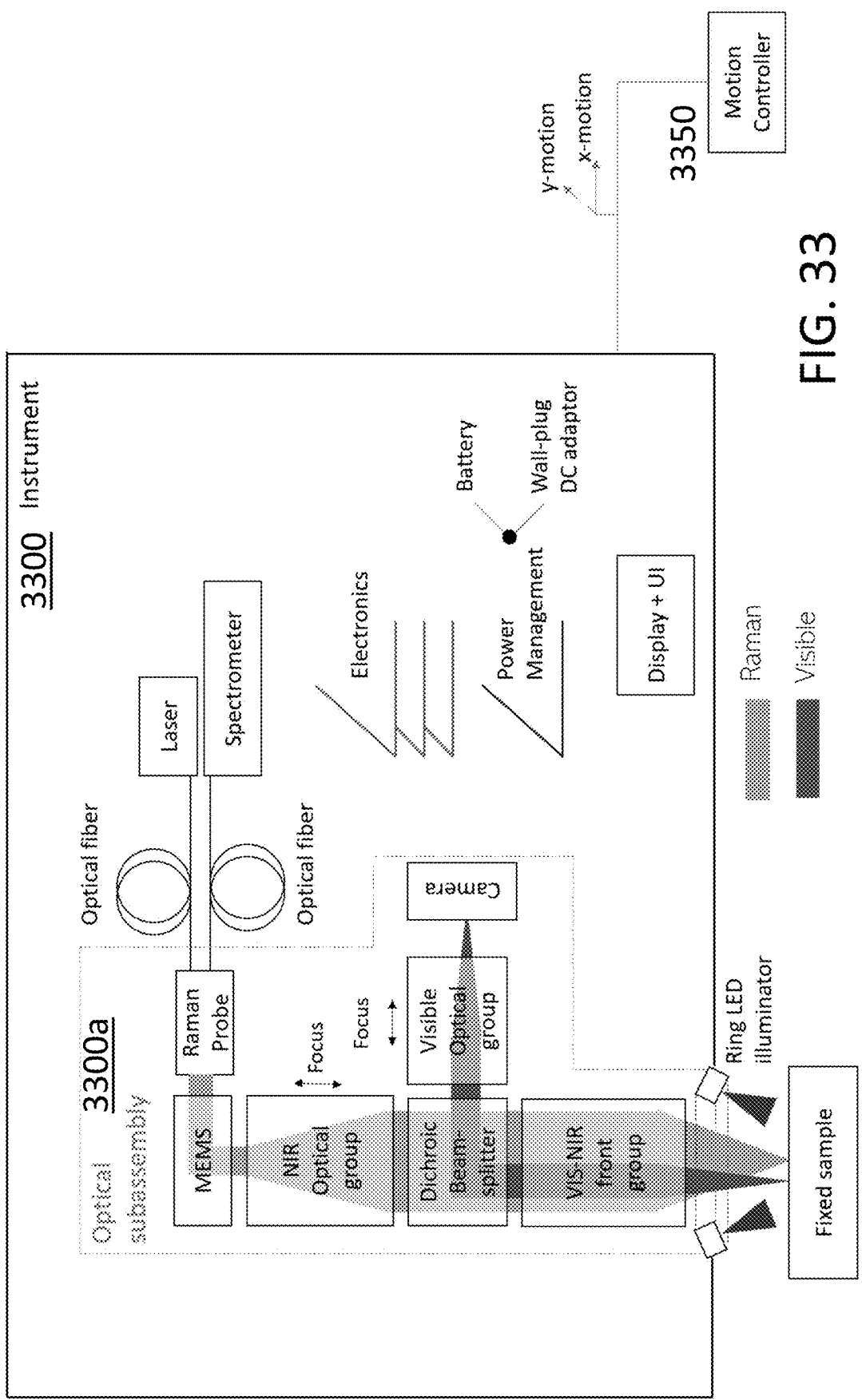

FIG. 33 illustrates a Raman macroscope system similar the one shown in FIG. 31 with the motion controller controlling movement of the entire system.

Figure 34:
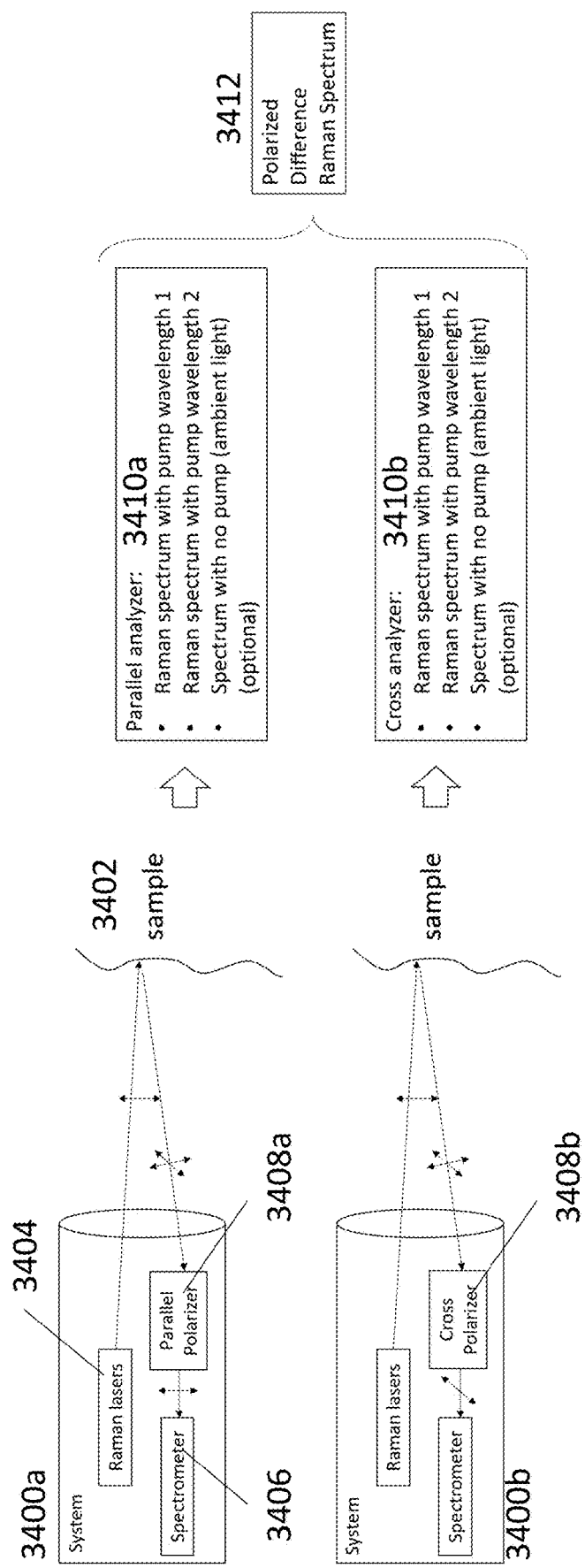

FIG. 34 illustrates acquisition of polarized difference Raman information/spectra.

Figure 35A:
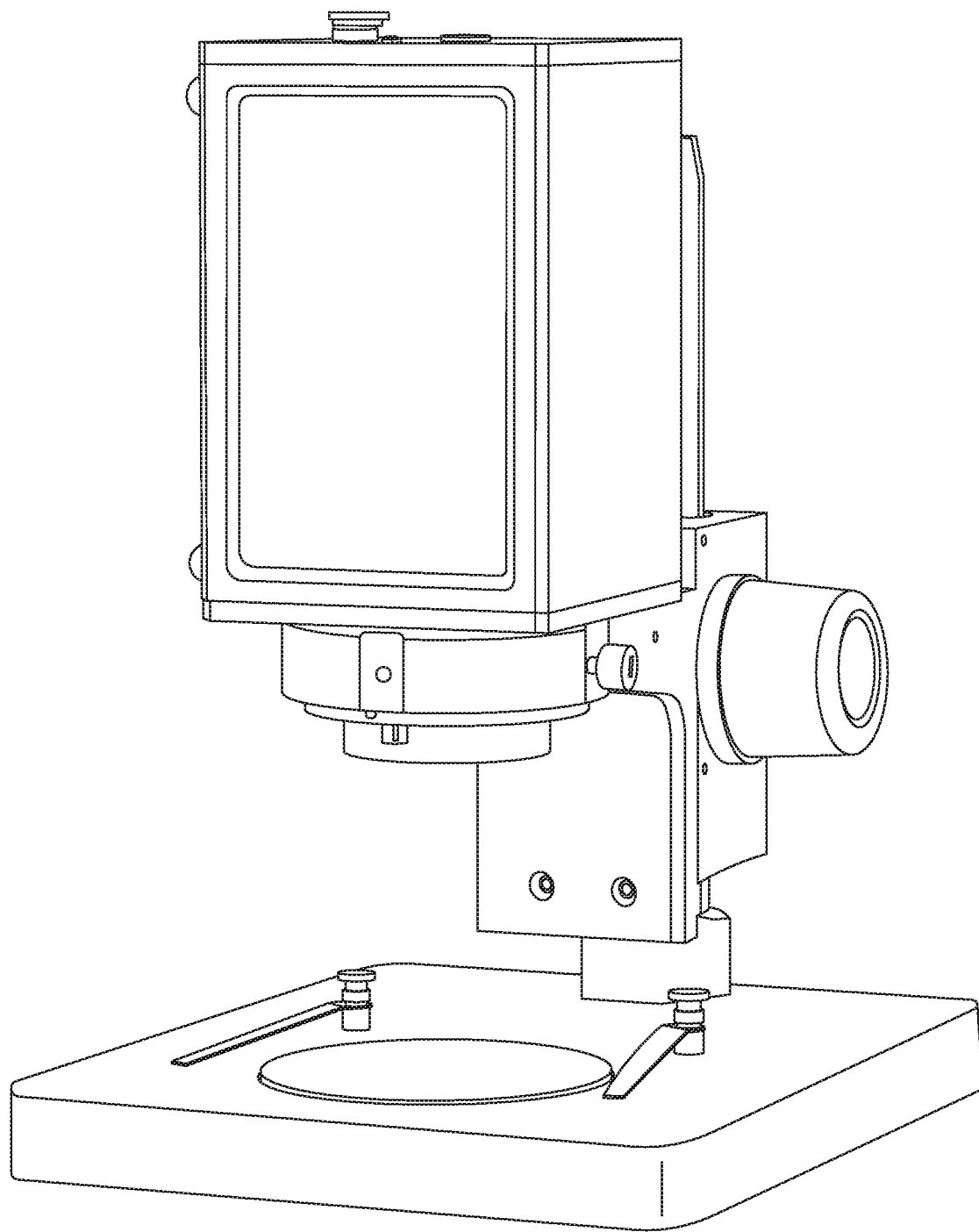

FIG. 35A is a front perspective photograph of a standoff Raman system mounted on a microscope stage.

Figure 35B:
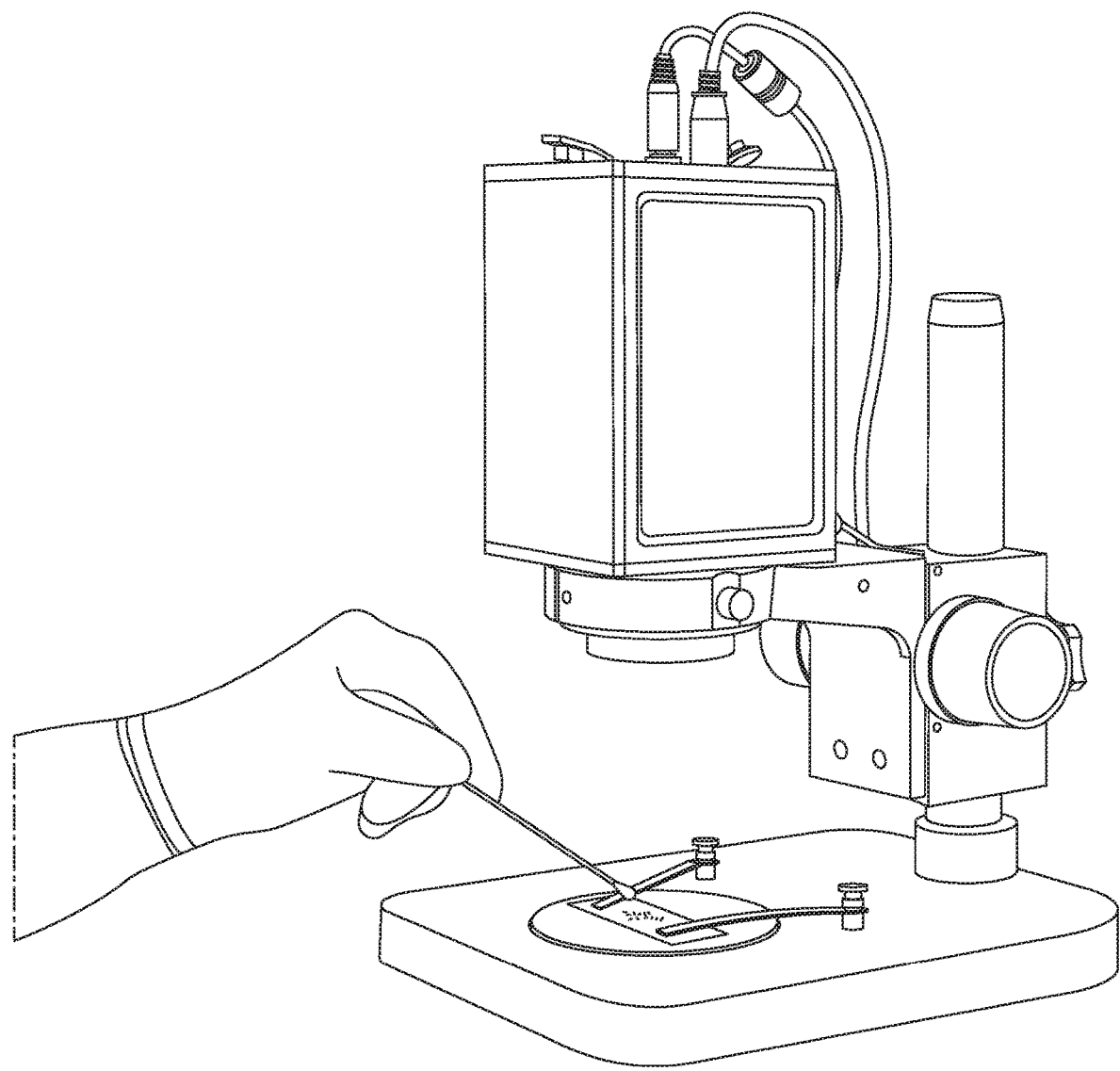

FIG. 35B is a photograph of the standoff Raman system of FIG. 35A during typical use.

Figure 36:
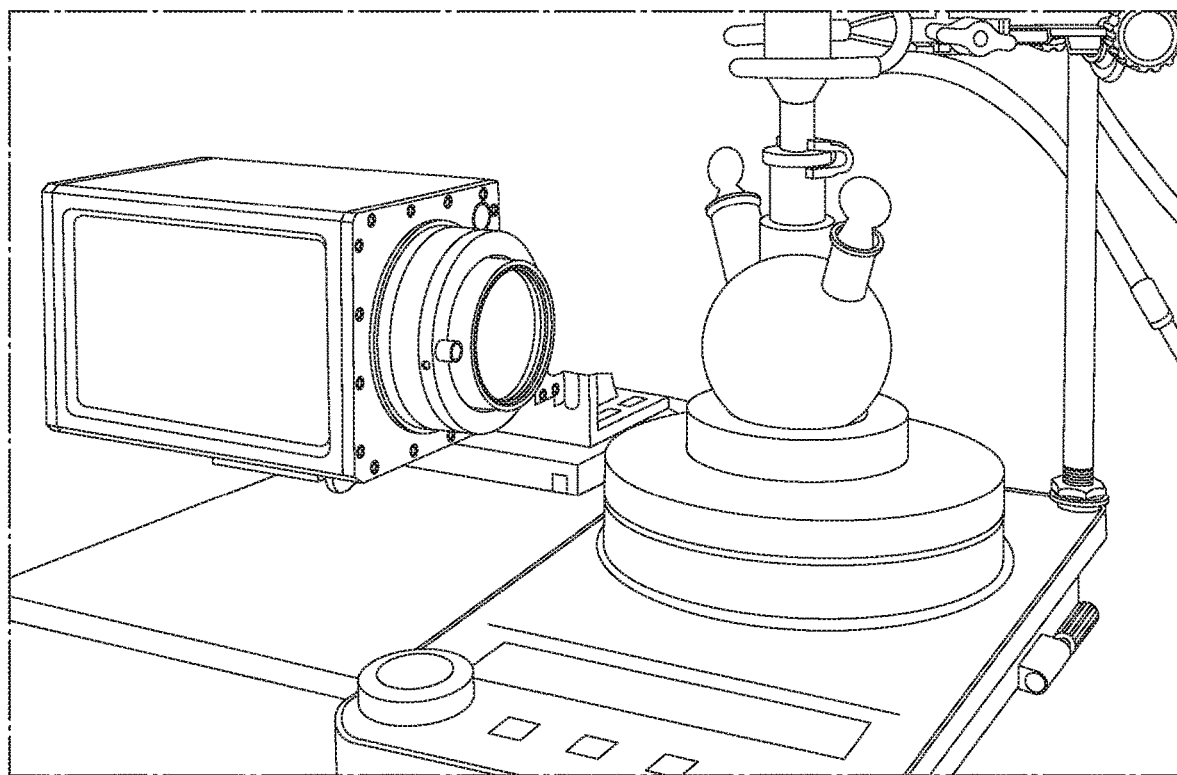

FIG. 36 is a photograph of a standoff Raman system used to monitor a reaction inside a vessel.

Figure 37:
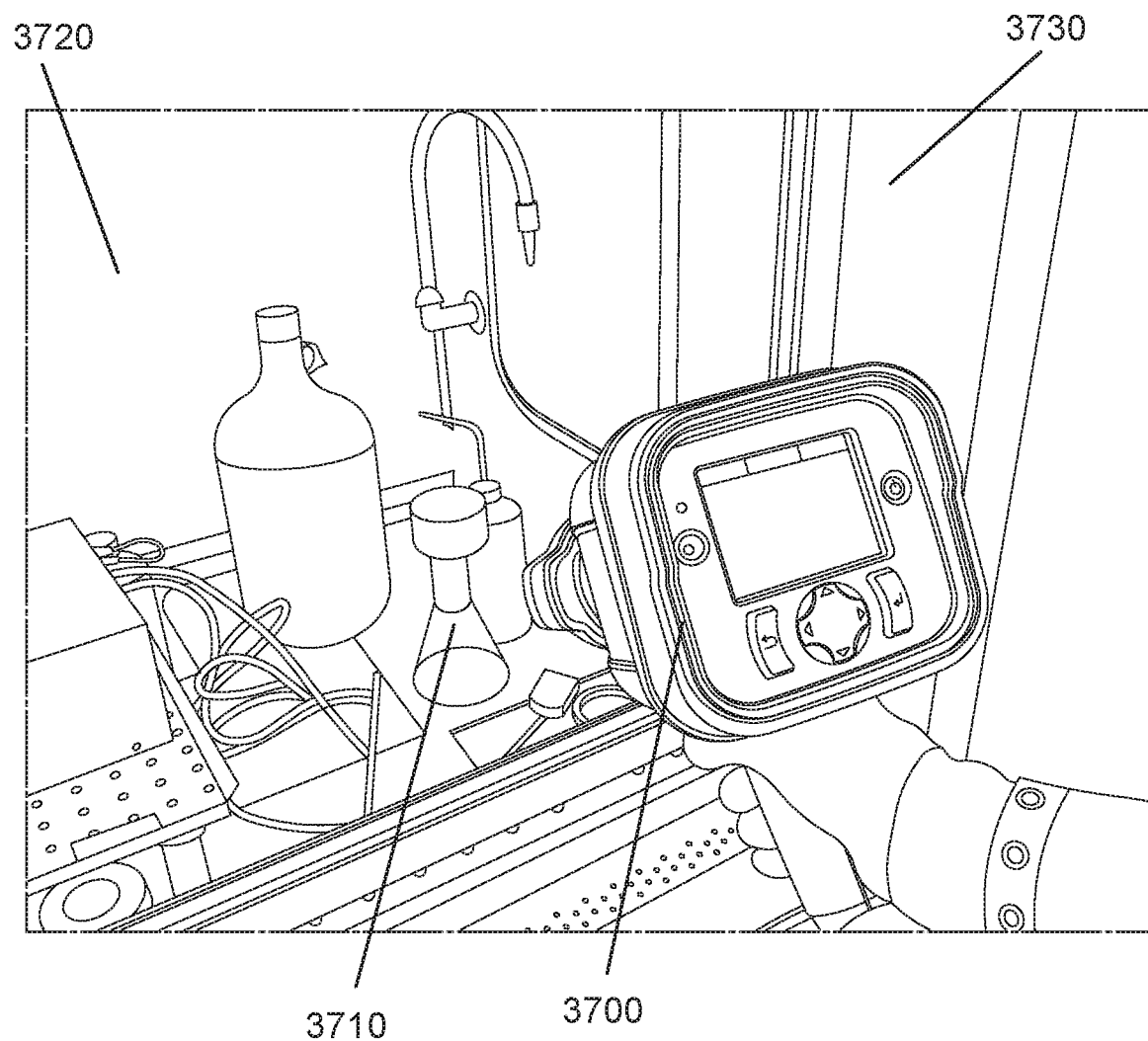

FIG. 37 is a photograph of a handheld standoff Raman system identifying a chemical compound through multiple obstructions.

Figure 38B:
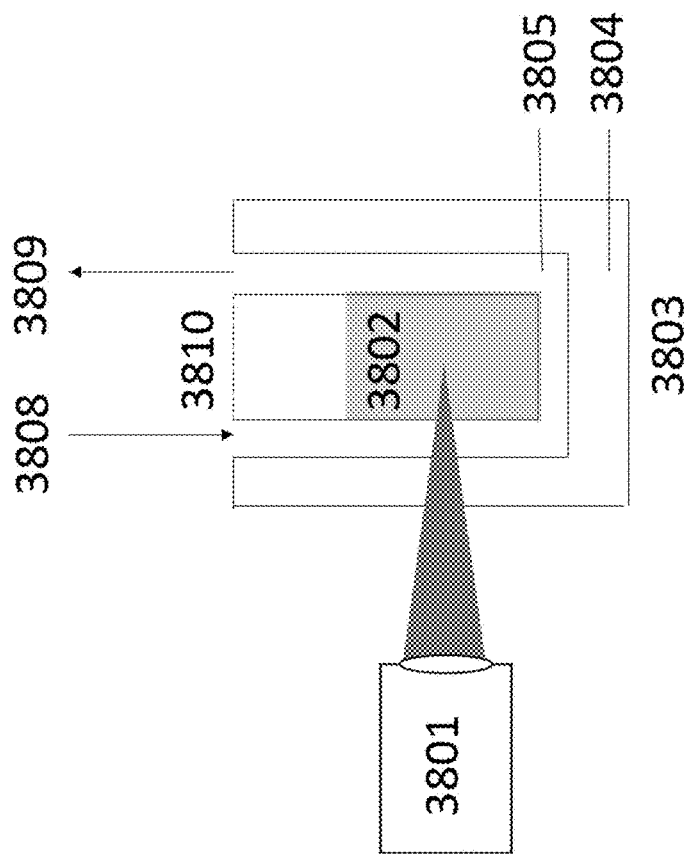
Figure 38A:
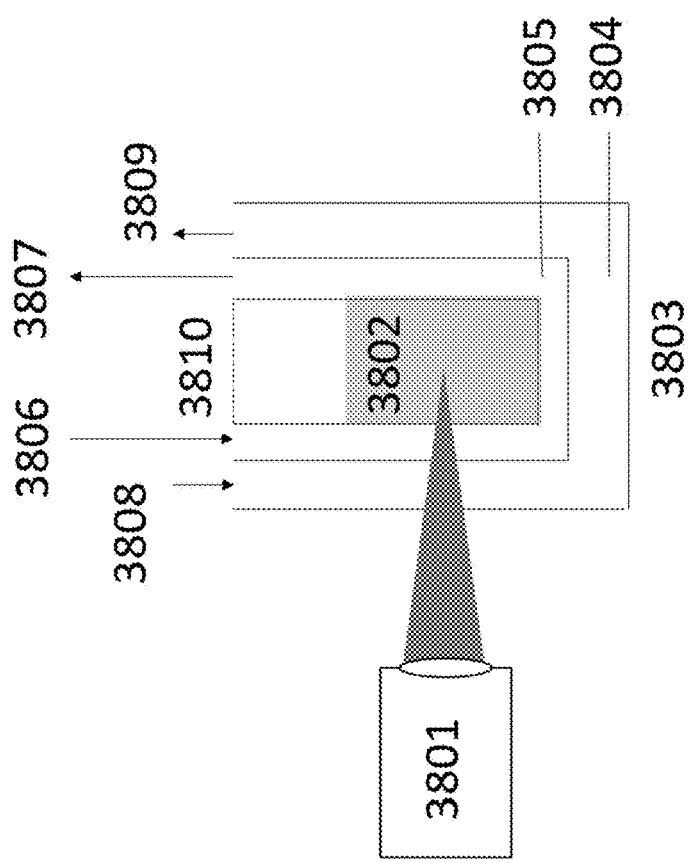

FIGS. 38A and 38B illustrate a reaction vessel that is designed to prevent formation of condensation on its walls and that includes a cavity for circulation. FIG. 38A illustrates the cavity as closed. FIG. 38B illustrates the cavity as open and permitting circulation of a fluid.

FIGS. 39A and 39B illustrate a dry enclosure used prevent formation of condensation on the walls of a reaction vessel. FIG. 39A illustrates the Raman system outside the dry enclosure.

FIG. 39B illustrates the Raman system inside the dry enclosure.

Figure 40:
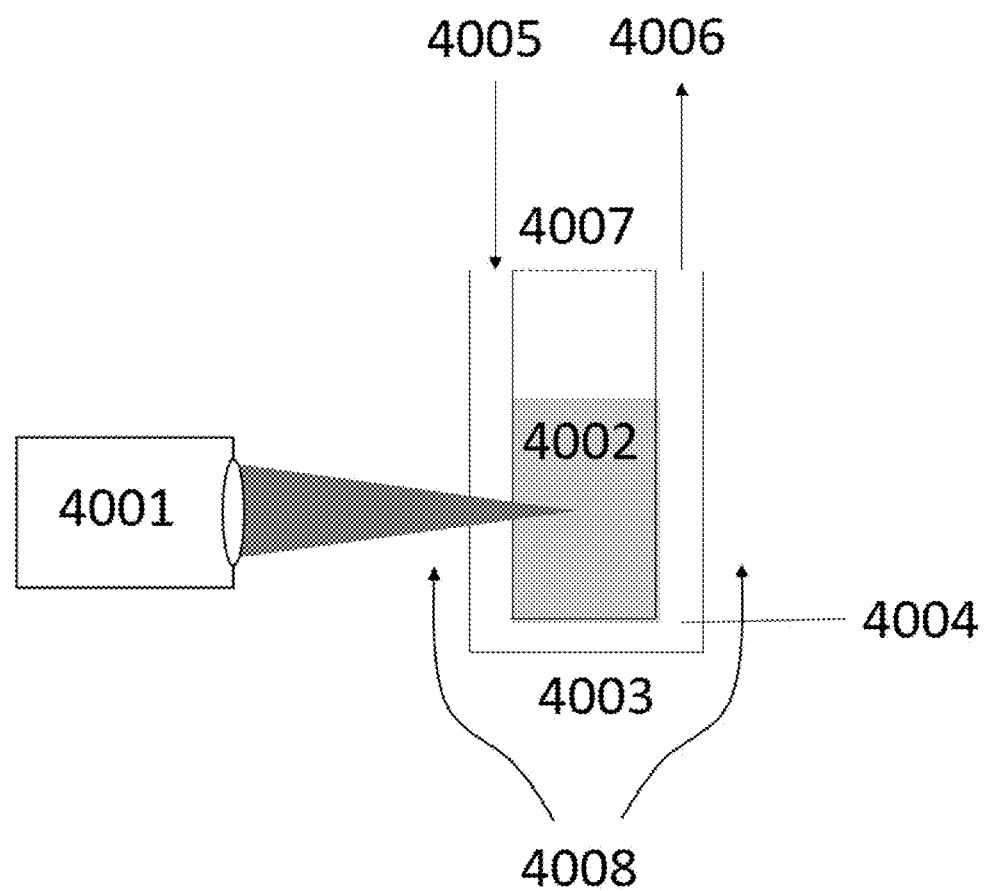

FIG. 40 illustrates a dry gas flow used prevent formation of condensation on the walls of a reaction vessel.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Eye Safety and Explosion Mitigation

A method of Raman spectroscopy includes projecting a first Raman pump beam at a first wavelength onto a sample from a standoff distance of at least 10 centimeters. The method also includes detecting a first Raman signal emitted by the sample in response to the first Raman pump beam, the first Raman signal representing a first Raman signature and a first background signature. The method further includes projecting a second Raman pump beam at a second wavelength different than the first wavelength onto the sample from the standoff distance. The method also includes detecting a second Raman signal emitted by the sample in response to the second Raman pump beam, the second Raman signal representing a second Raman signature and a second background signature. The method further includes generating a post-processed signature based on at least one of the first Raman signal or the second Raman signal, the post-processed signature having a background lower than or equal to the first background signature.

A method of Raman spectroscopy includes acquiring interleaved measurements of a first Raman signal of a sample using a Raman pump at a first wavelength, a second Raman signal of the sample using a Raman pump at a second wavelength different than the first wavelength, and ambient light transmitted and/or scattered by the sample from a distance of at least 2 cm from the sample. The method further includes generating a post-processed signature based on the interleaved measurements of the first Raman signal, the second Raman signal, and the ambient light.

A method of Raman spectroscopy of a sample includes scanning a first Raman pump beam at a first wavelength in a scan pattern across a surface of sample over a first scan period and measuring a first Raman signal scattered by the sample in response to the first Raman pump beam over a first integration period. The method also includes scanning a second Raman pump beam at a second wavelength different than the first wavelength in the scan pattern across the surface of sample over a second scan period and measuring a second Raman signal scattered by the sample in response to the second Raman pump beam over a second integration period. The method further includes measuring ambient light transmitted and/or scattered by the sample over a third integration period, and forming a post-processed signature based on the first Raman signal, the second Raman signal, and the ambient light.

A method of Raman spectroscopy of a sample can include measuring a range of between about 2 centimeters and 400 centimeters from a Raman spectroscopy system to the sample, and automatically focusing a Raman pump beam emitted by the Raman spectroscopy system based on the range from the Raman spectroscopy system to the sample. The method can also include detecting a Raman signal from the sample in response to the Raman pump beam, and estimating a Raman signature of the sample based on the Raman signal.

A method of Raman spectroscopy of a sample includes illuminating the sample, via a telescope, with a first ranging beam propagating along an optical axis of the telescope to form a first spot on the sample. The method also includes illuminating the sample, via the telescope, with a second ranging beam propagating along a marginal ray of the telescope to form a second spot on the sample. The method includes detecting a distance between the first spot and the second spot and adjusting a focus of the telescope based on the distance between the first spot and the second spot. The method also includes illuminating the sample, via the telescope, with a Raman pump beam propagating along the optical axis of the telescope and measuring a Raman signal scattered by the sample in response to the Raman pump beam.

A Raman spectroscopy system can include a camera to acquire an image of a scene and a processor, operably coupled to the camera, to identify a target in the scene based on the image of the scene. The system can also include a laser, in optical communication with a sample in the scene, to illuminate the target with a Raman pump beam. The system further includes a detector, in optical communication with the sample, to detect a Raman signal scattered by the target in response to the Raman pump beam.

A system for Raman spectroscopy includes a housing and at least one ranging laser, disposed within the housing, to emit a first visible ranging beam and a second visible ranging beam. The system further includes a telescope, disposed with the housing in optical communication with the at least one ranging laser, to project the first visible ranging beam to a first spot on a sample located between about 2 centimeters and about 4 meters from the housing and to project the second visible ranging beam to a second spot on the sample, the first spot and the second spot providing an indication of a range to the sample. The system also includes at least one Raman pump laser, disposed within the housing, to emit a first Raman pump beam at a first wavelength and a power level of at least about 10 mW during a first period based on a flicker period of ambient illumination and to emit a second Raman pump beam at a second wavelength different than the first wavelength and a power level of at least about 10 mW during a second period equal to and after the first period. The system also includes a beam scanner, disposed within the housing in optical communication with the at least one Raman pump laser and the telescope, to scan the first Raman pump beam across a portion of the sample during the first period and to scan the second Raman pump beam across the portion of the sample during the second period, the telescope focusing the first Raman pump beam and the second Raman pump beam on or near a surface of the sample. The system also includes a detector, disposed within the housing in optical communication with the sample, to detect a first Raman signal from the sample during the first period, a second Raman signal from the sample during the second period, and the ambient illumination transmitted or scattered by the sample during a third period equal to and after the second period. The system further includes a processor, disposed within the housing and operably coupled to the detector, to produce a post-processed signature based on the first Raman signal, the second Raman signal, and the ambient illumination signal, the post-processed signature having a lower fluorescent background than the first Raman signal and the second Raman signal.

A spectroscopy system includes a laser to illuminate a sample at a distance of at least 2 centimeters from the spectroscopy system with a laser beam having first laser safety class, and a beam steering element, in optical communication with the laser, to scan a spot formed by the laser beam across a surface of a sample. The spectroscopy system also includes a monitoring system, operably coupled to the beam steering element and/or to the laser, to detect a malfunction of the beam steering system that would cause the laser beam to exceed a maximum permissible exposure for a second laser safety class and to at least one of attenuate, redirect, block, or turn off the laser beam in response to detection of the malfunction.

A spectroscopy system includes a laser configured to illuminate a sample at a distance of at least 2 centimeters from the spectroscopy system, and a beam steering element, in optical communication with the laser, to scan a spot formed by the laser beam across a surface of a sample. The system also includes a monitoring system to measure the sample temperature and automatically shut off the laser or reduce its emission power should a temperature rise above a certain threshold be detected.

A spectroscopy system can be configured to illuminate a sample at a distance of at least 10 centimeters from the spectroscopy system with a Raman pump beam at a wavelength of about 700 nanometers to about 1050 nanometers and with a power of at least 10 mW A method of spectroscopy can include emitting a Raman pump beam from a laser, the Raman pump beam having a power of more than about 5 milliwatts and a wavelength of about 700 nanometers to about 1050 nanometers. The method can also include focusing the Raman pump beam to a spot on a sample at a distance of about 2 centimeters to about 10 meters from the laser, scanning the spot across at least a portion of the sample, and detecting radiation emitted by the sample in response to the Raman pump beam.

A spectroscopy system can include a housing, an optical assembly, and a camera, disposed within the housing in optical communication with the optical assembly, to acquire an image of a sample via the optical assembly. The spectroscopy system can also include a laser, disposed within the housing, to emit a Raman pump beam, and a beam-steering element, disposed within the housing in optical communication with the laser and the optical assembly, to scan the Raman pump across the sample via the optical assembly. The spectroscopy system can also include a spectrometer, disposed within the housing, to detect Raman light scattered by the sample in response to the Raman pump beam.

A spectroscopy system includes a housing, an optical assembly, and a camera, disposed within the housing in optical communication with the optical assembly, to acquire an image of a sample via the optical assembly. The spectroscopy system also includes a laser, disposed within the housing, to emit a Raman pump beam and an actuator to move the optical assembly with respect to the sample. The spectroscopy system further includes a spectrometer, disposed within the housing, to detect Raman light scattered by the sample in response to the Raman pump beam.

The technology presented here can be used to reduce the laser energy impinging at any one point of the sample, and, through imaging by the lens of the eye at any one point of the retina, increase eye safety. We achieve this here by scanning the Raman pump beam over a small area of the sample to be analyzed. For the sake of simplicity, the implementation details and calculations refer to a Raman system with a NIR pump laser, with wavelength between 700 nm and 1050 nm. Other wavelengths are also possible. The accessible emission limit (AEL) for a Class 3R instrument in this wavelength range and for exposure times relevant to Raman analysis is:

$$\text{AEL(in Joules)} = 3.5 \times 10^{-3} C_4 C_6 t^{0.75} \qquad (1)$$

$$\text{AEL(in Watt)} = 3.5 \times 10^{-3} C_4 C_6 t^{-0.25} \qquad (2)$$

where $C_4$ is a correction factor accounting for the laser wavelength ($C_4 = 10^{0.002(\lambda - 700)}$, with $\lambda$ being the laser wavelength in nanometers), $C_6$ is a correction factor accounting for the source size (extended source, $C_6 = \alpha/\alpha_{min}$, with a the angular subtended by the apparent source and $\alpha_{min} = 1.5$ mrad), and t is the exposure duration.

Established laser-safety standards are mostly concerned with fixed (non-scanning) lasers, either pulsed or operated in continuous wave. The treatment of scanned beams is described in the IEC 60825-1 Standard as follows: "For laser products emitting a scanned beam, depending on the accommodation condition to image the apparent source, a scanning beam can result in the image of the apparent source being scanned across the retina, resulting in a moving apparent source. If a moving apparent source is to be accounted for in the classification, the classification of the product is based on the evaluation method described here for extended sources (in contrast to the simplified analysis where a small source is assumed to be stationary). The moving apparent source is to be evaluated as described in 4.3. d) [i.e. non-uniform, non-circular or multiple apparent sources] with due consideration of the repetitive pulse nature of the accessible emission determined with the respective angle of acceptance." Eye-safety assessment should follow three rules:

The exposure from any single pulse within a pulse train should not exceed the maximum permissible exposure (MPE) for a single pulse.

The average exposure for a pulse train of exposure duration T should not exceed the MPE for a single pulse of exposure duration T.

The exposure per pulse should not exceed the MPE for a single pulse multiplied by a correction factor ($C_5$) accounting for repeated exposures.

In studying a scanned beam, we calculate the average exposure over all or part of the scanned area, for varying time scales including the scan period, in order to find the most restrictive condition. Pulsed exposure is used to consider the transient exposure of a spot as the laser beam travels through it. In this case, we consider a scanned laser to be equivalent to a pulsed laser with a spot size equal to the spot size obtained when the laser scanning is turned off, and with a pulse duration equal to the time it takes for the beam to be scanned across a length equal to the spot diameter. For the repeated pulse condition, that pulse is considered repeated every time the scan pattern crosses that same area.

Figure 6:
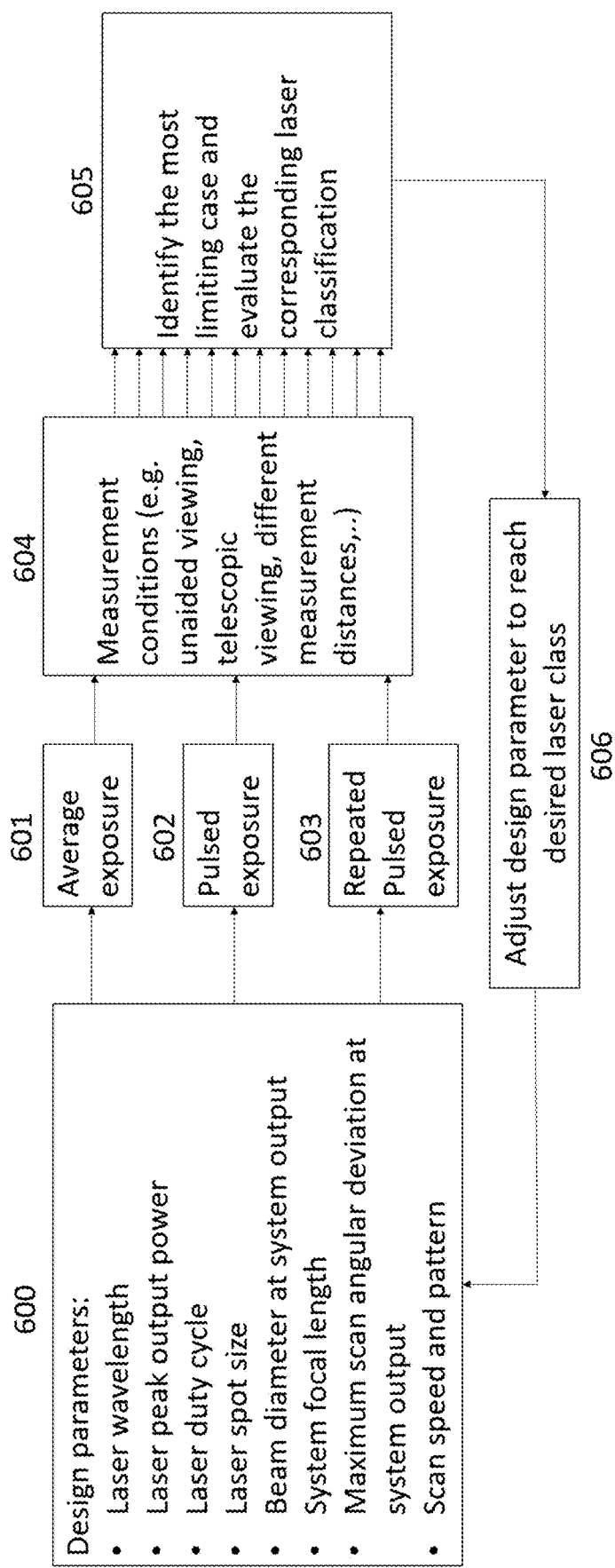
FIG. 6 illustrates a process for determining system design parameters that can be adjusted to obtain a desired laser classification for the system.

FIG. 6 illustrates a process for determining the system design parameters that can be adjusted to obtain a desired laser classification for any system described herein. At 600, the main design parameters, discussed in greater detail below, are used as inputs to calculate, the exposure levels reaching the eye under several possible exposure (at steps 601/602/603) and measurement conditions (at step 604), and each of the average exposure, pulsed exposure, and repeated pulsed exposure conditions are described in greater detail below. At 604, the case with the highest exposure is identified and compared with the corresponding accessible exposure limits, according to published eye safety standards. Based on the result of this comparison, a laser classification can be determined, and if desired the parameters can be adjusted at step 606 to adjust the laser classification. Note that the final laser classification may entail additional requirements, such as safety markings or the presence of fail-safe mechanism, warning lights, key locks, etc., that are not considered here since they can be independently added as desired.

We detail below some example system parameters (values, ranges, degrees of freedom, etc.) that can affect eye safety of the system under consideration:

Laser (Raman pump laser) wavelength: e.g., between about 250 nm and about 1100 nm.

Laser peak output power (as measured at the system output port): e.g., between about 5 mW and about 5 W.

Laser duty cycle: e.g., between 1% and 100%.

Laser spot size (without scanning, measured on the sample): e.g., between about 1 micrometer and about 500 micrometers in diameter.

Beam diameter at the system output port (e.g., the telescope's exit lens, which may form the boundary between the instrument and the environment surrounding the instrument): e.g., between about 6 mm and about 100 mm, depending on the desired standoff distance.

System focal length (distance from beam output port and the focused spot): e.g., between about 1 cm and about 10 meters.

Scan maximum angular deviation (measured at the system output port): Consistent with a position shift of the focused spot of less than about 1 inch on the sample, as described in greater detail herein.

Scan speed: full accessible deviation range scanned in a time (scan period) that is from about 5 microseconds to about 500 milliseconds.

Scan pattern, and the fill-factor of the scan pattern and its uniformity (ratio of highest exposure to average exposure) within the bound of the scan maximum angular deviation.

Of these parameters, two are particularly significant for the ability of a Raman system to obtain high quality data, in terms of signal-to-noise ratio and spectral resolution: the laser power and the system etendue. The etendue is a measure of how diffuse a light source is, in area and angle. For a Raman spectrometer, the etendue can be approximated as:

$$G = \frac{A_{laser}A_{lens}}{s^2} \qquad (3)$$

where G is the etendue, $A_{laser}$ is the area of the source (laser facet, or optical fiber facet), $A_{lens}$ is the illuminated area of the focusing lens (the telescope used to image the laser or fiber facet on the sample is simplified to a simple equivalent lens), and s is the distance between the focusing lens and the laser source. The laser spot diameter d on sample is directly related to $A_{laser}$ by the magnification provided by the focusing lens:

$$d = \frac{s_1}{s}\sqrt{\frac{4}{\pi}A_{laser}},$$

where $s_1$ is the distance between the focusing lens and the sample (system focal lens). The beam diameter D at the system output is such that $$A_{lens} = \frac{\pi}{4}D^2.$$

The etendue can also be expressed as:

$$G = \pi A_{spot}(NA)^2 \qquad (4)$$

where $A_{spot}$ is the area illuminated by the laser on sample (i.e., $$A_{spot} = \frac{\pi}{4}d^2$$

using the notations above), and NA is the system numerical aperture:

$$NA = \frac{D}{2s_1}$$

using the notations introduced above. The notations are also illustrated in FIG. 7, which illustrates a Raman pump source 700 (e.g., a laser facet or optical fiber facet) with area $A_{laser}$ is imaged by a focusing lens 701 onto a sample 702. The laser spot 703 has an area $A_{spot}$ while the beam illuminates an area $A_{lens}$ of the focusing lens. The distance between the source and the lens is s while the distance between the lens and the sample is $s_1$.

In general, decreasing the laser power and/or increasing the etendue tends to increase eye safety and mitigate explosion risk of the sample because doing so decreases the sample irradiance as well as the amount of light that can be collected by the eye pupil. However, decreasing the laser power reduces the signal-to-noise ratio and consequently increases the measurement time, while increasing the etendue tends to reduce the spectral resolution, and can also negatively affect collection efficiency and thus signal-to-noise ratio. The devices and methods presented here increase eye safety while maintaining a high laser power and a small etendue.

We show below that a class 3R system can be obtained with an output power greater than 5 mW and an etendue smaller than 0.2 mm$^2$.

We detail below how different conditions (average exposure vs pulsed exposure vs repeated pulsed exposure) drive certain design considerations for a scanning eye-safe laser system.

Average Exposure

At every point of the scan pattern an accessible emission (defined in the IEC 60825-1 standard as "level of radiation determined at a position and with aperture stops (when the AEL is given in units of Watts or Joules) or limiting apertures (when the AEL is given in units of W·m-2 or J·m-2) as described in Clause 5") averaged over the full period of the scan can be derived. The scanned area represents an effective extended object. When considering the constraints driven by an average exposure, the maximum permissible exposure (defined in the IEC 60825-1 standard as "level of laser radiation to which, under normal circumstances, persons may be exposed without suffering adverse effects") may increase as the total area illuminated by a given power is increased. Instrument optics generally limit the maximum angular deviation that can be achieved for a scan pattern, and thus can establish a practical or maximum achievable scan area. We can characterize the fill factor as the ratio of illuminated area to maximum achievable scan area. A low fill factor may not be desirable in some cases because it implies that the average laser energy is concentrated onto a few points within the maximum scan area. Since the average exposure of the points receiving the highest average exposure may drive eye-safety considerations, patterns with higher fill factors with uniform exposure across the maximum scan areas are usually desirable. Examples of low fill factor trajectories are straight lines, circles, or ellipses. Examples of high fill factor patterns are 2D rasters (with interline spacing close to the instantaneous spot size) or Lissajous patterns.

In addition to the fill factor of the pattern, the uniformity of the illumination can be important, for the same reason that the average exposure of the points receiving the highest average exposure drives eye-safety considerations. In practice this means for example that a raster or Lissajous patterns with triangular functions are preferable to similar patterns with sinusoidal functions, since they result in more uniform intensities: for a triangular raster, the laser dwells less at the end of each line where the scan direction is reversed, compared to a sinusoidal raster where the scan speed slows progressively to zero at the end of each line before reversing direction and slowly accelerating back. In general, average accessible emission is evaluated at different time scales and over different areas in order to find the most restrictive conditions. In practice, the most restrictive conditions are often be found near the edges and corners of a scan pattern where the scan speed is lowest and where two or more successive exposures can occur in a short time frame.

A pattern's uniformity may be affected by the intrinsic properties of the pattern itself, but also by possible system throughput modulations as a function of scan angle. For example, the output laser power may be reduced at the edges of a raster pattern by optical vignetting or spatial filtering. Additionally, the laser power may be directly modulated following a pattern synchronized with the scan, to reduce the power in some specific regions of the scan pattern. Whether specifically designed or not, such scan position-dependent power modulation may be considered when calculating the maximum permissible laser exposure for a laser system.

Pulsed Exposure

When considering a pulsed exposure, it is useful to describe an 'instantaneous' spot size, i.e., the laser spot size that would be obtained with no scanning. If we assume a one-dimensional scan along a given direction at a given speed (more complex scan patterns can be addressed as a succession such short scan segments), we can consider the effective pulse duration as the time it takes for the instantaneous laser spot to travel across a distance equal to its diameter. The pulse duration is thus proportional to the spot size. We assume here a circular spot, but the discussion can be straightforwardly extended to irregularly shaped spots by considering its dimension in the direction of the scan. Since the angular subtense of the apparent source a is also proportional to the spot size and from the AEL expression in equation (2), we see that the accessible laser power (in Watts) increases with increasing spot size according to a $s^{0.75}$ law, where s is the laser spot size.

The duration t of the effective pulse is equal to s/v, where s is the spot diameter and v is the scan velocity on target. From the AEL expression in equation (2), the accessible laser power (in Watts) increases with scan velocity as $v^{0.25}$.

As discussed in the case of an average exposure, non-uniformity in the scan pattern can be damaging. From the point of view of the instantaneous exposure, a point with a slower scan velocity (assuming constant power throughout the scan pattern) may be the most limiting. Power modulation across the scan pattern, either designed in the optics with the use of spatial filtering or vignetting of the beam, or through direct modulation of the laser beam power, can be used to increase the uniformity of the exposure.

Repeated Pulsed Exposure

The previous considerations revealed that a large spot scanned rapidly across a wide area with close to unity fill-factor can be preferable in some cases, in the sense that it increases or maximizes the power of the Raman pump laser that can be used for a Class 3R laser system. We now consider the limiting case of repeated pulses: if the scan pattern retraces several times through the same point, which happens at least once for each period of the scan pattern for a periodic pattern, an additional correction factor should be included when calculating the AEL: $C_5=N^{-0.25}$, where N is the number of pulses in a train of pulses. Taking the example of a standard raster pattern along a fast axis scan (e.g., 200 Hz frequency) and a slow axis scan (e.g., 20 Hz frequency), a point along the trajectory is illuminated twice per raster frame period, i.e., twice within $\frac{1}{20}^{th}$ of a second using the examples of scan rate given above. N is the number of pulses within the maximum time $T_2$ to be considered, with $T_2 = 10 \times 10^{[(\alpha - \alpha_{min})/98.5]}$ seconds for $\alpha_{min} < \alpha < 100$ mrad.

What this consideration implies is that, in some embodiments, the pattern can be chosen in a way that avoids retracing often onto the same spot or group of spots on the sample. As in previous considerations, the point that sees the most repeated exposures within a scan frame sets the upper limit on laser power. The laser power will be limited in a manner proportional to $N^{-0.25}$, which is a similar rule as the one derived above for the duration of the effective pulse in the previous case (pulsed exposure), where the laser power is limited in a manner proportional to $t^{-0.25}$, with t the duration of the effective pulse.

One should note that for small source ($\alpha<5$ mrad) and long enough pulse duration ($t>T_i$, where $T_i=5$ μs for example for wavelengths between 400 and 1050 nm), $C_5$ should be considered equal to 1 according to the IEC 60825-1 standard. Furthermore, if α>5 mrad, one can still calculate AEL based on α<5 mrad according to the IEC 60825-1 Interpretation Sheet 1: "When the class of a laser product is determined with the extended analysis (subclause 5.4.3) and the apparent source is larger than 5 mrad, the classification may be based on a value of the angular subtense of the apparent source less than 5 mrad (resulting in a smaller $C_6$ but also larger $C_5$). That is, when the AE is below the AEL for an assumed smaller apparent source, the resulting class is applicable even though the image of the apparent source is larger than 5 mrad" As a result, repeated exposures may not be a concern (from a pulse exposure point of view) for certain systems with small sources, if there a delay greater than $T_i$ between repeated exposures. However, the average exposure may then constraint the maximum allowable exposure for a certain laser class.

Laser Duty Cycle

The laser may be operated in continuous wave (CW) or pulsed mode. The laser safety standards clearly indicate how to consider these different conditions, and such conditions can be incorporated in the calculations outlined here. The laser beam scanning method described here may be effective for both CW and pulsed laser systems.

Beam Divergence

In general, and for a fixed distance between the apparent source (defined in the IEC 60825-1 standard as: "for a given evaluation location of the retinal hazard, real or virtual object that forms the smallest possible retinal image (considering the accommodation range of the human eye)") and the eye, the collected energy into the eye pupil decreases as the laser beam divergence increases. However, when considering Raman instruments with visible or near infrared pump lasers, the distance to be considered between the apparent source and the eye should be adjusted to find the most restrictive position. For example, IEC 60825-1:2014 states that "For radiation with wavelengths in the retinal hazard region 400 nm to 1400 nm, when the AEL is increased by a parameter $C_6$ with values greater than 1 for extended sources, it is necessary to assess the class of the product (i.e., to compare the accessible emission value with the corresponding AEL) at the most restrictive position in the beam." In practice, the most restrictive position is often close to the point where the laser beam just fills the eye pupil, which may be taken, in some cases, as having a 7 mm diameter. Therefore, the reason a less divergent beam is often more restrictive on allowable laser power is generally not because of increase in the fraction of power collected in the pupil but because the image of the apparent source on the retina is smaller, concentrating the energy onto a smaller region of the retina.

For an instrument with a fixed aperture diameter, the beam divergence decreases with increasing standoff distance. The scan area is typically limited in term of the maximum deviation angle achievable by the optical system. Therefore, the maximum scan area increases with increasing standoff distance. It may desirable for practical purposes to limit the scan area so that the interrogated area overlaps well with the analyte of interest. The laser safety assessment should be realized at the standoff distances accessible by the instrument, so that the most constraining condition is identified. In general, the most constraining condition is found at the longest standoff distance, since these correspond to a lower beam divergence than closer standoff distances. Note however that the laser scanning methods presented here are especially effective at long standoff distances.

Example of a Scanning System

Figure 3B:
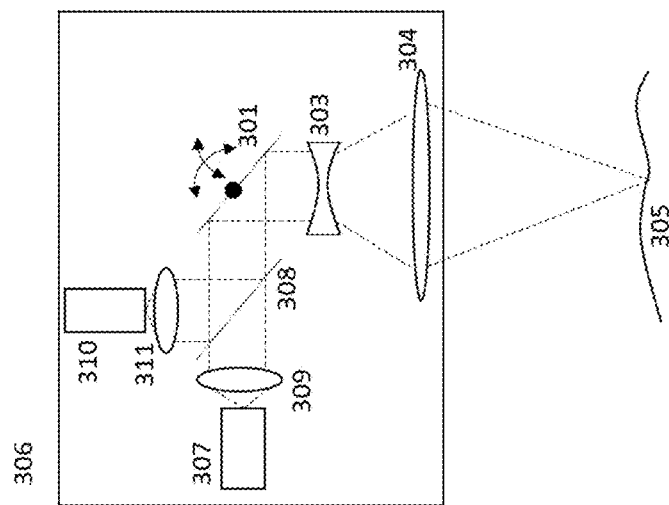
FIG. 3B is a schematic of an example of a retracing beam scanning device.
Figure 3A:
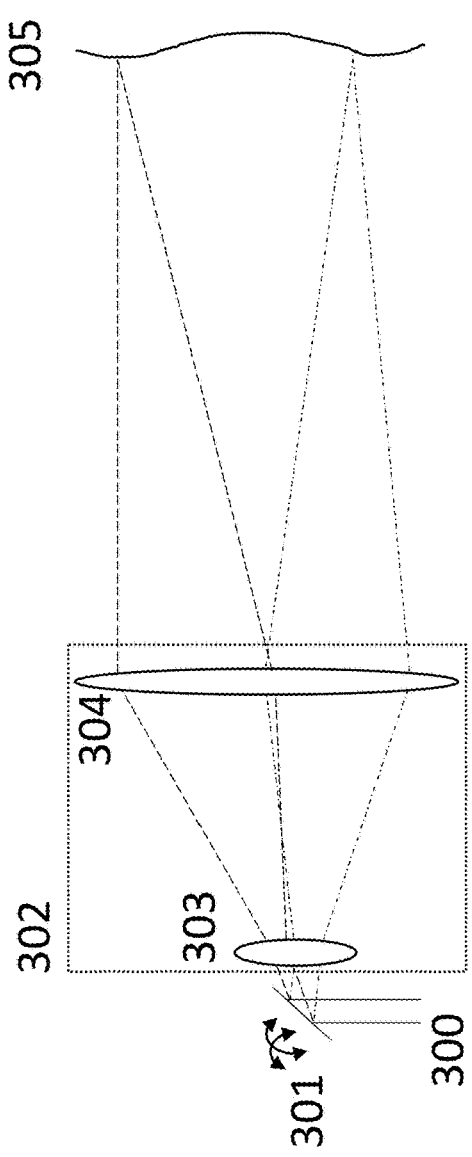
FIG. 3A is a schematic of an example beam scanning device.

FIG. 3A is a schematic of an example beam scanning device. The Raman pump beam 300 is incident on a tip-tilt mirror 301 located in front of a telescope/telescope optics 302, formed by two lenses 303 and 304, that focuses the beam onto the sample 305. The Raman scattering photons emerging from the sample 305 are collected by the same telescope 302, directed to the same tip-tilt mirror 301, which has not moved during the time it takes for the photons to do the round trip between the instrument and the sample (few nanoseconds). As a result, the Raman scattering photons are reflected by the tip-tilt mirror 301 towards a detector (not shown) in a direction colinear to the initial Raman pump beam 300.

More generally, laser beam scanning can be achieved using the tip-tilt mirror 301 at the entrance of the telescope 302 used to focus the laser beam 300 onto the sample 305. Assume that the telescope input is a collimated beam and that the telescope 302 has a magnification M expressed as the ratio between the output beam diameter to the diameter of the input collimated beam. If the entrance tip-tilt mirror 301 provides a maximum angular deviation for the laser beam 300 of $\theta_{max}$, then the maximum angular deviation of the beam at the output is $\theta_{max}/M$. This may be further reduced by vignetting in the telescope 302.

Another consideration when designing a scanning system, such as the system/device of FIG. 3A, is to ensure that both the light from the light source and the light received from the sample propagate along the same path (in opposite directions) through the system, as shown in FIG. 3B. Consider a mechanical frame (reference frame) in which the light source (Raman pump laser) and the detector (or for a Raman system, the entrance slit to a spectrometer) are fixed, for example, the mechanical frame of the system 306 in FIG. 3B. A Raman pump laser 307 emits a beam collimated by lens 309. That beam is fixed in the reference frame and is directed through a dichroic beam splitter 308 toward a tip-tilt mirror 301 whose orientation changes with respect to the reference frame. This results in a beam of varying orientation entering the fixed telescope optics (303 and 304), and correspondingly the Raman pump beam is focused to a varying point on the sample 305. There is a one-to-one relationship between the tip-tilt angles of the mirror at the entrance of the telescope and the position of the focused spot on the sample to be analyzed.

The Raman scattering emitted from the spot illuminated by the Raman pump beam and its surroundings is collected by the same telescope optics 303 and 304 as the one used to focus the Raman pump beam. Consequently, that scattered light exits the telescope with the same direction as the one the Raman beam had: the two beams are collinear. The resulting beam is sent back to the tip-tilt mirror 301, which reflect the beam toward the beam splitter 308 with the same orientation (and opposite direction of travel) as the Raman pump beam. The Raman scattering is reflected by the dichroic mirror 308 and focused onto a slit at the input port of the spectrometer 310. An optical fiber may be used to guide light between the laser and the collimating lens 309 and between the focusing lens 311 and the spectrometer 310.

Upon reflection on the tip-tilt mirror 301, since the delay between the time when the photons from the pump beam 300 impact the mirror and the time when the scattered photons impact the mirror 301 is negligible compared to the time scales at which the mirror 301 moves, the mirror 301 can be considered fixed. For example, for a standoff distance of 1 meter, the round-trip travel time for photons is about 6 ns, while a mirror oscillation period is typically in the millisecond range. With the mirror 301 considered fixed at the photon round trip travel time scale, the scattered photons reflect off the tip-tilt mirror in a direction collinear with the Raman pump beam. In other words, the direction of the scattered photons reflected off the tip-tilt mirror is fixed with respect to the fixed instrument mechanical frame, including the spectrometer entrance slit. The scattered photons can thus be efficiently collected by a small aperture, e.g., the spectrometer entrance slit, or an optical fiber facet or other optical aperture.

Temperature Rise of the Sample

A high laser exposure on the sample is also sometimes associated with explosion or ignition risk if the material being analyzed or a nearby material is flammable or combustible. Alternatively, the sample may heat up so much under the high radiance of the Raman pump that it emits an incandescent glow that interferes with or altogether prevents the measurement. From this point of view, there is also a desire to reduce the radiance on the sample, which is addressed by the system presented here.

In addition to risks of sample explosion or ignition, it may be desirable to avoid a significant temperature rise of the sample or analyte in order to prevent a perturbation of a chemical reaction occurring in the analyte, for example by altering the possible reactions pathways or altering the reaction kinetics.

Local temperature heating of the analyte may also give rise to convection flows or eddies in the analyte, potentially disturbing the measurement by introducing a dynamic process and material variations over time.

Fail-Safe Mechanism

The IEC 60825-1 standard states: "Laser products intended to emit scanned radiation and classified on this basis, shall not, as a result of scan failure or of variation in either scan velocity or amplitude, permit human access to laser radiation in excess of the AEL for the assigned class, unless exposure of people is not reasonably foreseeable during the time interval between failure and when the scanning safeguard reduces emission to levels below the AEL of the class of the product."

The paragraph above indicates that a fail-safe mechanism should interrupt the laser if a failure of the scanning mechanism is detected and if the safety class of the system relies on the scanning system proper operation. This can be realized by adding a secondary system/device monitoring the movement of the parts responsible for laser beam scanning. For example, if beam scanning is achieved using a tip-tilt mirror at the entrance of the telescope as illustrated in FIGS. 3A and 3B, a laser diode can be used to illuminate the tip-tilt mirror, with the reflection directed towards a four-quadrant detector. The signal output from such a detector can be processed to derive the position of the mirror, and thus ensure that the beam is being scanned as expected.

Aspects of such a scan monitoring system/device can be directed to monitoring that:

The beam has moved across a distance equal to its diameter in a time short enough to ensure that the maximum permissible exposure has not been surpassed based on the pulsed exposure calculation;

The beam is not re-exposing a spot more than expected, ensuring that the maximum permissible exposure has not been surpassed based on the repeated pulsed exposure calculation;

The beam is scanned following a pattern such that the maximum average exposure at any point does not exceed the maximum permissible exposure based on the average exposure calculation.

This implies that the scan monitor should have a fast response time, typically on the order of the time it takes for the laser spot to travel across a distance equal to its diameter, and a memory of previous positions at least sufficient to store one full scan period.

In addition to ensuring that limits for a certain laser class are not exceeded, a monitoring and fail-safe mechanism can be used to ensure that the risk of sample explosion or ignition is properly mitigated. This can be achieved using the same mirror monitoring device described above, with a similar fail-safe control system.

Figure 5:
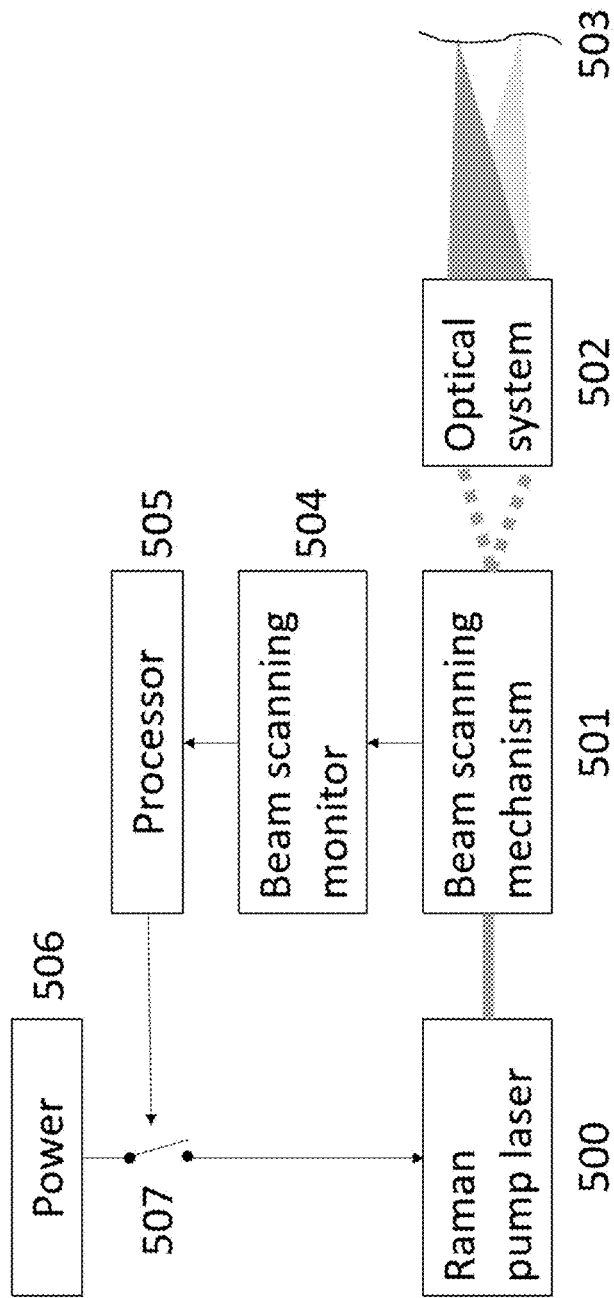
FIG. 5 is a schematic of an example fail-safe mechanism.

FIG. 5 is a schematic of an example fail-safe mechanism that can be associated with any Raman system/device described herein. The beam emitted by the Raman pump laser 500 is scanned using a beam scanning mechanism 501 (e.g., galvanometer scanner(s) and directed to an optical system 502 (e.g., focusing optics) that focuses the beam onto a sample 503. The beam scanning mechanism 501 is monitored by an independent monitor system/device 504 that measures the angle and/or position of the beam scanning mechanism. The signal output is analyzed by a processor 505, which decides whether the movement of the beam scanning mechanism 501 is within acceptable bounds to ensure safe operation (for example, for eye safety and/or explosion mitigation). If the movement is outside of pre-programmed bounds (e.g., if an angle of a galvanometer scanner exceeds a predetermined threshold), the processor 505 can control a switch 507 to cut the power 506 to the Raman pump laser 500.

The reaction time of the fail-safe system can be fast enough to ensure that the accessible emission limit (AEL) (defined in the IEC 60825-1 standard as: "maximum accessible emission permitted within a particular class") for eye-safety for a particular laser class is not reached. An exact calculation of the accessible emission with a failed scanner enables determination of the maximum allowed reaction time, but in general a reaction time equal to the time it takes for the laser spot to move by a distance equal to its diameter (the distance is measured in the focus plane, on the sample) may be sufficient. A slower reaction time may be allowed as indicated in the IEC 60825-1 standard: "For example, a scanning safeguard may not react fast enough to prevent emission above the AEL during the fault condition; however, this might be acceptable based on the results of a risk analysis." (Paragraph 5.1 Note 2).

Additionally, we describe below a different method to ensure that the risk of sample explosion or ignition is properly mitigated, as can be carried out by example systems generally illustrated in FIGS. 8A and 8B. It is understood that while some instances describe the target as a sample while others describe the target as the pupil of an eye of a subject/person, requirements/demands on the Raman systems as disclosed herein can be applicable to tailored to any suitable target using the approaches described herein.

FIG. 8A is a schematic of a standoff sample temperature monitoring system 800. The system 800 includes a Raman laser 801 that emits a beam focused onto the target 803 using a first optical system/setup 802. A second optical system 804 collects an infrared thermal emission from the sample area illuminated by the laser and focuses it onto an infrared detector 805, which may be an array for local imaging, or a single pixel detector.

FIG. 8B is a schematic of another embodiment of a standoff sample temperature monitoring system 806 that can be used with any Raman system described herein. The system 806 includes a Raman laser 807 that emits a beam focused onto the sample 809 using the optical system/setup

808. The same optical system 808 is used to collect the infrared thermal emission from the sample area illuminated by the laser 807, which is then separated from the Raman laser light and Raman scattered photons using a dichroic beam splitter 810 and focused onto an infrared detector 811.

More generally, an infrared thermometric device (e.g., the detector 805 or 811) pointing at the sample can be used to ensure that the sample is not heated beyond a certain limit above ambient temperature. The measure of the sample temperature at the point illuminated by the laser can be realized using an infrared camera or a single pixel infrared detector: the infrared thermal emission from the sample area illuminated by the laser is focused onto an infrared detector. The intensity of the measured signal can be related to the sample temperature with proper calibration.

The optical system for such a camera or detector can be a separate system, or it can share the same optics as the main Raman system, if allowed by transmission and dispersion properties of the material used. For example, a reflective telescope may be used which can efficiently image the spot illuminated by the laser onto an infrared camera or detector, as well as focus the Raman laser (for example, with a wavelength of 785 nm) onto the sample and collecting the scattered Raman photons (for example, in the NIR band). The infrared thermal emission, the Raman laser and the scattered Raman photons can be routed through the beam scanning device to ensure that they all are focused from or are originating from the same point on the sample.

The sensitivity, accuracy, and time response of the camera or detector should be selected to ensure adequate measure of a potential temperature rise and allow for the system reaction is a certain limit is exceeded. A typical off-the-shelf infrared camera can measure temperature differentials in the tens of milli-Kelvin range, whereas it is expected that an accuracy of 0.1-1 K should be sufficient to monitor a potential temperature rise of the sample.

FIG. 9 is a schematic of another example fail-safe mechanism (e.g., for explosion or ignition risk mitigation) based on measurement of the sample temperature and can be used with any Raman system described herein. The beam emitted by the Raman pump laser 900 is scanned using a beam scanning mechanism 901 and directed to an optical system 902 that focuses the beam onto a sample 903. The temperature of the illuminated area of the sample 903 is measured, either in absolute terms or relative to the surrounding non-illuminated material, using a calibrated infrared thermometric device (not shown). The signal output is analyzed by a processor 905, which decides whether the sample temperature is under a certain threshold or not. The threshold may be an absolute temperature, or a relative temperature compared to ambient or compared to the surrounding sample material. If the temperature is above a certain threshold, a switch 907 cuts the power 906 to the Raman pump laser 900, preventing emission of more light from the Raman pump laser 900. The reaction time of the fail-safe system should to be fast enough to ensure that the maximum allowed sample temperature (absolute or relative) is not reached.

Two different thresholds may be used to trigger the automatic shut-off of the laser 900: (1) a relative temperature rise, compared to ambient or compared to neighboring, non-illuminated material, or (2) the absolute temperature of the sample, which may be known to ignite or explode above a certain temperature. These thresholds may be informed by experiments, and may be dependent on the sample being measured, or the environmental conditions surrounding the sample (temperature, pressure, presence of oxygen, humidity, presence of flammable materials, etc.)

In another temperature measurement method, any suitable Raman spectroscopy system described can be used to determine the temperature of the analyte, either by observing a shift of a narrow Raman line, or by measuring the ratio of the signal strength for a Raman band, observed at the Stokes and anti-Stokes positions. The second measurement method relies on the observation of both a Stokes and an anti-Stokes signal for a given Raman band. This is usually easier for a band with a low Raman shift, since the signal strength of the anti-Stokes peaks decreases exponentially with increasing Raman shift.

FIG. 10 generally illustrates this approach and shows the different Raman signals that can be observed. Typically, the Stokes Raman scattering 1014 is used for chemical analysis since the anti-Stokes peaks (see anti-Stokes Raman scattering 1010) are much weaker. If a Raman peak with a low Stokes shift is present, and if allowed by the bandwidth of the Raman filter used to suppress the Rayleigh scattering 1012, the corresponding anti-Stokes peak may be observed. The ratio of amplitudes between the two peaks (anti-Stokes and Stokes) may then be used to measure the temperature of the sample.

A Raman temperature marker may be added to the analyte to facilitate the temperature measurement using such approaches. The temperature marker may be a material with one or several of the following features: (1) a molecule (e.g., a diatomic molecule, such as $O_2$) having a simple Raman spectrum, (2) a molecule having at least one strong Raman peak with a low frequency shift (<500 $cm^{-1}$) (e.g., a diatomic molecule with heavy atoms or a material such as sulfur), (3) a chemically inert molecule, (4) a material that can be easily separated from the analyte after analysis (e.g., magnetic nanoparticles), and/or (5) a material with a simple Raman spectrum (one or few isolated Raman peaks) that is easily separable from the spectrum of the analyte of interest (e.g. Silicon (Si) particles). Such a Raman marker can be added to the analyte before analysis. By providing a strong Raman band with a low Raman shift, it can allow for temperature measurement based on the ratio of the Stokes and anti-Stokes signals for this band. The marker may then be extracted using standard chemistry separation techniques. A chemically inert marker is desirable so that it does not interfere with the reaction, for example, in the case of reaction monitoring in a reaction vessel.

FIG. 11 illustrates the use of a Raman temperature marker for temperature measurement of the analyte. (1) Consider a reaction vessel containing one or a few analytes. At (2), a Raman marker material, which can be any suitable material as described above, is added. This material has specific characteristics for measuring the temperature of the slurry or liquid in the vessel. At (3) the measurement is realized, which can possibly include, but is not limited to, continuously monitoring a reaction. The Raman signal from the Raman marker allows measurement of the temperature of the analyte. (4) The Raman marker is separated from the rest of the analyte after analysis.

Embodiment of a Fail-Safe Mechanism

Figures 4A, 4B:
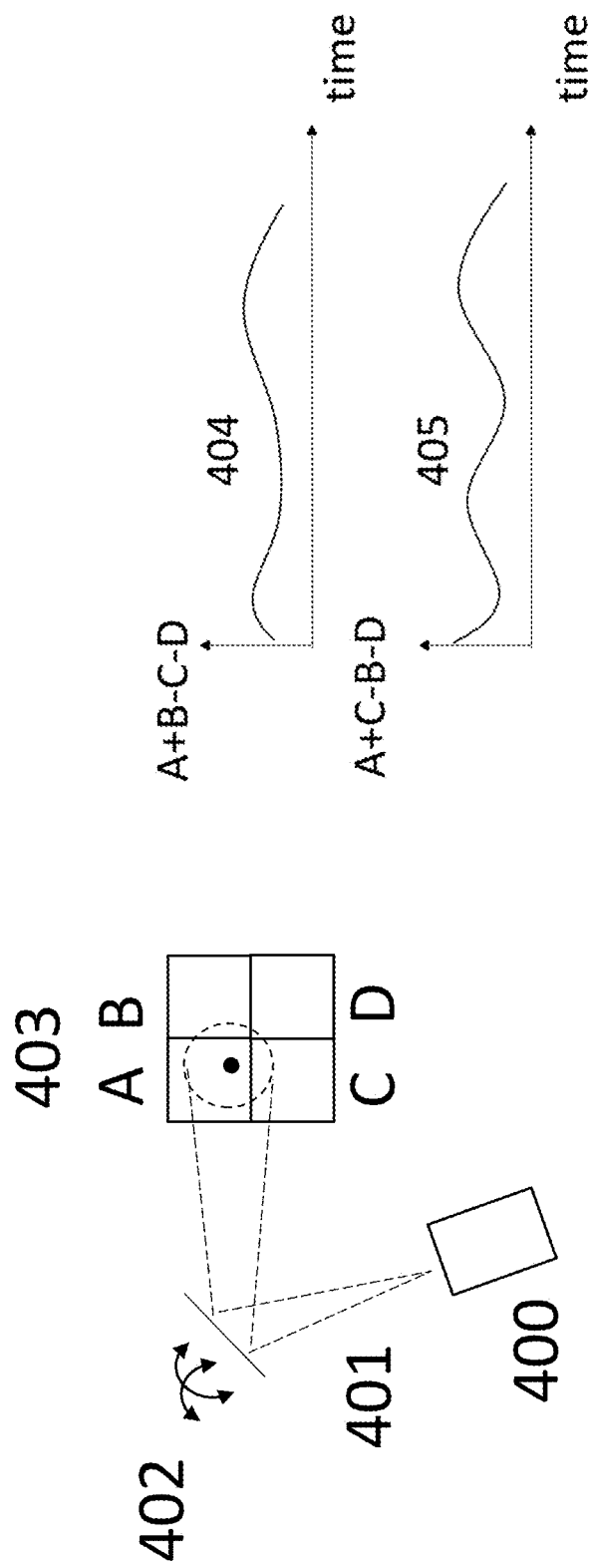
FIG. 4A is a schematic of a mirror monitoring device.
FIG. 4B illustrates time signals (upper and lower plots) from a four-quadrant detector.

We consider a laser system with a beam scanning optical system that is monitored so that the position of the scanning optics (e.g. tip-tilt mirror) is recorded over time, and the data is available for quasi-real time processing and analysis. FIG. 4A is a schematic of a mirror monitoring device and illustrates a light source 400 (e.g., a light emitting diode or laser) that emits a beam 401 directed at the tip-tilt mirror 402 in a direction that is typically different from the direction of incidence of the Raman pump beam to avoid interfering with the transmission of the Raman pump beam. The reflected light is directed to a four-quadrant detector 403.

FIG. 4B illustrates time signals 404 (upper plot) and 405 (lower plot) from the four-quadrant detector (with quadrants A, B, C, D) that allow a processor (not shown) to evaluate the angle of the tip-tilt mirror 402 in real-time, and consequently to evaluate whether the beam scanning is occurring in a manner consistent with the expected pattern. The four-quadrant detector provides a signal proportional to the light intensity impinging on each quadrant (A, B, C and D) and a processor computes the three following signals: the sum signal from all four quadrants as a measure of total beam intensity, the difference between the top and bottom halves (A+B−C−D) indicating position of the beam along the top-down axis, and the difference between the left and right halves (A+C−B−D) indicating the position of the beam along the left-right axis.

Thus, generally, a secondary laser (e.g., the light source 400) incident on the optics with its deflection measured with a four-quadrant detector (the detector 403) is one embodiment of such monitoring system. The system may keep in its memory the history of the position(s) reached by the beam scanning optics, which can be mapped one-to-one to the positions reached by the laser spot on target. If the power of the laser is known, potentially as a function of deflection angle of the beam scanning optics, a map of total energy deposited at each point within the instrument scanning range or field-of-view can be calculated. This map can be updated by incrementing the corresponding total energy for the spots successively exposed as the beam is scanned. At each spot, the energy deposited can be compared to the maximum permissible exposure level for a laser system of a certain class. If the energy deposited approaches the maximum permissible value, the instrument can be automatically turned off by the system embedded electronics and software. Since different conditions needs to be considered (pulsed exposure, average exposure), several maps can be acquired: a map containing information on instantaneous exposure, for which the energy deposited is incremented when a spot is exposed, and decremented if the spot has not been visited for more than $T_i$ (defined in the IEC 60825-1 standard as the time below which pulse groups are summed); and a map containing information on average exposure, acquired for example over a scan period. The exposure values in these maps can be compared with their respective maximum permissible exposures.

Potentially Limiting Cases

The beam divergence (which can be expressed as a function of the beam diameter at the system output and of the system focal length) as well as the laser average power and wavelength are also used to determine eye and/or sample safety. We consider here two limiting cases for determining the remaining system parameters:

In the limit of a fast laser beam scanning (as fast as possible), the 'pulsed exposure' AEL becomes higher than the 'average' exposure AEL. In other words, the average exposure may limit the laser power of the system for a certain class. Affected design parameters include the total span and fill factor of the scan pattern (i.e., the total illuminated area, if we assume a uniform exposure).

In the limit of a slow laser beam scanning (as slow as possible), the pulsed exposure may limit the laser power. In that case, affected parameters include the laser spot size and the scan speed.

Scanning to Reduce Risk of Ocular Damage or Explosion

Figure 1:
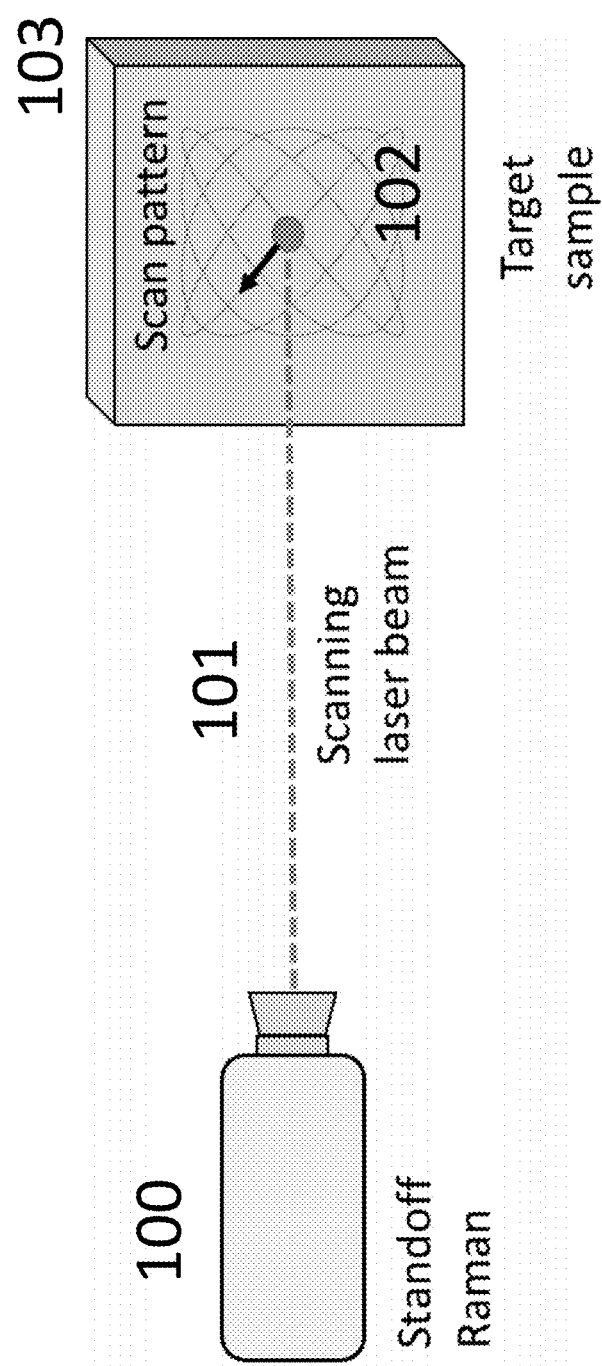
FIG. 1 is an example of scanning standoff Raman system.

An example embodiment of such a Raman system is shown in FIG. 1, which illustrates a scanning standoff Raman system 100 being used on a target sample 103. The system 100 generates and scans the Raman laser beam 101 over the target sample 103 with a predetermined pattern 102 and speed to mitigate laser eye-safety (ocular damage) or risk of explosion due to temperature rise of the sample 103. If the scan pattern has a high area fill-factor with high linear scan speed, the effective laser spot may become indistinguishable from that produced by spatially incoherent sources, such as light emitting diodes or flashlights. The increase in surface temperature of the sample 103 caused by laser beam illumination would be lower with such a scanned pattern 102 than without scanning; hence mitigation of explosion of a target sample due to temperature rise. Similarly, the image of such a scan would produce a lower temperature increase at any point on the retina of an observer compared to the temperature increase obtained without scan; hence the increase in eye-safe laser power.

Figure 2C:
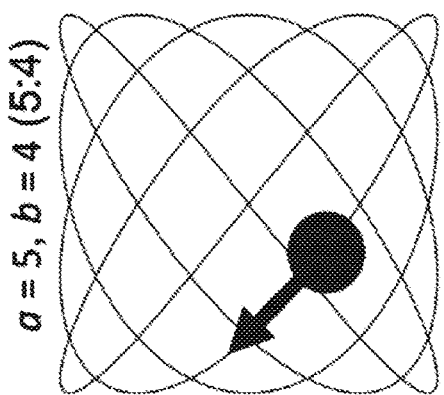
FIGS. 2A-2C illustrates different possible scan patterns. A low fill-factor scan pattern, such as the circumferential pattern shown in FIG. 2A would heat selected portions of the surface of the sample or the retina of the eye more than the higher fill-factor patterns shown in FIG. 2B (raster pattern) and FIG. 2C (Lissajous pattern).
Figure 2B:
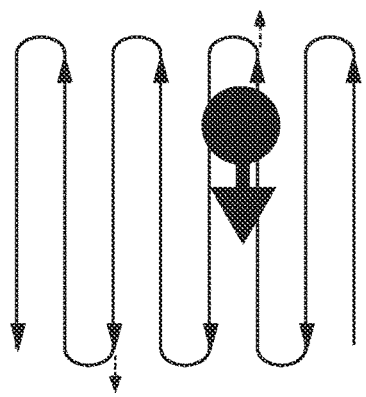
Figure 2A:
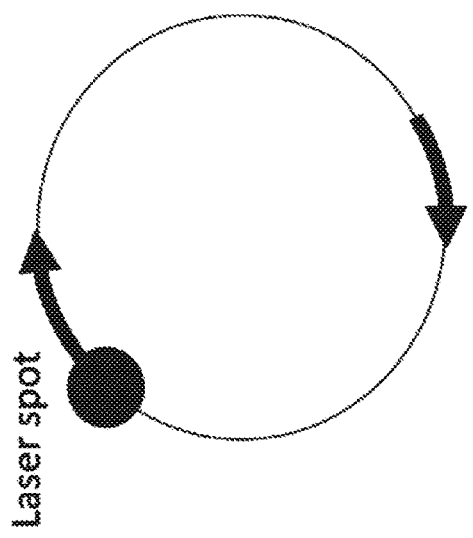

FIGS. 2A-2C indicates some examples of scan patterns. A low fill-factor scan pattern shown in FIG. 2A would heat selected portions of the surface of the sample or the retina of the eye more than the higher fill-factor patterns shown in FIGS. 2B and 2C.

The patterns with higher fill-factor (ratio of illuminated area to total area encompassed by the pattern) are more effective at reducing heating due to absorption of laser power by the sample or retina. Specifically, the patterns of FIGS. 2B and 2C have higher fill factors than the pattern of FIG. 2A and spread the thermal load over a larger area, reducing the likelihood of thermal damage to an observer's retina or the risk of explosion of the sample. As illustrated in FIG. 2C, the pattern can be a Lissajous pattern with a=5 and b=4, where a and b are used to describe the pattern as a graph of a system of the following parametric equations: $x=A\sin(at+\delta)$, $y=B\sin(bt)$.

The example patterns of FIGS. 2A-2C aside, any suitable scan pattern permitted by the scanning system/optics can be employed. For a given slow axis frequency (b for example), the fast axis frequency (a) may be chosen to ensure enough fill of the pattern, considering the spot size and the total scanned area. For example, a=10b or a=25b may be practical and desirable. Having a be an integer multiple of b can be advantageous to ensure that the scan pattern is periodic with frequency b. Such repeatability can be useful to synchronize the processes used to acquire a Raman spectrum.

The dwell time of the spot at each point can be chosen to be small enough to satisfy the eye safety requirement of a given laser class. Faster linear scan for any pattern reduces thermal damage at any given spot on the retina or risk of sample explosion.

In some cases, scan patterns where scan lines take more time to come close to each other would reduce thermal crowding and may be preferred. For example, in the Lissajous pattern of FIG. 2C, the folding lines are father away for longer time before coming close to each other compared to the raster pattern in FIG. 2B, where each row is followed by an adjacent row.

Consider the following system specifications: An instrument with a 12-mm diameter beam at the system output, focusing to a spot on the sample located 80 mm in front of the instrument. The tip-tilt mirror used to scan the beam has an oscillation period of 100 Hz along the fast axis, and a mechanical maximum deviation angle of 4 degrees. The corresponding illuminated area on the sample, averaged over a mirror scan period, is about 0.9 mm×0.9 mm. The system is configured to have an instantaneous spot size of 0.15 mm. The laser peak power is 100 mW (66 mW average power), and the wavelength is 785 nm. The system etendue as defined above is $G=3\times10'$ mm$^2$. We consider an evaluation condition such that the eye is located 10 cm directly in front of the focused spot. Under these conditions, we find that the system is at ~73% of the accessible emission limit (AEL) for a class 3R pulsed and repeated pulsed source (which is how we model the instantaneous exposure), and at ~87% of the AEL for a class 3R system when the average effective extended source is considered. Contrast this to the case when the scan motion is stopped: in this case, the system's AEL is five times higher than the AEL for a class 3R system.

Accordingly, any Raman system described herein can be outfitted with a monitoring system/component that is coupled to beam steering elements such as the tip-tilt mirror and/or to the laser, and can detect a malfunction that would cause the laser beam, when having a first laser safety class, to exceed a maximum permissible exposure for a second laser safety class which is lower than the first laser safety class. The second safety class can be, for example Class 3B or 3R according to the IEC 60825-1 standard, or class 1, etc. The result can be that this monitoring system can attenuate (e.g., via a controllable filter), redirect (e.g., via a controllable mirror), block, and/or turn off the laser beam in response to this detection. In some cases, as detailed herein for FIGS. 8A and 8B, the monitoring system/component can take such actions upon detecting that the temperature of the sample is above a threshold value.

Handheld Standoff Differential Raman Spectroscopy

Drawbacks of Conventional Handheld Raman Spectroscopy Systems

As noted above, Raman spectroscopy has proven to be a highly valuable portable analytical tool for accurate chemical identifications. The most common implementation, the operator must hold the Raman spectrometer close (less than couple of centimeters away) to the substance under investigation, illuminating the substance with a pump laser and collecting the Raman scattering.

Existing handheld Raman systems that aim at providing a fieldable capability for rapid chemical analysis of solids and liquids typically have a very short standoff distance—less than 1 inch in most cases. There exist a few reasons for the use of such small measurement distance:

In part, this is to maintain a small instrument form factor by using a small focusing lens at the instrument output: however, a smaller lens provides a smaller collection efficiency for the scattered Raman photons if the standoff distance was increased.

Since the systems are typically classified as Class 3B lasers for eye safety, having a small measurement distance allows the use of a shield that screens potentially harmful radiation reflecting from the sample being analyzed, and prevents such radiation from reaching the operator's eyes.

In many cases, the systems are designed to contact the samples, conveniently maintaining the distance between the instrument and the sample to ensure optimal focusing and correspondingly increasing or maximizing the signal-to-noise ratio.

The small standoff distance makes it convenient to shield the sample from ambient light, which can create a background signal that can interfere with the Raman signal.

The drawbacks of such a small standoff distance include:

The operator needs to spend time setting up the measurement, carefully positioning the instrument in close proximity to the sample such that the focused Raman probe is on the sample (or in the sample in the case of a liquid), which sometimes requires moving obstacles or clearing space around the sample to properly position the instrument. In addition to requiring time, this task can also be dangerous as it presents risks of spilling chemical containers or triggering chemical reactions in the process of clearing space around a sample in a cluttered scene. An instrument with an increased standoff distance would facilitate measurements in such crowded environments.

Since the operator needs to bring the instrument close to the sample, the operator herself usually needs to be close to the sample, which may be a toxic compound or present an explosion risk. The measurement itself may trigger an explosion of the sample, further endangering the operator. This risk is sometimes mitigated with the use of a time-delayed measurement, which further increases the overall measurement time. By increasing the distance between the operator and the sample, an instrument with an increased standoff distance would increase operator safety.

If the instrument is close to the sample, the instrument (and the user) may become contaminated by the sample or surrounding chemicals. An increased standoff distance may decrease the risk of contamination of both the user and the instrument. And with an increased standoff distance, the sample (or the instrument) can be placed in an enclosure to further reduce the risk of such contamination. For example, the sample may be left in a fume hood or a closed sample compartment, while the instrument can measure through the closed window of a fume hood or the (transparent) walls of the sample compartment.

In some cases, the instrument cannot be brought close to the sample, e.g., the sample may be at the bottom of a container with a narrow opening, behind a glass or plastic barrier, contained in a thick-walled container, etc. Instead of opening the corresponding containers, windows, fume-hood sash or other obstacles, an instrument with an increased standoff distance would provide a way to realize the measurement rapidly and directly through the obstacle.

In addition, most existing handheld Raman analyzers have difficulty analyzing samples with strong fluorescence (or photoluminescence). For these samples the Raman signatures are often much smaller than a large, broad fluorescence background that carries limited chemical-specific information. That background is largely un-helpful in identifying the chemicals measured, and the shot noise associated with that background can overwhelm the Raman signatures. The background may also be modulated by the instrument transfer function, producing small ripples in the signal that can be difficult to separate from the Raman signal using background suppression methods.

A typical solution to the problems caused by this background is the use of a longer wavelength for the Raman pump laser since the fluorescence of many materials scales down with increasing wavelength. For example, systems with a pump wavelength of 1064 nm have been developed to have improved performance in the presence of strong fluorescence compared to the more common instruments using a 785 nm pump wavelength. However, the use of a longer wavelength can come at the expense of a poorer detector performance. Instruments with a pump wavelength 1064 nm typically use Indium Gallium Arsenide (InGaAs)

detectors with much higher dark noise than the silicon detectors used in 785 nm pump-wavelength instruments.

Raman microscopes are commonly used in laboratories to analyze spectroscopically small samples (e.g., single or few grains or particles, fibers, hairs, etc.) or to map the chemical composition of a heterogenous solid mixture (e.g., a pharmaceutical pill). These instruments are typically table-top units and use typical microscope objectives with short working distances. To ensure eye-safety, the instruments are often enclosed in an enclosure opaque to the laser wavelength used as the Raman pump. Alternatively, the sample compartment (instead of the full instrument) may have a movable or articulated panel that allows the compartment to be closed to prevent light from the Raman laser from escaping the sample compartment and the rest of the instrument. These enclosures often also serve as a shield for ambient light, preventing the room lights from reaching the sample and from being collected by the instrument optical system. Reducing this background signal facilitates the spectral analysis of the Raman signatures. Such a microscope often uses an eye-piece or a digital camera to view the sample and align the Raman pump laser to specific features of interest, such as individual particles. To obtain an image, the sample can be moved under a fixed Raman laser spot, using a motorized two-axis (x-y) stage or the Raman spot may be scanned over the sample.

These instruments suffer from a few limitations, including:

It is sometimes undesirable to confine the sample, or all or part of the instrument, in an enclosure to provide eye-safety and eliminate ambient light. For example, it may be advantageous for the operator to be able to manipulate the sample, hold a part of the sample, or re-position the sample, while rapidly triggering measurements on demand, e.g., when a portion of the sample of interest is at the location of the Raman laser focus.

The measurement of very fluorescent samples is often difficult because of the absence of fluorescence mitigation.

The measurement of dark, colored, or very absorptive materials can be difficult because of problems linked to the local heating of the sample due to absorption of the Raman laser energy. Potential issues include ignition or explosion of the sample, or incandescent glow from the sample saturating the detector.

A Raman spectrometer can also be used as a chemical analysis tool to monitor chemical synthesis. For such an instrument, an increased standoff capability compared to existing instruments can allow to directly probe the reagents inside a reaction vessel, whether directly through the walls of the vessels in the case of transparent plastic or glass vessels, or through observation ports with a glass or plastic window, or through other openings in the vessel. Whereas a Raman probe is currently often inserted in the vessel and into the reagents, which can cause contamination issues and may not be practical if several vessels or reactions are to be monitored with one instrument, a standoff instrument does not use a probe inserted into the vessel or chamber or into the reagents themselves. This is attractive because it reduces or eliminates contamination. Such instruments could also benefit from fluorescence mitigation since some reagents may have strong fluorescence. Additionally, shielding the light at the point of measurement may not always be practical in a well-lit chemistry laboratory. Doing so could create unpractical obstructions around the reaction vessel, possibly adding safety hazards. Finally, a solution for increased eye safety and explosion mitigation is of interest since some reagents or synthesis products may be explosives or flammables, having the potential to be ignited by the Raman laser.

Handheld Raman Spectrometers

FIG. 14 is a block diagram of an example handheld differential Raman spectroscopy system 1400. The system includes a Raman pump laser 1402 that couples to a probe 1404 external to a sample 1406. A telescope system 1408 is employed to couple the pump beam from the laser 1402 to the sample 1406, and to receive emission from the sample 1406. A camera 1408 coupled to the telescope 1408 can be employed for various purposes as described herein including, but not limited to, image stabilization, sample temperature monitoring, etc. The system 1400 also includes a Raman spectrometer 1412 with a dispersive element, such as a grating or prism, and a camera (e.g. a CCD or CMOS array) 1414 for receiving the Raman signal from the sample 1406 and for generating the Raman spectrum therefrom.

The system 1400 also includes a controller/processor/central processing unit (CPU) 1418 for receiving the digitized Raman spectrum from the digitizer 1416, and for presenting a representation of the spectrum on a user interface 1420, such as a display screen of the user interface. As illustrated in FIG. 14, the user interface 1420 can encompass multiple interface elements including, but not limited to, a display screen, touch screen, one or more switches, indicator lights, and one or several visible pointing lasers used to give user feedback on the aim and/or focus of the system.

The system 1400 can also include various components for control and/or operation of the components noted above. For example, as illustrated in FIG. 14, the CPU 1418 can control operation of the laser 1402 using a laser driver 1422. A thermo-electric cooler (TEC) 1424a, and its corresponding TEC control 1226a, are coupled to the laser 1402 and controllable by the CPU 1418 keep the temperature of the laser 1402 within predetermined ranges. Similarly, a TEC 1424b and a corresponding TEC controller 1426b are coupled to the CCD 1414 and controllable by the CPU 1418 to control the temperature of the CCD. A motor controller 1428 is coupled to the CPU 1418 to permit control of a motor 1430 that manipulates one or more optical components associated with the telescope 1408 such as, for example, a tip-tilt mirror as shown in FIGS. 3A and 3B.

FIG. 14 also illustrates a power supply 1432 for powering components of the system 1400, and an input/output interface 1434 for communication with other devices/systems and including, for example, one or more USB ports, a GPS receiver, etc.

More generally, an example handheld, standoff Raman spectrometer can include (1) a Raman pump laser, (2) an optical system/telescope focusing the laser output onto the sample and collecting the scattered Raman photons, (3) a spectrometer analyzing the collected scattered light and outputting the Raman spectrum, (4) electronics and power sub-systems supporting operation of the above components. The optical system may include a beam scanner to scan the beam for eye safety and explosion/combustion mitigation as described above. The spectrometer typically includes an entrance slit, a first lens collimating the light emerging from the slit and directing the light to a fixed diffraction grating, a second lens to focus the light diffracted by the grating onto an image sensor. In typical operation, the laser source (Raman pump laser) is turned on and the CCD integrates the signal received in the different pixels, each of which corresponds to a different wavelength bin. At the end of a set integration time, the electronics read the image sensor to obtain a Raman spectrum. The operation can then be repeated to average the measurement over N frames. Finally, the laser is turned off. We note that the image sensor may be a CCD camera, a CMOS camera or other similar image acquisition hardware. In the rest of the description, the use of CCD to describe the image sensor is not meant to be prescriptive of a particular type, and alternative image sensors may be used.

FIGS. 12A-12E are a collection of schematics representing different measurement conditions for a standoff Raman analyzer, or other laser-based, standoff spectrometers. FIG. 12A illustrates standoff measurement of a solid sample at its surface. FIG. 12B illustrates standoff measurement of a liquid in a container through the container wall. The container should be at least partially transparent to the Raman wavelength and the neighboring Stokes range. In addition, or alternatively, FIG. 12C illustrates standoff measurement of the liquid in the container through the container opening. FIG. 12D illustrates standoff measurement of an analyte in a reactor such as, for example, through a port (e.g., window) in the reactor wall. The instrument may be positioned in direct contact with the reactor wall or spaced therefrom. FIG. 12E illustrates measurement of an analyte in a flow cell.

The system is designed to allow for handheld operation. The design accommodates drifts in the operator's aim during the measurement. This drift changes the location of the interrogated spot on the sample over the duration of the measurement, leading to potential fluctuations in the measured Raman signal.

FIG. 13A is a photograph of an example handheld Raman standoff differential spectroscopy system with an internal beam scanner that reduces the risks of ocular damage and sample explosion or combustion. FIG. 13B illustrates the handheld Raman standoff differential spectroscopy system during use, when measuring a white powder through the closed window of an oven.

Dynamic Background Subtraction

The integration/frame time is short (<0.5 s), and a background frame is interleaved between successive Raman frames. Here, "background frame" refers here to a CCD frame for which no Raman laser illuminates the sample during the frame integration time. In contrast, a Raman frame is obtained when a laser (the Raman pump laser) illuminates the sample during the frame integration time. The fast interleaving of background frames allows the electronics to subtract the effects of ambient light, even when the background due to ambient light fluctuates, because of modulation of the ambient light source itself or because of the operator's hand movements.

Difference Raman Spectroscopy

FIG. 15 illustrates an example difference Raman spectroscopy system 1500 with two or more lasers. It is understood that, unless explicitly noted otherwise, components of FIG. 15 may be functionally and/or structurally similar to similarly named components of FIGS. 14, 16. For example, the telescope 1408 may be similar to the telescope 1508, and so on. FIG. 15 illustrates a bank of lasers 1502a, 1502b . . . 1502n (with lasers 1502a, 1502b shown for simplicity), and an optical switch 1530 for switching between lasers.

Using the scenario where the system 1500 includes two lasers 1502a, 1502b, the system 1500 described here uses two Raman pump laser beams with closely spaced wavelengths: the system is a differential Raman system, related to what is sometimes referred to as Shifted Excitation Raman Difference Spectroscopy (SERDS). A frame is acquired with the first Raman laser beam (e.g., the laser 1502a), then a second frame is acquired with the second Raman laser beam (e.g., the laser 1502b). From Kasha's rule, the fluorescence signal is similar between the two frames in the limit of a small difference in excitation wavelength. Consequently, subtracting two frames eliminates the fluorescence signal, but preserves the Raman information because the Raman spectrum shifts with a shift of the excitation wavelength. In some cases, the fluorescent background is not entirely removed, if for example the power of the two Raman lasers is not exactly the same, or if there is a slight difference in absorption between the two Raman lasers. Even if the fluorescent background is not entirely cancelled, the reduction of its amplitude with respect to the Raman signature will greatly assist analysis of the Raman signal.

In other words, the difference Raman technique involves acquiring successively the Raman spectra of a sample using two pump lasers with closely spaced wavelengths or a single laser that emits two pump laser beams with closely spaced wavelengths in quick succession. The two laser beams excite a similar fluorescence response from the sample, but the Raman signatures are shifted, allowing one to extract the chemically specific ro-vibrational (Raman) information from non-specific chemical fluorescence. The technique is compatible with the interleaving of background spectra measurements to efficiently subtract ambient light features (e.g., room lights, sun), as described above. In this case, the difference spectrum may be obtained as the difference of two intermediate spectra, one obtained as the difference of a first Raman spectrum and a background spectrum (which can be acquired when, for example, neither laser 1502a not laser 1502b is operating), the second obtained as the difference of a second Raman spectrum and a background spectrum. The background spectra may be identical for both sets. Since each intermediate may be processed, which includes for example removal of cosmic ray signatures, as well as scaling of the spectra along the intensity axis, or shifting of the spectra along the wavenumber axis, the information from the background spectrum does not necessarily cancel out when the final difference spectrum is computed. In general terms, a difference spectrum can be calculated from the information contained in the three spectra potentially acquired (first Raman spectrum, second Raman spectrum and background spectrum).

Difference Raman spectroscopy can be used to remove any common background between spectra acquired with different Raman pump wavelength. This includes fluorescence of the analyte or of the substrate, fluorescence from internal instrument optics, ambient light, blackbody emission from a hot analyte or substrate, and dark current from different CCD pixels.

More than two laser beams can be used for difference Raman spectroscopy, as illustrated in FIG. 15. As long as the wavelengths of the different laser beams used are close enough, such that Kasha's rule remain valid and the fluorescent background is common to the spectra obtained with the pump laser beams, the component of the spectra due to Raman scattering can be extracted from the common background (fluorescent, photoluminescence, or ambient light). In some cases, the difference between wavelengths of successive lasers can be about 0.25 nm, about 1 nm, about 2 nm, about 5 nm, about 10 nm, including all values and sub ranges in between.

The Raman laser beams used for difference Raman spectroscopy may be emitted by two or more individual lasers, either separately packaged or co-packaged into a single sub-system, or by a single tunable laser that is successively tuned between two emission wavelengths, using a thermal control (e.g., modulation of the laser heat sink temperature), electrical tuning (e.g., modulation of the laser drive current), mechanical tuning (e.g., rotation of a frequency-selective feedback grating), etc. The lasers may be semiconductor laser diodes with external feedback gratings for frequency stabilization. The laser(s) may be Distributed Bragg Reflector (DBR) laser(s) or Distributed Feedback (DFB) laser(s) whose output wavelengths can be tuned by varying the injected current (the refractive index of the semiconductor material may be affected by the current injected in the DBR) or the heat sink temperature.

When multiple lasers are used, it may be desirable to combine their outputs so that the beams illuminate the same spot on the sample. Since the lasers illuminate the sample sequentially, this beam combining can be achieved using a switch, such as the optical switch 1534. For example, an opto-mechanical switch can be used to select which laser's output is directed to the input port of an optical system that focuses light onto the sample. Such switch can be a fiber-coupled switch, having two fiber-coupled lasers as inputs and a single fiber as an output, directing the light towards the system sampling port or probe. A third input, kept dark, may be used to obtain a condition where no laser light is directed at the sample, to measure background ambient light collected by the system, for subsequent subtraction from the Raman spectra. If such a switch is used, the lasers may be operated in continuous wave.

Alternatively, the outputs from the different lasers used as Raman pump lasers, such as the lasers in FIG. 15, may be beam combined in a permanent, static manner. Different laser beam combining approaches may be used: spectral beam combining, aperture multiplexing, knife-edge combining, etc. The different lasers are permanently coupled, either in free-space or via an output fiber, such that their beams form a single output beam.

To sequentially illuminate the sample with the different lasers, one may modulate the lasers directly. In other words, the lasers may be turned on and off by controlling their electrical power supply, allowing to control if one, several or no laser(s) illuminate the sample at any given time. This approach can offer greater switching speed (switching at microsecond time scale, compared to a millisecond time scale for a typical opto-mechanical switch). It also allows for more complex illumination patterns (more than one or no laser at a time) and can save power since the lasers are consuming the most power when they illuminate the sample.

The lasers may be kept at a constant temperature, for example, using a thermo-electric cooler and its associated control electronics. That temperature may be the same or different between the different Raman lasers used. The lasers may also be left uncooled (i.e., no temperature regulation). In this case, the wavelengths of the Raman lasers may drift over time as the instrument temperature varies. The relative temperature drift between the different Raman lasers may be reduced or minimized by thermally connecting the lasers, either through a common sub-mount or a common heat-sink or a thermal connection between their respective heat-sinks.

If the wavelengths of the Raman lasers can drift, knowledge or a measurement of the Rayleigh scattering (zero-Stokes shift peak) in the spectrometer can be used as a reference for calculating the Stokes shift of the Raman spectrum. In other words, the spectrometer measures the spectrum of the incoming Raman scattering in absolute units (i.e., wavelength of the Raman scattering photons). However, the information used to identify a chemical based on its Raman spectrum is the Stokes shift of the Raman features, i.e., the energy difference (usually expressed in $cm^{-1}$) between the Raman scattering photons and the Raman pump photons. If the Rayleigh scattering (also called the zero Stokes shift) is visible, that difference can be computed, even when the wavelength of the Raman pump(s) varies over time. An intermediate option between constant temperature regulation and no temperature regulation is to allow the laser temperature to float within a certain temperature ranges (e.g., 30-60° C.), and to maintain the laser temperature within that range using a heater or cooling element.

Alternatively, other options can be used for frequency calibration of the Raman shift, including the use of a reference arm in the instrument, with a known chemical sample along the optical path, generating a Raman spectrum that is known and can be used for calibration purposes.

Accordingly, in some embodiments, a method of performing Raman spectroscopy, such as with the Raman system 1500, can include projecting a first Raman pump beam (e.g., from laser 1502a) at a first wavelength onto a sample 1506 (directly or through interleaving materials) from a standoff distance of at least about 1 cm, about 2 cm, about 5 cm, about 10 cm, about 30 cm, about 90 cm, about 2 m, about 4 m, including all values and sub ranges in between. As described herein with respect to FIG. 2, the first Raman pump beam can be scanned across the sample 1506 to reduce local heating. The first Raman beam can have a pulse duration of about 3 ms to about 2000 ms, including all values and sub ranges in between. The first Raman pump beam can irradiate the sample 1506 with at least about 10 mW, about 50 mW, about 200 mW, at least about 500 mW of power, including all values and sub ranges in between.

The method also includes detecting a first Raman signal emitted by the sample in response to the first Raman pump beam. This first Raman signal can represent a first Raman spectra/signature of the sample, and can also represent a first background spectra/signature (e.g., fluorescence from the sample, ambient light, etc.). In some cases, the first Raman signal can include the fluorescence and/or the ambient light.

The method can further include projecting a second Raman pump beam (e.g., from laser 1502b) at a second wavelength different than the first wavelength onto the sample from the same standoff distance. The method can also include detecting a second Raman signal emitted by the sample in response to the second Raman pump beam, where the second Raman signal represents a second Raman spectra/signature and a second background spectra/signature. As described in greater detail with respect to FIG. 17 below, the first and second Raman pump beams can be interleaved in some cases.

The method can further include generating a post-processed signature based on the first Raman signal, or the second Raman signal, or both. For example, the post-processed signature can be the difference between the first Raman spectra and the second Raman spectra.

The post-processed spectra/signature can have a background lower than or equal to the first background spectra/signature since, as described above, with both the background spectra being similar, their difference will be small. Accordingly, other than the Raman signature, the fluorescent and/or ambient light background can also be estimated based on the first and second Raman spectra. In some cases, the ambient light can be measured separately, and the post-processed spectra/signature can account for the measured ambient light. The post-processed spectra/signature can be used to identify the sample 1506 such as, for example, by comparing against a library of Raman spectra/signatures of different materials. The sample 1506 may be identified as (or containing) a hazardous material, a combustible material that is not ignited by virtue of the parameters of the first and/or second Raman beams, a light absorbing material that absorbs light from the first and/or second Raman beams without overheating (i.e., beyond a threshold), etc. The sample 1506 may be within a reaction vessel as illustrated in FIGS. 23-24, and the post-processed signature can identify at least one chemical species within.

In some cases, the system 1500 and this method can include aspects of the setup described for FIG. 19, and encompass illumination of the sample 1506 with at least one visible beam at the same position as the Raman beam. As described for FIG. 19, in some cases, two visible beams can be used, with each forming a different spot on the sample. This method can then include moving either the system 1500, or adjusting a working distance thereof, to reduce the distance between the spots as described for FIG. 19.

Instrument Timing and Synchronization

The difference Raman spectroscopy technique relies on the background signal (from sample fluorescence, ambient light, etc.) being common between the spectra acquired successively with different pump lasers. This may be difficult in a handheld situation where the aim of the user may be drifting over time. By illuminating different points on the sample and having varying distance between the sample surface and the instrument focal point, the Raman signal, the sample fluorescence, the collection efficiency of ambient light into the instrument may each vary. Different points on the sample may also have different chemical compositions (e.g., if the sample is a heterogeneous mixture) or different reflectivities (e.g., different colors), further contributing to the variation of the measured signals. The material under study may also exhibit bleaching of the fluorescence under illumination by the Raman laser, leading to a reduction of the fluorescence intensity over time: this is another source of time variation of the fluorescence signal.

To account for these variations, the difference Raman technique can be implemented in a manner consistent with dynamic signals. We achieve this by maintaining a short frame time (e.g., <0.5 seconds) for the acquisition of each difference Raman spectrum as well as the background spectrum. This short acquisition time reduces or minimizes differences between successive frames due to hand movement, sample variations, bleaching, etc.

The spectrometer may interleave a background frame between pairs of difference Raman frames. An example of acquisition sequence is as follow: one frame is acquired with Raman laser 1 on (Raman laser 2 off), a second frame is acquired with Raman laser 2 on (Raman laser 1 off), and a third frame is acquired with no Raman laser on. We maintain a short frame time (e.g., <0.5 s) for each frame to mitigate potential variations due to ambient light modulation, operator hand movements, fluorescence bleaching, and other causes of signal variations. The duration of the frames is usually the same for all frames but may be varied depending on exposure conditions: in the presence of high intensity ambient light (e.g., sunlight) or large sample fluorescence, it may be desirable to reduce the frame time (while keeping them all equal) to avoid saturation of the detector. The choice of frame time is a trade-off between reducing read-out noise (short frames are read out more often for a given total integration time and therefore tend to have more CCD read-out noise) and reducing potential variations of the signals (generally, the shorter the frames, the more robust the measurement is against time variation of the signal), while ensuring that the CCD does not saturate (which may involve limiting the maximum integration time).

The difference Raman system is compatible with an optional beam scanning of the laser source on the sample. As explained above, beam scanning increases eye safety, mitigates explosion risk, and averages the measurement over possible sample inhomogeneities. The CCD frame time of the Raman spectrometer is chosen to be an integer multiple of the scanning period (also sometimes referred to as a "base period"), so that each frame sees the same scanning pattern and experiences the same corresponding signal variations. If this was not the case, each frame may see different signals, because (1) the optical system throughput varies for different positions of the scanning mirror and (2) the different spots illuminated on the sample may have different reflectivities and/or chemical compositions, leading to different spectrum intensities and shapes. Synchronizing the frame timing with the beam scanning period makes it possible to suppress ambient light or sample fluorescence from the frames acquired with different Raman lasers as well as from potential background frames.

The ambient light sources may be modulated. For example, the intensity of ambient artificial light may vary at an integer multiple of the local utility frequency (e.g., 50 Hz or 60 Hz). Typically, a 100 Hz or 120 Hz modulation of the ambient light is observed for indoor measurements. To ensure that the spectrometer measures a constant or nearly constant level of ambient light, one can set the frame period (i.e., the time between the start of two consecutive frames) to be an integer multiple of ambient light modulation period (also sometimes referred to as a "base period"). In some cases, this base period is based on a flicker period of an ambient light source (e.g., a light source powered by an electric utility) that contributes to or is responsible for the background/ambient light. The base period can be an integer multiple of the flicker period, or vice versa. The flicker period of a known ambient light source can be determined based on a frequency analysis of the ambient light intensity, and can be (in some cases) about 8.33 ms to about 10 ms, including all values and sub ranges in between.

In some cases, the flicker period can be automatically determined as follows. The Raman system (i.e., any suitable Raman system as described herein) can include a GPS receiver (e.g., see I/O 1434 in FIG. 14) that can receive GPS information and determine its own location as a surrogate indication of the location of the sample. Once the sample's GPS location is known (e.g., the country of location), it can be compared against a table listing the electric current frequency employed by utilities in that location. For example, if the GPS location indicates the location of the sample as the United States, the flicker period can be estimated based on the knowledge that the electricity standard in the United states is 120 V, 60 Hz AC. Similarly, if the GPS location indicates the location of the sample as the United States, the flicker period can be estimated based on the knowledge that the electricity standard in the United states is 220 V, 50 Hz AC. In other cases, user input can specify the geo-location of the sample (e.g., such as via a user interface of the Raman system), and Following these considerations, an example embodiment of a timing scheme/method is illustrated in FIG. 17, which shows the acquisition cycle for differential Raman spectroscopy with interleaves measurements during frame periods selected based on beam scanning for eye safety/explosion mitigation and ambient light modulation, and specifies that:

A frame period (also sometimes referred to as a "measurement period") is defined by a CCD integration time of 130 ms followed by a readout time of 20 ms (the read-out time includes other time buffers and delays for system operation). The frame period (Laser 1 frame/Laser 2 frame/Background frame in FIG. 17) is thus 130 ms+20 ms=150 ms.

A laser scanning system operates at 20 Hz along a slow axis and 200 Hz along a fast axis to illuminates the sample in a raster scan pattern. The scan period is 1/(20 Hz)=50 ms. The frame period (Overall exposure/acquisition period in FIG. 17) is thus equal to 3 full scan periods.

The ambient light (Ambient Light Modulation in FIG. 17) is assumed here to be modulated at twice the utility frequency (either 50 Hz or 60 Hz based on the local standards). The light modulation period is thus 1/(2×50 Hz)=10 ms or 1/(2×60 Hz)=8.33 ms. The frame period is thus equal to either 15 or 18 full light modulation periods.

A measurement includes one or more of the following sequence: (1) Laser 1 is turned on and illuminates the sample; (2) the corresponding Raman spectrum is measured by the CCD, integrating for 130 ms between t=0 and t=130 ms; (3) the CCD is read out, laser 1 is turned off, and laser 2 is turned on; (4) a second Raman spectrum is measured by the CCD integrating for 130 ms, between t=150 ms and t=280 ms; (5) the CCD is read out and laser 2 is turned off; (6) a third spectrum (Background frame in FIG. 17) is measured by the CCD integrating for 130 ms, between t=300 ms and t=430 ms; and (7) the CCD is read out.

Such measurements result in three Raman spectra (i.e., a first Raman signal/spectra, a second Raman signal/spectra, and a background/ambient light signal/spectra) that can be used to extract the Raman spectrum of the sample (also sometimes referred to as a post-processed signature) and analyze its composition. The timing scheme described here is one example of how to synchronize the different modulations (ambient light modulation, laser beam scanning, spectrum acquisition frame). Other timing schemes are also possible. As illustrated in FIG. 17, the measurement of each Raman signal can be done during an integration period (CCD integration signal in FIG. 17) within each frame. Said another way, the first Raman signal/spectra can be measured during a first integration period, the second Raman signal/spectra can be measured during a second integration period, and the background/ambient light signal/spectra can be measured during a third integration period, each of which can be equal to each other.

In choosing the same integration time for the frame with laser 1 turned on and the frame with laser 2 turned on, it is assumed that the laser power on target is similar for laser 1 and laser 2. This may not always be the case and can be accounted for by scaling the respective spectra to equalize the strength of the Raman and fluorescent signature or by varying the integration times accordingly. In general, this results in the presence of an ambient light signature of the subtraction of the two Raman spectra. This signature may be unmixed using the information from the third frame (acquired with no laser on, measuring the ambient light as reflected by the sample and collected by the system).

Polarized Difference Raman Spectroscopy

If the Raman pump laser is polarized, and a polarization analyzer is used on the collected Raman signal, different Raman spectra may be recorded for the different polarization states of the scattered Raman photons. In particular, the relative heights of the different Raman peaks may be different. Polarized Raman spectroscopy can provide information on molecular or crystalline orientation.

Polarization Raman information can be collected together with difference Raman information. The Raman laser(s) output can be polarized prior to impinging on the sample, and either using free-space coupling between the laser and the telescope, or by using polarization-maintaining fiber, a polarized Raman pump beam can be sent to the sample (not shown). A polarizer may also be used to polarize the unpolarized output of a standard multi-mode fiber, although this results in a loss of power. On the collection side, a polarizer, such as a tourmaline crystal, that can be rotated between two orthogonal orientations can be used to analyze the collected light. Polarization Raman information can be collected at both wavelengths used in difference Raman spectroscopy, and the difference would contain such information. Data analysis may include computing the difference between the polarized difference Raman spectra obtain at two different orientations of the analyzer.

FIG. 34 illustrates an example of how polarized difference Raman information can be obtained by acquiring successive Difference Raman spectra with two different orientations of a polarizer using any suitable Raman system described herein. Raman spectra of a target sample 3402 can be acquired using any suitable system as described herein, and including at least a Raman laser 3404 and a spectrometer 3406. Here, in a first setting 3400a of the Raman system, a parallel polarizer 3408a is employed in front of the spectrometer 3406, so that the spectrometer receives a parallel polarized Raman signal. The collection protocol 3410a for this signal can be similar to that generally described for FIG. 17, and include a) Raman spectrum acquisition at a first pump wavelength; b) Raman spectrum acquisition at a second pump wavelength; and c) optionally, Raman spectrum acquisition with the laser(s) turned off. The result is a parallel-polarized Raman spectra of the sample 3402.

Then, in a second setting 3400b of the Raman system, a cross polarizer 3408b is employed in front of the spectrometer 3406, so that the spectrometer receives a cross polarized Raman signal. The collection protocol 3410b for this signal can also be similar to that generally described for FIG. 17, and include a) Raman spectrum acquisition at a first pump wavelength; b) Raman spectrum acquisition at a second pump wavelength; and c) optionally, Raman spectrum acquisition with the laser(s) turned off. The result is a cross-polarized Raman spectra of the sample 3402. The difference between the parallel-polarized Raman spectra and the cross-polarized Raman spectra can be computed at 3412 as the polarized difference Raman spectra.

Camera and/or Eye-Piece

The system may include a camera or an eyepiece that images the sample with enough magnification to distinguish features associated with the sample texture or granularity. This allows the user to locate points-of-interest, such as isolated particles to be analyzed. The camera may be used to add a functionality like that of a digital microscope to the Raman system.

In one embodiment, the Raman system has a fixed focal distance (e.g., 5-15 cm) and is positioned vertically, pointing down, with a horizontal focal plane. The user may position a sample, for example, using a three-axis stage, to bring an area of interest, for example, a particle or a fiber, at the Raman laser focus. The visual feedback provided by the instrument camera or eye-piece may be used to assist the user in this task. Once the sample is positioned properly, a measurement can be initiated, and the instrument can analyze the resulting spectral information to determine the composition of the analyte (e.g., a particle or fiber on a substrate). In another configuration, the Raman instrument is mounted on a vertical translation stage and the sample is moved using a two-dimensional translational stage in the horizontal plane. Overall, this provides three degrees of freedom for positioning the sample at the focus of the Raman laser.

In contrast to existing Raman microscopes, the instrument described here requires no ambient light shield, yet still offers increased eye safety, even in the absence of an enclosure around the entire instrument or around the sample compartment. This could allow for an open design that makes it easier to manipulate the sample. Since the increased eye safety uses laser beam scanning over an area about 1 mm×1 mm, the spatial resolution may be limited. It may sometimes be desirable to interrogate a smaller object (e.g., a particle with <100 μm diameter). In such a case, one can turn off the laser beam scanning. An interlock can then prevent the lasers from turning on until a sample compartment or instrument enclosure is closed. This interlock prevents the instrument from emitting an accessible beam whose effective irradiance is higher than that of a scanned beam. The instrument may thus maintain the laser safety classification obtained with the laser beam scanning on. For example, a class 3R Raman microscope may be designed in such manner.

A difference Raman system, paired with the microscopy capability, allows analysis of a sample with strong fluorescence and samples deposited on fluorescent substrates.

The standoff capability of the instrument described here, when paired with the imaging capability, results in a Raman microscope with a long working distance, which may be advantageous when analyzing a bulky sample.

Coarse Imaging

Forming small images of a target analyte can increase sensitivity and specificity for the analysis of solid mixtures and provide an approximate quantification from the statistical analysis of the particle distributions.

Consider a solid mixture with a dominant compound containing a small quantity of a minority compound. This may be a pharmaceutical pill with a small quantity of active compound embedded in a matrix of an inactive excipient. In the limit of uniform mixing of very small crystals, all sub-volumes of the sample have the same composition. However, if the grain sizes of the different compounds have a certain minimum size, and if small volumes whose dimensions do not greatly exceed the dimensions of the grain size in the mixture are probed, different volumes may have different concentrations of the minority compound. Thus, it may be advantageous to probe several distinct volumes to increase the odds of finding a volume with a larger concentration of the minority compound. This is one rationale for scanning a sample to increase the limit of detection of a minority compound.

Coarse imaging may also be useful to assess the uniformity of the mixing of different compounds in a powder mixture or pill, e.g., by measuring the relative concentrations of the different compounds in several distinct volumes. A spatial map can be created, revealing the spatial distribution of the different compounds and potential clustering effects.

Image Stabilization

The operator's hand motion can result in a drift of the instrument aim point during a measurement. If the sample is large, such as a bulk amount of powder, a useful measurement may be acquired even with poor aiming stability. However, if the sample is small (e.g., a grain or particle), poor or varying aim may result in a very inconsistent measurement, with varying mixing ratios between sample and substrates over the duration of the measurement. Proper analysis or chemical identification may then take longer.

A camera can be used to mitigate errors caused by drift in the instrument's aim point due to the operator's hand motion. More specifically, the camera can lock the aim point based on visual cues. Examples of visual cues are sample texture, topographical features, particles, and defects. The camera image may provide the input for an image stabilization system that relies on a beam steering mechanism to compensate drift of the aim point: (1) the camera acquires a first image, (2) the camera acquires a second image, (3) the onboard electronics analyze the two images are analyzed to approximate the angular deviation that could correct for a possible shift between the two images, and (4) the onboard electronics update the position of a laser beam scanning mirror to deflect the instrument aim by an amount opposite to the angular deviation observed. This compensates for the angular deviation. The process is then repeated as desired. This control loop uses two consecutive images as input and outputs a drive signal to a laser beam steering system. This implies that the optical path for the imaging system passes through the beam steering optics.

Alternatively, the input to the control loop may be the position of a laser spot within an image, e.g., with respect to some feature in the image (e.g., a particle of a given color or shape). If the distance between the sample and the instrument is known, the distance between two points on an image can be converted to an angular deviation as seen from the instrument output. That angular deviation can be used to produce the control signal to the beam steering optics, allowing compensation for aim fluctuations. This method does not require the optical path for the imaging system to pass through the beam steering optics.

The system may allow the user to indicate a feature of interest or desired measurement spot, for example, by pressing a touchscreen displaying an image of the area surrounding a sample, on which the system can lock. For example, the system may automatically steer the telescope optics to focus the Raman probe to that spot. The system maintains that aim, correcting automatically for the hand movements of the operator using information from the camera.

Focus Adjustment/Autofocus

The system may include a degree of freedom in the optical sub-system to adjust the distance at which the Raman lasers are focused. In other words, the standoff distance may be adjustable, either manually or by the operation of a motorized actuator. Examples of standoff distance tuning ranges may be from 30 cm to 4 meters, from 10 cm to 120 cm, from 2 cm to 25 cm.

Since the Raman laser beam sent to the sample and the Raman scattering coming from the sample follow the same path (i.e., the Raman scattering traces the laser beam's path backward through the telescope), if the system focuses the Raman laser beam on the sample, then the collection of the Raman scattering is also typically optimized.

FIGS. 18A and 18B illustrate the use of visible laser beams 1810 to mark the Raman pump beam's focus 1870 in a Raman spectroscopy system with a variable focus telescope/movable lens 1820 and a dichroic beam combiner 1830 that couples the visible laser beams and the Raman pump through the same optics. Crossing laser pointers may be used to indicate where the focal plane of the instrument is located: two visible laser beams 1810, collimated or with a low divergence, having a small diameter (for example between 0.5 mm and 5 mm) can be made to intersect at a point 1870 that is both on the optical axis of the instrument and in the focal plane of the instrument. Ignoring dispersion in the optical system, that point 1870 is thus where the Raman laser is focused. One of the two beams may be colinear with the instrument optical axis, so that it always indicates where the instrument is aiming, even if the sample is not in the focal plane.

The two beams may be differentiated with different colors. The two beams may illuminate the sample continuously or they may be pulsed. Such blinking laser pointers may be easier for the human eye to distinguish in bright illumination conditions. The brightness of the laser pointers may be tuned based on the ambient light brightness, e.g., based on user comfort. A sample fluorescence, pumped by the visible laser beam(s), may be detectable by the instrument. It may thus be desirable to turn on the visible pointer lasers selectively in-between CCD integration periods, for example during the read-out time between two consecutive frames.

As the instrument focal length or working distance may be adjustable, it is desirable that the directions of the two visible beams 1810 are adjusted accordingly, so that the two beams always intersect where the Raman laser is focused. We describe here one engineering solution to this issue: two visible laser beams, collimated or with a low divergence, having a small diameter (e.g., 1 mm diameter) are generated inside the instrument. Both beams are overlapped with the Raman laser beam using a dichroic beam splitter/mirror 1830 that is mostly transmissive for the Raman laser wavelength and mostly reflective for the wavelength of the visible laser beams. The visible beams are aligned so that they propagate parallel to the Raman laser beams at a point in the optical system where the Raman beam is collimated. The dichroic beam splitter is positioned within the optical system such that the visible beams pass through the moveable optical components (here, the movable lens 1820) of the optical system before exiting the instrument.

A first visible beam propagates along the optical axis at all points along its path. As a result, this beam indicates where the instrument is aiming. The second visible beam propagates parallel to the optical axis, but is decentered with respect to the optical axis, such that it comes out of the instrument at the edge of the optical aperture. Since this beam follows a path like the marginal rays in the optical instrument, it intersects the optical axis at the point where the instrument is focusing the Raman laser beams. We assume here minimal dispersion such that the focal point of the instrument is mostly similar at the wavelength of the visible beams and at the wavelengths of the Raman lasers. Since this second visible beam follows the trajectory of a marginal ray for the Raman lasers, and this remains true regardless of the position of the moveable components within the optical system, the second visible beam intersects the optical axis at the point where the instrument is focusing the Raman lasers. Consequently, the intersection of the two visible beams remains coincident with the focus of the Raman lasers, even as the instrument focal length is varied.

The dichroic beam splitter may also be inserted at a point where the Raman beam is not collimated (e.g., after the beams 1810 pass through the lens 1820). In this case, the on-axis pointer laser should still be parallel and coincident with the optical axis. And the second laser beam is inserted such that its direction after reflection from the dichroic beam splitter is parallel to the direction of the Raman ray crossing the off-axis position where the second laser pointer is inserted.

The system may include an autofocus mechanism to automatically adjust the distance between the instrument and the location of the Raman focus. This makes it easier to place the Raman focus is located on or in the sample. The autofocus may operate during the measurement to compensate for possible hand movements during the measurement. The autofocus system may allow for the definition of an offset such that the system is focusing some distance away from the first scattering surface, or some distance away from the surface that scatters light most. For example, the sample may be a liquid in a semi-transparent container: the autofocus feedback signal may indicate the distance from the instrument to the first scattering surface, in this case the interface between air and the semi-transparent container. But the system should be focused inside the liquid sample for adequate measurement of the analyte. An offset setting may thus be used so that the system focuses a short distance behind the first scattering surface, for example, 1 cm behind the first scattering surface. That offset may be set by the user or selected automatically. To implement this offset, the autofocus feedback signal uses a local ranging capability, i.e., the capability to measure the position of the system focal point with respect to the main scattering surface.

The autofocus mechanism may use a camera, such as the camera 1840, that looks out at the scene facing the instrument. The camera is displaced laterally a certain distance from the telescope optical axis. The on-axis laser pointer illuminates one point 1850 on the scene, and the position of that point with respect to the camera optical axis 1860 gives a rough estimate of the distance between the object illuminated by the on-axis laser and the instrument. This method is generally classified as a parallax method of estimating the rage of an object. This calculation exploits the known, constant distance and orientation of the Raman telescope optical axis with respect to the camera optical axis. The relationship between the position of the image the on-axis laser pointer spot, as seen by the camera 1840, and the distance from the instrument to that spot may be calibrated beforehand (e.g., in a factory) and stored as a lookup table.

A finer autofocus mechanism may be used after adjusting the position of the different moving elements of the Raman telescope according to that range information. This may rely on imaging the two spots from the two laser pointers and ensuring that they are overlapped. The relative position of the spots formed by the two laser pointers intersecting with the main scattering surface is a directional measure of the distance between the main scattering surface and the position of the Raman focus. It can thus be used as an input to a closed-loop control of the focus position.

FIG. 19 illustrates such use of a camera system for imaging and tracking a standoff Raman system's aim point. In FIG. 19, two cameras (camera 1, camera 2), with camera 1 having the same axis as the optical setup and camera 2 being offset from the optical setup, are employed. For camera 1, the image of laser 2 is always formed on its optical axis and in the center of its corresponding image, while for camera 2, the image of laser 2 is always formed off its optical axis. When laser 1, laser 2 (sometimes collectively referred to as a "ranging laser") intersect at the position of Raman focus (Position B), the images of these lasers are coincident with the optical axis of camera 1, and are equally spaced (but coincident with each other) from the optical axis of camera 2. The Position A, Position B images of camera 1 and camera 2 both indicates an offset between the images of laser 1, laser 2, indicating that these positions are not at the Raman focus. A user can then manipulate a movable element (such as the movable lens of FIGS. 18A, 18B) to obtain the desired Position B images for laser 1, laser 2.

If an offset is desired between the main scattering surface and the measurement spot (where the Raman laser is focused), the close-loop control can be set to target a specific non-zero distance (denoted as Δx in FIG. 19) between the spots formed by the two laser pointers intersecting with the main scattering surface. The Raman laser/pump beam then gets focused to a spot on or just below the sample surface. The distance between the focus of the Raman laser/pump beam and the Raman system itself can be about 2 cm, about 6 cm, about 10 cm, about 30 cm, about 90 cm, about 400 cm, including all values and sub ranges in between.

Accordingly, in some embodiments, a method of Raman spectroscopy, as can be carried out with any Raman system described herein, can include the system measuring the space between the Raman system and the sample, such as the sample of FIG. 19. In some cases, the spacing can be about 2 cm, about 10 cm, about 100 cm, about 400 cm, including all values and sub ranges in between. This measurement of the range of possible distances between the sample and the Raman system can be done, in some cases, by detecting the spot generated by the laser 2 (along the optical axis) using camera 2 (off the optical axis), and estimating the range based on the image of that spot on camera 2. In some cases, the distance between the spots formed by laser 1 and laser 2 on camera 1 and/or camera 2, detected by acquiring a sample image, can be used to make the measurement as explained herein. The autofocus mechanism can then operate to reduce the spacing/distance between the spots to make them overlay each other. Once done, the sample can be illuminated with the Raman pump beam, and the Raman signal/spectra measured.

Depth Profiling

The system may be capable of locating the position of the different interfaces along the optical axis. For example, if the instrument is targeting an analyte such that several transparent or semi-transparent objects (e.g., glass or plastic walls, windows, enclosures, containers, etc.) are positioned between the instrument and the analyte, the instrument may be capable of measuring the distance between the instrument and the successive interfaces. This can be achieved, for example, using a time-of-flight ranging system. The system may then prompt the user where the instrument should be focused with respect to these interfaces. For example, if an analyte is contained in a glass container located behind the closed window of a fume hood, the instrument should be focused a short distance (e.g., 5-10 mm) behind the interface formed by the air and the glass container. The instrument may be capable of autonomously and sequentially probing several points at or near the interfaces observed.

Uses of a Handheld Difference Raman Spectroscopy System

A handheld standoff (or proximal) difference Raman instrument can identify an unknown chemical by acquiring its Raman spectrum and comparing the Raman spectrum to a library of known Raman spectra. It can be used by pointing the instrument toward a sample located a short distance away from the instrument and pressing a trigger or other switch to initiate a measurement. The system then illuminates the sample with a Raman laser, collects the Raman scattering, obtains a spectrum of the Raman scattering using a spectrometer, digitizes the resulting spectrum, and uses various processing analogous to linear regression processing to compare the measured spectrum to a library of known spectra. For the instrument described here, several spectra can be used as input to the processing, including Raman spectra acquired at different Raman wavelengths and background spectra acquired with no Raman laser turned on.

The system may have a standoff distance that allows measurement through different interfaces (e.g., windows, enclosures, container walls). The standoff distance also allows measurement in cases where the instrument cannot be placed in proximity to a sample, either because a physical barrier exists, or because there is a risk of contamination to the instrument and/or user, or because any other ambient condition may prevent the instrument from being safely or practically placed near the sample.

The difference Raman system described can be used to analyze:
- Fluorescent samples, samples placed on fluorescent substrates, and samples in containers with fluorescent walls;
- Absorbing, dark, or colored materials, that may present an ignition risk;
- Hot materials that may emit a strong blackbody radiation;
- In addition, materials that can be readily measured by most existing Raman instruments can be measured by the instrument described here.

The instrument may be separated into two parts: (1) a telescope probe containing the optical system that focuses the Raman light onto the sample, collects the Raman scattering, and performs desired auxiliary functions (e.g., motor and associated controller to adjust the telescope focal distance, camera to visualize the sample or the scene around the sample, camera used for autofocus or image stabilization, laser pointers to indicate aim and focus position, laser beam scanning system for eye safety and explosion risk mitigation); and (2) an instrument core, containing the lasers, the spectrometer, and most of the electronics, interfaces, antennas and power supply. The two parts may be linked by an umbilical cable containing both electrical conductors for power and control signals as well as optical fibers to send the Raman laser light to the telescope and the Raman scattering back from the telescope to the spectrometer.

FIG. 16 illustrates such an example Raman system 1600 with the probe separated from the instrument. It is understood that, unless explicitly noted otherwise, components of FIG. 15 may be functionally and/or structurally similar to similarly named components of FIGS. 14, 15. For example, the telescope 1608 may be similar to the telescope 1508, and so on. FIG. 16 illustrates how the probe 1604, telescope 1608, camera 1610, motor 1630, and the motor controller 1628 can be disposed in a compartment/casing 1601b of the system 1600, while all other components collectively reside in a separate compartment 1601a.

Explained with reference to FIGS. 14-16, but applicable to any Raman system described herein, in some cases, a dispersive element may be disposed in the optical path prior to the spectrometer (e.g., between the probe 1404 and the spectrometer 1412) that receives the Raman signal and/or the background ambient signal. In this manner, the Raman signal(s) (e.g., the first Raman signal from laser 1 and the second Raman signal from laser 2 in FIG. 16) and/or the background/ambient light signal can be dispersed into their respective spectral components. Then, a detector array, such as the CCD 1414 in some cases, may be useful for detecting the spectral components to generate the corresponding spectra.

A display may be integrated with the instrument, with switches and buttons allowing the user to control the instrument. Alternatively, a remote controller, potentially with a screen, can be used as a user interface. Communication between the instrument and the remote controller may be via wired or wireless interfaces.

The standoff difference Raman spectrometer may be integrated onto a robotic platform (e.g., an unmanned ground or aerial vehicle).

A complete standoff difference Raman spectrometer or the telescope part of a two-part system may be mounted on a gimbal system. This gimbal system can be used to adjust the laser beam's orientation and to aim the laser beam at specific objects or analytes.

Reaction Monitoring

The system may be used to monitor a chemical reaction. Different probes can be used for such an application. A Raman probe may be directly coupled to a flow cell, or via one or more obstructions. FIG. 20 illustrates an example handheld standoff difference Raman spectrometer that focuses a Raman pump beam onto an analyte through obstructions, including a window and a wall of a container, for monitoring a chemical reaction in a beaker. (The spectrometer of FIG. 20 can be used for other measurements as well.) As illustrated in FIG. 20, in such setups, the window and/or the walls of the container can generate Raman scattering signals, so a user can choose a focus position for the Raman beam based on these scattering signals. A real-world example of such a setting is shown in FIG. 37, where a handheld standoff Raman system 3700 is used for identifying a chemical compound in a container 3710 through the glass window 3720 of a fume hood 3730, and from a distance of more than one foot.

A telescope probe, as described in the two-part system above, may be used to focus the Raman laser into a reaction vessel. The measurement can be realized either through the walls of the vessel, if the vessel is made of glass or plastic, or through a transparent observation port or an opening of the vessel.

FIG. 21 illustrates an example two-part standoff differential Raman spectroscopy system, controlled with a wireless controller 2110, with a probe module 2120 mounted on a robot arm 2130 and a core module 2140 (e.g., which can contain one or more other components as described for FIGS. 14-16) mounted on the robot chassis 2150 for testing a sample 2160.

FIG. 22 illustrates a two-part standoff differential Raman spectroscopy system useful in a laboratory setting for testing samples on microscope slides, for example. FIG. 22 illustrates the system, controlled with a wireless controller 2210, with a core module 2220 and a probe module 2230 mounted on a vertical stage 2240 above a sample stage 2250.

FIG. 23 illustrates a two-part standoff differential Raman spectroscopy system useful for testing samples through an opening in a vessel containing the sample, for example. FIG. 23 illustrates the system, controlled with a wireless controller (not shown), with a core module 2310 and a probe module 2320 mounted on a fixed ring holder 2330 above a sample 2340.

FIG. 24 illustrates a two-part standoff differential Raman spectroscopy system useful for testing samples through a side wall in a vessel containing the sample, for example. FIG. 24 illustrates the system, controlled with a wireless controller 2410, with a core module 2420 and a probe module 2430 mounted on a fixed ring holder 2440 to the side of a sample in a beaker 2450. FIG. 36 is a photograph of a one-part variation of the two-part system of FIG. 24, and shows a one part Raman system being similarly used to monitor a reaction inside a vessel. Any Raman system described herein, when employed in such a setting, can analyze the solution and determine in real-time its chemical composition, including reactants, products and intermediates.

FIGS. 25A-25B illustrates a two-part standoff differential Raman spectroscopy system with adjustable working distance, which can be similar to the system of FIG. 23 and be useful for testing different materials/phases in a sample through an opening in a vessel containing the sample. FIG. 25A shows the system focusing on a first liquid phase (Material 1) of the sample in a beaker, while FIG. 25B shows the system focusing deeper into the sample and onto the second liquid phase (Material 2), in order to measure the Raman spectrum for one or the other phase. The vertical position of the instrument could be adjusted using an external mechanical device (not shown) instead of adjusting the working distance of the system with the internal optics of the system.

FIGS. 26A-26B illustrates a two-part standoff differential Raman spectroscopy system useful for testing different materials/phases in a sample through a side wall in a vessel containing the sample, such as in a chemistry glassware. FIG. 26A shows the system focusing on a first liquid phase (Material 1) of the sample in a beaker, while FIG. 25B shows the system focusing at a different height into the sample, and onto the second liquid phase (Material 2), in order to measure the Raman spectrum for one or the other phase. The position and aim of the instrument can be adjusted using an external mechanical device (not shown) in order to measure the Raman spectrum for one or the other phase. Such a mechanical device may be manually actuated or motorized.

Some advantages of the system described here for such application are: mitigation of fluorescence (using difference Raman techniques), mitigation of ignition or explosion risk (via laser beam scanning), ability to operate with no ambient light shield (enabled by the acquisition of rapidly interleaved background frames and proper timing of the different processes), ability to measure at a distance, through windows, container walls or other obstacles (enabled by the standoff measurement modality).

The system may be used to monitor the relative concentrations of different species in a mixture, for example, reaction reagents, intermediate products, and final products. The system may output a graph of the relative concentration of the different compounds as a function of time.

Even if unknown compounds are present, the system's electronics may be able to unmix the measured total spectrum to obtain the spectra of the different compounds contributing to the total spectrum. Such unmixing becomes more reliable as system measures different concentration ratios for the different compounds over time.

The instrument's onboard electronics may also be able to track specific peaks in the Raman spectrum, potentially associating these peaks with specific chemical groups, and inferring possible chemical structures for the unknown compounds being measured.

When a measurement is realized through the walls of a reaction vessel, possible condensation on the walls of the reaction vessel may be a concern. Condensation may form if the vessel and/or its content is cooled to a temperature below the dew point of the ambient air. Condensation results in increased scattering of the Raman pump beam and of the Raman signal, decreasing the signal throughput and the signal-to-noise ratio of the measurement. To mitigate this issue, two main strategies may be used:

(1) the air immediately surrounding the external wall of the vessel may be maintained dry enough that the dew point is kept at a lower temperature than the temperature of the external wall. This may be achieved by enclosing the vessel in an enclosure filled with a dry gas, in which case the Raman system may be in or out of the enclosure. Alternatively, a flow of dry gas may be guided along the external walls of the reaction vessel.

(2) The temperature of the external wall of the reaction vessel may be maintained high enough that it is above the dew point of the ambient air. This may be achieved by thermally isolating the external wall from the solution contained in the reaction vessel, for example using a cavity or jacket filled with a low heat conduction material or vacuum. This thermal isolation solution should be transparent at the wavelength of the Raman pump laser and over the spectral range of the desired Raman signal. For example, a closed glass jacket filled with vacuum would provide such solution.

FIGS. 38A-38B illustrates an example approach to prevent or reduce formation of condensation, and illustrates an example reaction vessel 3803 being probed by a Raman system 3801. A standoff Raman analyzer 3801 analyzes the composition of a solution 3802 inside the reaction vessel 3803, and the condensation could otherwise lower the signal obtained when the Raman system 3801 analyzes the composition of the solution 3802. The vessel 3803 has a wall with cavities 3804 and 3805. Cavity 3805 allows for circulation of a temperature regulation material 3806 (such as any suitable liquid, or gas) to control the temperature of the solution 3802. The temperature regulation material exits at 3807. Cavity 3804 is either closed (as illustrated in FIG. 38B) or allows for the circulation of a liquid or gas (as shown in FIG. 38A). The material contained in or circulated through 3804 can either be a dry gas, vacuum, or other dry, low heat conduction material that allows for transmission of light in the visible and near-infrared spectral range. The reaction vessel is optionally closed with a lid 3810 or other interface. In the absence of cavity 3804, the external wall of the reaction vessel 3803 may be cold and condensation may form, scattering the Raman pump beam and the Raman signal and decreasing signal throughput. The vessel 3803 shown here may maintain the temperature of its external wall above the dew point, avoiding the formation of condensation.

FIGS. 39A-39B illustrate another example approach to prevent or reduce formation of condensation and illustrates a dry enclosure 3908 used to prevent formation of condensation on the walls of a reaction vessel 3903 disposed therein. The standoff Raman system may be located inside or outside the dry enclosure. A standoff Raman analyzer 3901 analyzes the composition of a solution 3902 inside a reaction vessel 3903, and any condensation could lower the signal obtained by the Raman system. The vessel 3903 may have a wall with cavities 3904 allowing for circulation of a temperature regulation material 3905 to control the temperature of the solution 3902. The temperature regulation material exits at 3906. The reaction vessel in contained in an enclosure 3908 filled a dry gas or other dry, low heat conduction material that allows for transmission of light in the visible and near-infrared spectral range. The reaction vessel is optionally closed with a lid 3907 or other interface. The Raman analyzer 3901 may be outside the dry enclosure (as illustrated in FIG. 39A) or inside the dry enclosure (as illustrated in FIG. 39B). In the absence of the dry enclosure 3908, condensation may form on the external wall of the reaction vessel 3903, scattering the Raman pump beam and the Raman signal and decreasing signal throughput. The dry enclosure 3908 lowers the temperature of the dew point, avoiding the formation of condensation on the walls of the reaction vessel 3903.

FIG. 40 illustrates another example approach to prevent or reduce formation of condensation and illustrates a dry gas flow used to prevent formation of condensation on the walls of a reaction vessel that the flow interacts with. A standoff Raman analyzer 4001 analyzes the composition of a solution 4002 inside a reaction vessel 4003, and any condensation could lower the Raman signal thereby obtained. The vessel may have a wall with cavities 4004 allowing for circulation of a temperature regulation material 4005 to control the temperature of the solution 4002. The temperature regulation material exits at 4006. A dry gas 4008 or other dry, low heat conduction fluid that allows for transmission of light in the visible and near-infrared spectral range may flow along the walls of the reaction vessel 4003 to avoid condensation on the walls. The reaction vessel is optionally closed with a lid 4007 or other interface. In the absence of dry gas 4008, condensation may form on the external wall of the reaction vessel 4003, scattering the Raman pump beam and the Raman signal and decreasing signal throughput. The dry gas 4008 lowers the temperature of the dew point, avoiding the formation of condensation on the walls of the reaction vessel 4003.

Robot-Mounted System

A standoff differential Raman spectroscopy system may be mounted on a robotic platform (air, ground or water-based), either remotely controlled or autonomous, as generally described for FIGS. 21, 27. Several features of the standoff difference Raman instrument make it well suited for such robot-mounted applications:

The standoff distance allows to maintain a safe distance between the robot and the analyte, reducing the risks of collisions between the robot and objects surrounding the analyte (containers, furniture, other analytes, etc.);

The standoff distance also allows to measure through obstacles such as clear container walls or windows;

The adjustable working distance makes it convenient to focus the system onto the analyte without requiring fine position control of the robot;

The visible laser pointers give feedback on the system aim and focus;

The range information (parallax) from the laser pointers give situation awareness to the robot controller and can prompt him to adjust the robot position for the measurement;

The camera image allows the user to see where the system is aimed and focused, and it allows to gather more information on the analyte (shape, color, etc.).

The standoff differential Raman spectroscopy system can be controlled remotely, either through a dedicated wired or wireless communication link or by interfacing with the robot communication system.

A modular standoff differential Raman spectroscopy system may be converted by a user from a handheld system to a robot-mounted system. FIG. 27 illustrates a modular standoff differential Raman spectroscopy system that can be converted by a user from a handheld system 2710 to a robot-mounted system 2750. Such system features a core component 2720 common to both modalities, and a set of adaptor plates (2730, 2740) containing the features particular to one modality or the other. For example, a handle 2730 may be desired for a handheld system but it is not required for a robot-mounted system. The handle 2730 can be detachable. Alternatively, a robot-mounted system may have requirements in term of mechanical, electrical, and communication interface with the robot that can be captured by a specific adaptor plate, such as the plate 2740.

Macroscope Embodiment

FIGS. 28A-28C illustrate Raman macroscope embodiments, offering both a visible image of the sample and enabling to run a Raman analysis of specific points within the field of view. The working distance is between 1 cm and 20 cm. Different mounting brackets and/or other options are presented: a stand-alone system 2810 held in place using independently adjustable/retractable feet (FIG. 28A); a tripod mounted system 2820 using a standard ¼-20 threaded hole or other mechanical interface (FIG. 28B); macroscope or stereo-microscope mount with included height adjustment (FIG. 28C). Mechanical interface can use the standard 3" cylinder mount of most commercial macroscope mounts.

The system may include a housing (that may in turn include a mounting bracket/options as noted herein) and be assembled with an optical front-end/assembly that allows for shorter working distance, between 2 cm and 20 cm for example. A short working distance while maintain a large optical aperture (e.g. between 1" and 2") can allow to collect the Raman signal with a large numerical aperture, which results in large collection efficiency. The optical front-end can also be used to image the sample at shorter wavelengths (e.g. in the visible spectral range) onto a camera (e.g. CCD or CMOS sensor).

Since it is in practice difficult to design an optical system with both high object-side numerical aperture and large field of view, it may be desirable to keep the field of view of the Raman optical subsystem small, and to allow for motion to bring the Raman beam over different points to be analyzed. In some cases, the camera can image the sample over a field of view greater than 5 mm with an object-space numerical aperture of less than 0.2, when the optical assembly has an object-space numerical aperture of at least 0.3 and a field of view of less than 2 mm. The motion can be either: (1) motion of the optical head with respect to a fixed instrument, with a fixed sample; (2) motion of the sample with respect to the fixed instrument and fixed optical head; (3) motion of the instrument (including optical head) with respect to a fixed sample.

The motion can be manually driven or motorized, using a motion controller. This allows to bring the high numerical aperture Raman beam above specific points to be interrogated, instead of relying on an optical design with both a high numerical and a large field of view for the Raman optical subsystem. The high numerical aperture (e.g. NA>0.2) of the Raman optical subsystem is desired to allow for larger collection efficiency and consequently larger signal. By opposition, the visible optical subsystem can have lower numerical aperture (e.g. NA<0.2), since the camera sensor (CCD, CMOS) can be very sensitive and can produce good quality image, which makes obtaining a large field of view (e.g. 1"×1") for the visible optical subsystem more practical. Both the Raman optical sub-system and the visible optical sub-system can have independently adjustable focus to allow their respective beams (i.e., the Raman beam and the visible beam) to come to focus at the sample surface or on a particular point of interest, which can be automatically identified by the processor/CPU of the system. By varying the focus of the visible image, a z-stack image can be acquired, with a 3D representation of the sample surface. This can be used to identify and sort the location of the points to be analyzed.

FIG. 29 illustrates a possible result screen (e.g., acquired by the system of FIG. 28B, and showing a fingerprint on a car door handle), showing a visible image 2910 of the area of interest, captured with a camera operating in the visible spectral range, and the results of Raman-based chemical identification realized at a discrete set of points across the area of interest. The locations of these points (indicated in FIG. 29 as the areas corresponding to "No match", "RDX", "Sugar", etc.) can be decided automatically by an image analysis algorithm. For example, particles to be analyzed can be located on the image based on brightness, shape (boundaries), polarization response (if polarized light is used for illumination and/or a polarization analyzer is used in front of the camera) or other methods. Random sampling or systematic analysis of all points located on a predefined grid or set of points can also be realized.

FIG. 30 illustrates several industrial design features of the macroscope system, including retractable or foldable feet 3010 that can possibly be independently adjusted to vary the angle of regard of the system; a threaded hole 3020 as a mechanical interface, for example for tripod mounting; shock absorbers to provide ruggedness to the system and prevent damages in case of drop; and a macroscope mechanical adaptor, constituted for example by a cylinder with ~3" outer diameter to fit most existing macroscope or stereoscope mounts.

Such macroscope would contain similar components as the ones contained in the handheld system described above, with the possible addition of a motion controller and mechanical stages allowing for the translation of the optical head with respect to the fixed instrument body. The optical head may also be modified to improve the image quality for the visible optical sub-system and the numerical aperture for the Raman optical sub-system. Accordingly, FIG. 31 illustrates an example system diagram of such a macroscope 3100. Unless noted otherwise, components of the macroscope 3100 may be structurally and/or functionally similar to similarly named components in FIG. 14-16. The system 3100 includes a moving subassembly 3100a (sometimes also referred to as the "optical head") that includes the probe 3104, the camera 3110, and the requisite beam shaping/guiding optics or optical assembly (MEMS mirror 3140, NIR focusing optics 3142, visible light focusing optics 3144, a beam splitter 3146, and visible-NIR focusing optics 3148 for optical coupling to the sample 3106. The Raman laser source 3102 and the spectrometer 3112 are formed outside the moving subassembly 3100a. An LED illuminator 3160 illuminates the sample to allow the acquisition of bright enough images with the visible imaging system.

The system 3100 also includes a motion controller 3150 and mechanical stages (not shown) allowing for the translation of the optical head 3100a with respect to the (rest of the) fixed instrument body. A flexible bellow 3170 allows the optical head to move with respect to the system enclosure while allowing the system to remain sealed. The motion can be manually driven or motorized, using the motion controller 3150. This makes it possible to bring the high numerical-aperture Raman beam above specific points to be interrogated, instead of relying on an optical design with both a high numerical and a large field of view for the Raman optical subsystem. The high numerical aperture (e.g., NA>0.2) of the Raman optical subsystem is desired to allow for higher collection efficiency and consequently larger signal.

In contrast, the visible optical subsystem can have lower numerical aperture (e.g., NA<0.2), since the camera sensor (CCD, CMOS) can be very sensitive and can produce good quality image, which makes obtaining a large field of view (e.g., 1"×1") for the visible optical subsystem more practical. Both the Raman optical sub-system and the visible optical sub-system (the optics 3142 and the optics 3144) can have independently adjustable focus to allow their respective beams to come to focus at the sample surface or on a particular point of interest. By varying the focus of the visible image, a z-stack image can be acquired, with a 3D representation of the sample surface. This can be used to identify and sort the location of the points to be analyzed.

FIG. 32 illustrates a system 3200 having a subassembly 3200a that can be similar to the system 3100, subassembly 3100a respectively in FIG. 31. In the system 3200, the motion controller 3250 controls movement of a motorized sample stage 3250, instead of (and/or in addition to) movement of the subassembly 3200a such as via, for example, control of an actuator.

FIG. 33 illustrates a system 3300 having a subassembly 3300a that can be similar to the system 3100, subassembly 3100a respectively in FIG. 31. In the system 3230, the motion controller 3350 is disposed external to a casing of the system 3300, and controls collective movement of the system 3300, including the subassembly 3300a, with respect to a stationary sample such as via, for example, control of an actuator.

It is understood that the various embodiments disclosed herein can be combined to obtain additive and/or alternative functionality. As a non-limiting example, the approaches to monitoring temperature rise and/or the use of fail-safe mechanisms can be applied to any Raman system design or setup (e.g., that in FIGS. 1, 3, 5, 9, 13-16, 20-28, 30-40) disclosed herein. As another example, any of the scan patterns may be executable by any Raman system design or setup disclosed herein. As yet another example, any Raman system disclosed herein can encompass two or more pump lasers as generally shown in FIG. 15.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein, unless clearly indicated to the contrary, should be understood to mean "at least one."

The phrase "and/or," as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in any claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in any claims, shall have its ordinary meaning as used in the field of patent law.

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of Raman spectroscopy, the method comprising:
acquiring interleaved measurements of a first Raman signal of a sample using a Raman pump beam at a first wavelength, a second Raman signal of the sample using a Raman pump beam at a second wavelength different than the first wavelength, and ambient light transmitted and/or scattered by the sample; and
generating a post-processed signature based on the interleaved measurements of the first Raman signal, the second Raman signal, and the ambient light,
wherein acquiring the interleaved measurements comprises:
measuring the first Raman signal over first measurement periods equal to a first integer multiple of a base period;
measuring the second Raman signal over second measurement periods equal to a second integer multiple of the base period; and
measuring the ambient light over third measurement periods equal to a third integer multiple of the base period.

2. The method of claim 1, wherein generating the post-processed signature comprises determining a difference between the first Raman signal and the second Raman signal.

3. The method of claim 1, wherein generating the post-processed signature comprises estimating a Raman signature of the sample and a fluorescent and ambient light background, based on the first Raman signal and the second Raman signal.

4. The method of claim 1, wherein measuring the first Raman signal comprises scanning a first Raman pump beam through a scan pattern over at least a portion of the sample during each of the first measurement periods.

5. The method of claim 1, wherein the first integer multiple of the base period is equal to the second integer multiple of the base period and the third integer multiple of the base period.

6. The method of claim 1, wherein the base period is based on a flicker period of an ambient light source.

7. The method of claim 6, further comprising:
determining the flicker period of the ambient light source based on a frequency analysis of the ambient light intensity.

8. The method of claim 6, wherein the base period is an integer multiple of the flicker period.

9. The method of claim 6, wherein the flicker period is an integer multiple of the base period.

10. The method of claim 6, wherein the flicker period is about 8.33 ms to about 10 MS.

11. A system for Raman spectroscopy, the system comprising:
at least one Raman pump source to emit a first Raman pump beam at a first wavelength and a second Raman pump beam at a second wavelength different than the first wavelength;
a detector to acquire interleaved measurements of a first Raman signal of a sample in response to the first Raman pump beam, a second Raman signal of the sample in response to the second Raman pump beam, and ambient light transmitted and/or scattered by the sample; and
a processor, operably coupled to the detector, to generate a post-processed signature based on the interleaved measurements of the first Raman signal, the second Raman signal, and the ambient light,
wherein the detector is configured to acquire the interleaved measurements by:
measuring the first Raman signal over first measurement periods equal to a first integer multiple of a base period;
measuring the second Raman signal over second measurement periods equal to a second integer multiple of the base period; and
measuring the ambient light over third measurement periods equal to a third integer multiple of the base period.

12. The system of claim 11, further comprising:
a beam scanner, in optical communication with the at least one Raman pump source, to scan the first Raman pump beam through a scan pattern over at least a portion of the sample during each of the first measurement periods.

13. The system of claim 11, wherein the first integer multiple of the base period is equal to the second integer multiple of the base period and the third integer multiple of the base period.

14. The system of claim 11, wherein the base period is based on a flicker period of an ambient light source.

15. The system of claim 14, wherein the processor is configured to determine the flicker period of the ambient light source based on a frequency analysis of the ambient light intensity.

16. The system of claim 14, wherein the processor is configured to determine the flicker period based on an electric utility frequency at a location of the sample.

17. The system of claim 16, wherein the processor is configured to determine the electric utility frequency based on the location of the sample.

18. A method of Raman spectroscopy of a sample, the method comprising:
scanning a first Raman pump beam at a first wavelength in a scan pattern across the sample over a first scan period;
measuring a first Raman signal scattered by the sample in response to the first Raman pump beam over a first integration period;
scanning a second Raman pump beam at a second wavelength different than the first wavelength in the scan pattern across the sample over a second scan period;
measuring a second Raman signal scattered by the sample in response to the second Raman pump beam over a second integration period; and
forming a post-processed signature based on the first Raman signal and the second Raman signal.

19. The method of claim 18, wherein the sample is in a reaction vessel or a flow cell, and further comprising:
identifying at least one chemical species in the reaction vessel based on the post-processed signature.

20. The method of claim 18, further comprising:
measuring ambient light transmitted and/or scattered by the sample over a third integration period, and
wherein forming the post-processed signature is based on the first Raman signal, the second Raman signal, and the ambient light.

21. The method of claim 20, wherein the first integration period is equal to the second integration period and the third integration period.

22. The method of claim 20, wherein the first integration period is based on a flicker period of the ambient light.

23. The method of claim 22, wherein the first integration period is equal to an integer multiple of the flicker period.

24. The method of claim 22, further comprising:
determining the flicker period based on a frequency analysis of the measured ambient light intensity.

25. The method of claim 22, further comprising:
determining the flicker period based on an electric utility frequency at a location of the sample.

26. The method of claim 25, further comprising:
determining the location of the sample based on a Global Positioning System (GPS) signal.

27. The method of claim 25, further comprising:
determining the location of the sample based on user input.

* * * * *